United States Patent
Brodin et al.

(10) Patent No.: US 6,380,230 B1
(45) Date of Patent: Apr. 30, 2002

(54) CARBOXAMIDOTHIAZOLE DERIVATIVES, PREPARATION, PHARMACEUTICAL COMPOSITIONS CONTAINING THEM

(75) Inventors: Roger Brodin, Montpellier; Robert Boigegrain, Assas; Eric Bignon, Pinsaguel; Jean Charles Molimard, Saint Gely Du Fesc; Dominique Olliero, Montpellier, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/508,830

(22) PCT Filed: Sep. 18, 1998

(86) PCT No.: PCT/FR98/02007

§ 371 Date: Jun. 2, 2000

§ 102(e) Date: Jun. 2, 2000

(87) PCT Pub. No.: WO99/15525

PCT Pub. Date: Apr. 1, 1999

(30) Foreign Application Priority Data

Sep. 19, 1997 (FR) .............................. 97 11718
Apr. 23, 1998 (FR) .............................. 98 05106

(51) Int. Cl.[7] ..................... C07D 417/12; A61K 31/425
(52) U.S. Cl. ........................ 514/371; 548/181
(58) Field of Search ........................ 548/181; 514/371

(56) References Cited

U.S. PATENT DOCUMENTS

| 4,060,626 A |   | 11/1977 | Hrstka et al. |
| 5,189,049 A |   | 2/1993 | Frehel et al. |
| 5,314,889 A |   | 5/1994 | Boigegrain et al. |
| 5,380,736 A | * | 1/1995 | Boigegrain ........... 544/369 |
| 5,656,648 A |   | 8/1997 | Boigegrain et al. |

FOREIGN PATENT DOCUMENTS

| EP | 432040 | 6/1991 |
| EP | 518731 | 12/1992 |
| EP | 611766 | 8/1994 |

OTHER PUBLICATIONS

Fisher et al., A Convenient Synthesis of 6–Azaindole, *Journal of Heterocyclic Chemistry*, vol. 6, pp. 775–776 (1969).

* cited by examiner

*Primary Examiner*—Robert Gerstl
(74) *Attorney, Agent, or Firm*—Michael D. Alexander; Paul E. Dupont

(57) ABSTRACT

The present invention relates to cholecystokinin (CCK)-agonist substituted thiazoles of formula:

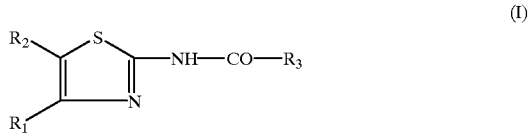

(I)

in which $R_1$ is a substituted phenyl group, $R_2$ is a group chosen from $CH_2$—$R_7$, $(CH_2)_2$—$R_7$, S—$CH_2$—$R_7$, $CH_2$—S—$R_7$ and $(C_5$–$C_8)$alkyl with $R_7$ being a $(C_5$–$C_7)$cycloalkyl group, and $R_3$ is a group

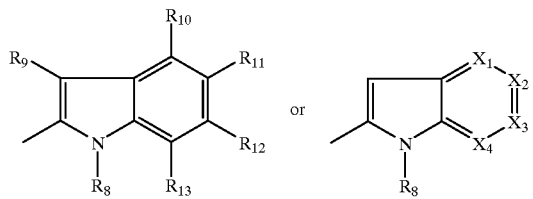

with $R_8$ being a group $(CH_2)_n R_{15}$ or

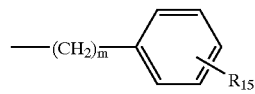

and $R_{15}$ being COOH or COO($C_1$–$C_4$)alkyl. The invention also relates to a process for the preparation of the pharmaceutical compositions containing them and to their uses for the preparation of medicines.

33 Claims, No Drawings

CARBOXAMIDOTHIAZOLE DERIVATIVES, PREPARATION, PHARMACEUTICAL COMPOSITIONS CONTAINING THEM

This application is a 371 of PCT/FR98/02007 filed Sep. 18, 1998.

The present invention relates to cholecystokinin (CCK)-agonist substituted thiazoles and more particularly agonists of the cholecystokinin type A (CCK-A) receptors, to a process for their preparation and to medicines containing them.

CCK is a peptide which, in response to an ingestion of food, is secreted peripherally and participates in regulating many digestive processes (Crawley J. N. et al., Peptides, 1994, 15 (4), 731–735).

CCK has also been identified in the brain, and might be the most abundant neuropeptide acting as a neuromodulator of cerebral functions by stimulation of CCK-B type receptors (Crawley J. N. et al., Peptides, 1994, 15 (4), 731–735). In the central nervous system, CCK interacts with dopamine-mediated neuronal transmission (Crawley J. N. et al., ISIS Atlas of Sci., Pharmac., 1988, 84–90). It also plays a role in mechanisms involving acetylcholine, GABA (γ-aminobutyric acid), serotonin, opioids, somatostatin, and substance P and in ion channels.

Its administration brings about physiological changes: palpebral ptosis, hypothermia, hyperglycaemia, catalepsis; and behaviour changes: hypolocomotion, reduction in searching, analgesia, a change in the learning faculty and a change in sexual behaviour and satiety.

CCK exerts its biological activity via at least two types of receptors: CCK-A receptors located mainly peripherally, and CCK-B receptors essentially present in the cerebral cortex. The CCK-A receptors of peripheral type are also present in certain zones of the central nervous system, including the postrema area, the tractus solitarius nucleus and the interpedoncular nucleus (Moran T. H. et al., Brain Research, 1986, 362, 175–179; Hill D. R. et al., J. Neurosci., 1990, 10, 1070–1081; with, however, specific differences (Hill D. R. et al., J. Neurosci., 1990, 10, 1070–1081); Mailleux P. et al., Neurosci. Lett., 1990, 117, 243–247; Barrett R. W. et al., Mol. Pharmacol., 1989, 36, 285–290; Mercer J. G. et al., Neurosci Lett., 1992, 137, 229–231; Moran T. H. et al., Trends in Pharmacol. Sci., 1991, 12, 232–236).

At the peripheral level, via the CCK-A receptors (Moran T. H. et al., Brain Research, 1986, 362, 175–179), CCK delays gastric drainage, modulates intestinal motility, stimulates vesicle contraction, increases bile secretion and controls pancreatic secretion (McHugh P. R. et al., Fed. Proc., 1986, 45, 1384–1390; Pendleton R. G. et al., J. Pharmacol. Exp. Ther., 1987, 241, 110–116).

The role of CCK in the satiety signal is supported by the fact that the plasmatic concentrations of CCK, which are dependent on the composition of the meals (high concentrations of proteins or lipids) are, after meals, higher than those observed before meals (Izzo R. S. et al., Regul. Pept., 1984, 9, 21–34; Pfeiffer A. et al., Eur. J. Clin. Invest., 1993, 23, 57–62; Lieverse R. J., Gut, 1994, 35, 501). In bulimia sufferers, there is a decrease in the secretion of CCK induced by a meal, (Geraciotti T. D. Jr. et al., N. Engl. J. Med., 1988, 319, 683–688; Deylin M. J. et al., Am. J. Clin. Nutr., 1997, 65, 114–120) and a lowering of the CCK concentrations in the cerebrospinal fluid (Lydiard R. B. et al., Am. J. Psychiatry, 1993, 150, 1099–1101). In the T lymphocytes, which is a cell compartment that may reflect central neuronal secretions, the basal CCK concentrations are significantly lower in patients suffering from bulimia nervosa (Brambilla F. et al., Psychiatry Research, 1995, 37, 51–56). Treatments (for example with L-phenylalanine, or trypsin inhibitors) which increase the secretion of endogenous CCK give rise to a reduction in feeding in several species, including man (Hill A. J. et al., Physiol. Behav., 1990, 48, 241–246; Ballinger A. B. et al., Metabolism, 1994, 43, 735–738). Similarly, the administration of exogenous CCK reduces feeding in many species, including man (Crawley J. N. et al., Peptides, 1994, 15, 731–755).

The inhibition of feeding by CCK is mediated by the CCK-A receptor. Devazepide, an antagonist which is selective for the CCK-A receptors, inhibits the anorexigenic effect of CCK, whereas the selective agonists of these receptors inhibit feeding (Asin K. E. et al., Pharmacol. Biochem. Behav., 1992, 42, 699–704; Elliott R. L. et al., J. Med. Chem., 1994, 37, 309–313; Elliott R. L. et al., J. Med. Chem., 1994, 37, 1562–1568). Furthermore, OLEFT rats, which do not express the CCK-A receptor, are insensitive to the anorexigenic effect of CCK (Miyasaka K. et al., 1994, 180, 143–146).

Based on these lines of evidence of the key role of CCK in the peripheral satiety signal, the use of CCK agonists and antagonists as medicines in the treatment of certain eating behaviour disorders, obesity and diabetes is indisputable. A CCK-receptor agonist can also be used therapeutically in the treatment of emotional and sexual behaviour disorders and memory disorders (Itoh S. et al., Drug. Develop. Res., 1990, 21, 257–276), schizophrenia, psychosis (Crawley J. N. et al., Isis Atlas of Sci., Pharmac., 1988, 84–90 and Crawley J. N., Trends in Pharmacol. Sci., 1991, 12, 232–265), Parkinson's disease (Bednar I. et al., Biogenic amine, 1996, 12 (4), 275–284), tardive dyskinesia (Nishikawa T. et al., Prog. Neuropsychopharmacol. Biol. Psych., 1988, 12, 803–812; Kampen J. V. et al., Eur. J. Pharmacol., 1996, 298, 7–15) and various disorders of the gastrointestinal sphere (Drugs of the Future, 1992, 17 (3), 197–206).

CCK-A receptor agonists of CCK are described in the literature. For example, certain products having such properties are described in EP 383,690 and WO 90/06937, WO 95/28419, WO 96/11701 or WO 96/11940.

Most of the CCK-A receptor agonists described to date are of peptide nature. Thus, FPL 14294 derived from CCK-7 is a powerful, unselective CCK-A receptor agonist towards CCK-B receptors. It has powerful inhibitory activity on feeding in rats and in dogs after intranasal administration (Simmons R. D. et al., Pharmacol. Biochem. Behav., 1994, 47 (3), 701–708; Kaiser E. F. et al., Faseb, 1991, 5, A864). Similarly, it has been shown that A-71623, a tetrapeptide agonist which is selective for CCK-A receptors, is effective in models of anorexia over a period of 11 days and leads to a significant reduction in weight gain when compared with the control in rodents and cynomologous monkeys (Asin K. E. et al., Pharmacol. Biochem. Behav., 1992, 42, 699–704). Similarly, structural analogues of A 71623, which have good efficacy and selectivity for CCK-A receptors, have powerful anorexigenic activity in rats (Elliott R. L. et al., J. Med. Chem., 1994, 37, 309–313; Elliott R. L. et al., J. Med. Chem., 1994, 37, 1562–1568). GW 7823 (Henke B. R. et al., J. Med. Chem., 1996, 39, 2655–2658; Henke B. R. et al., J. Med. Chem., 1997, 40, 2706–2725), a 1,5-benzodiazepine, is an in vitro CCK-A receptor agonist. This molecule is also active orally on the contraction of the bile vesicle in mice and on feeding in rats.

Cholecystokinin-antagonist substituted thiazoles are described in European patent EP 432,040 and European patent application EP 518,731.

European patent application EP 518,731 describes compounds which interact with the gastrin and cholecystokinin receptors, of formula:

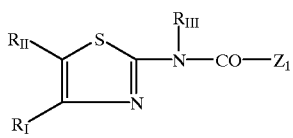

in which:

$Z_1$ can in particular be an indolyl group of formula:

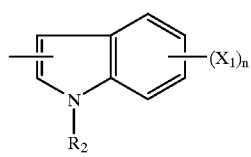

in which $X_i$ has various meanings and $R_2$ can be hydrogen; a $(C_1-C_4)$alkyl group; an optionally esterified carboxyalkylene group of formula $Z_2COOR$ in which $Z_2$ is a $(C_1-C_4)$alkylene and R is H, a benzyl, a $(C_1-C_6)$alkyl; a carbamoylalkylene group of formula $Z_2CONR_{IV}R_V$ in which $R_{IV}$ and $R_V$ are each independently hydrogen, a $(C_1-C_6)$alkyl or form a saturated heterocycle with the nitrogen; an acyl group of formula $COR_{VI}$ in which $R_{VI}$ is a $(C_1-C_4)$alkyl or a phenyl; an alkoxycarbonyl group of formula $COOR_{VII}$ in which $R_{VII}$ is a tert-butyl or a benzyl.

However, among the compounds of formula 1 described in that application, none contains an indolyl group simultaneously containing groups Xi and $R_2$, which are other than hydrogen. The compounds of formula 1 and their salts are described in EP 518,731 as inhibiting the binding of cholecystokinin to its receptors. They are more or less selective for the type A and B receptors and for the more or less powerful gastrin antagonists.

As a representative of these compounds, mention may be made in particular of the potassium salt of 2-[4-(2-chlorophenyl)thiaz-2-ylcarbamoyl]indole-1-acetic acid or SR 27897 B, which is known as a powerful CCK-A receptor antagonist (Eur. J. Pharmacol., 1993, 1, 13–19).

European patent application EP 611,766 describes cholecystokin receptor agonists on the pancreatic amylase test. These compounds correspond to the formula:

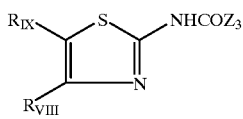

in which:

$R_{VIII}$ is a (hetero)aryl radical selected from 4-chloro-2,6-dimethoxyphenyl, 2,6-dimethoxy-4-methylphenyl, 2,4,5-trimethoxyphenyl, 4-methyl-2,3,6-trimethoxyphenyl, 2,6-dimethoxy-4-ethylphenyl, 2,4,6-trimethoxy-5-chlorophenyl, 2,4,6-trimethoxy-3-pyridinyl, 2,4-dimethoxy-6-methyl-3-pyridinyl, 6-chloro-2,4-dimethoxy-5-pyrimidinyl, 2,4,6-trimethoxy-5-pyrimidinyl, 5-chloro-2,4-dimethoxyphenyl, 5-chloro-2-methoxy-4-methylphenyl, 2,5-dimethoxy-4-methylphenyl, 4-trifluoromethyl-2,6-dimethoxyphenyl, 2,4-dimethoxy-5-methylphenyl, 5-ethyl-2,4-dimethoxyphenyl and 2,4-dimethoxyphenyl groups;

$R_{IX}$ is a hydrogen, a $(C_1-C_4)$alkyl or a benzyl; with the limitation that $R_{IX}$ is necessarily hydrogen when $R_{VIII}$ is a phenyl substituted simultaneously at positions 2 and 6 or when $R_{VIII}$ is a 3-pyridyl radical substituted simultaneously at positions 2 and 4 or $R_{VIII}$ is a 5-pyrimidinyl radical substituted simultaneously at positions 4 and 6;

$Z_3$ is a 3-quinolyl group or a 2-indolyl group of formula:

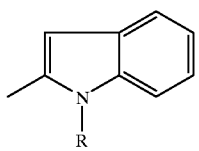

in which R is hydrogen, an acetyl group or a group $CH_2COOR'$, R' being hydrogen or a $(C_1-C_4)$alkyl, as well as the pharmaceutically acceptable salts thereof.

The object of the invention is, more precisely, to propose a novel family of substituted thiazoles that are particularly advantageous for their CCK-A receptor agonist activity.

The compounds according to the invention underwent systematic studies to characterize:

their ability to displace [$^{125}$I]-CCK from its binding sites present on rat pancreatic membranes (CCK-A receptors) or on 3T3 cells which express the human CCK-A recombinant receptor;

their CCK-A receptor agonist property via their capacity to induce in vitro a mobilization of the intracellular calcium in 3T3 cells which express the human CCK-A receptor.

Advantageously, the substituted thiazoles according to the present invention show a capacity to bind to the CCK-A receptors and to stimulate, like CCK, the mobilization of intracellular calcium in a cell line which expresses the human CCK-A recombinant receptor. They turn out to be CCK-A receptor agonists.

The compounds of the present invention were also studied in vivo, by evaluating their capacity to block gastric drainage in mice. As with CCK, these compounds block gastric drainage in mice and thus behave in vivo as CCK-A receptor agonists.

Surprisingly, they prove to be more powerful agonists than the substituted thiazoles described in patent application EP 611,766. These improved performance levels were assessed, on the one hand, in vitro on the mobilization of intracellular calcium, and, on the other hand, in vivo, via their intraperitoneal administration, by their capacity to block gastric drainage in mice.

Consequently, a first subject of the present invention is compounds of formula (I):

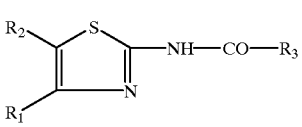

(I)

in which:
R₁ is a substituted phenyl group of formula:

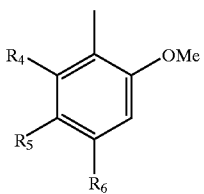

R₂ is a group selected from:
CH₂—R₇,
(CH₂)₂—R₇,
S—CH₂—R₇,
CH₂—S—R₇,
(C₅–C₈) alkyl;
R₃ is:
i) a 2-indolyl of formula:

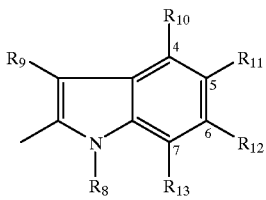

or
ii) a pyrrolopyridyl of formula:

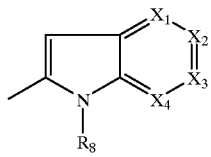

in which one of the groups $X_1$, $X_2$, $X_3$ and $X_4$ is N, the others being $CR_{14}$;
R₄ is hydrogen or a methoxy group;
R₅ is hydrogen, a methyl, ethyl, isopropyl, methoxy or ethoxy group or a halogen;
R₆ is hydrogen, a methyl, ethyl or methoxy group or a halogen;
or R₅ and R₆, considered together, are a methylene-dioxy group; on the condition that the substituents R₄, R₅ and R₆ are not simultaneously hydrogen;
R₇ is a (C₅–C₇)cycloalkyl group which is unsubstituted or substituted with one or two methyls;
R₈ is a group $(CH_2)_nR_{15}$ or a group:

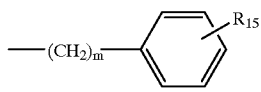

R₉ is hydrogen or a methyl group;
R₁₀, R₁₁, R₁₂ and R₁₃ are, independently of each other, hydrogen, a methyl, ethyl, hydroxyl, acetyloxy, methoxy, ethoxy, methylthio, trifluoromethyl or amino group or a halogen;
R₁₄ is hydrogen or a methoxy group;
R₁₅ is a COOH group or a group COOR₁₆;
R₁₆ is a group (C₁–C₄)alkyl;
n=1, 2, 3, 4 or 5;
m=0 or 1;
as well as the salts or solvates thereof.

The term (C₁–C₄)alkyl is understood to denote a linear or branched alkyl group and more particularly methyl, ethyl, isopropyl, isobutyl and tert-butyl groups.

The term (C₅–C₈)alkyl is understood to denote a linear or branched alkyl and more particularly n-pentyl, n-hexyl, n-octyl and 5,5-dimethylhexyl groups.

The term halogen is understood to refer to a chlorine, fluorine or bromine atom, chlorine being preferred.

The addition salts of these compounds are those obtained with inorganic or organic bases: non-toxic pharmaceutically acceptable salts are preferred, but other salts which can be used to isolate or purify the compounds of formula (I) are also within the invention.

The salts of the compounds of formula (I) comprise the salts with organic or inorganic bases, for example the alkali metal or alkaline-earth metal salts such as the sodium, potassium or calcium salts, the sodium and potassium salts being preferred, or with an amine, such as trometamol, or alternatively the salts of arginine, of lysine, of N-methyl-D-glucamine or of any physiologically acceptable amine.

The present invention also covers the solvates formed by the compounds of formula I with water or inorganic or organic acids such as hydrochloric acid, hydrobromic acid, trifluoroacetic acid, sulphuric acid, sulphonic acid, phosphoric acid, 2-naphthalenesulphonic acid or p-toluenesulphonic acid.

Most particularly, the present invention relates to the compounds of formula (I):
in which:
R₁ is a substituted phenyl group of formula:

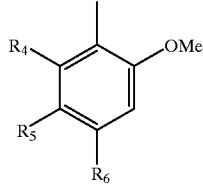

R₃ is:
i) a 2-indolyl of formula:

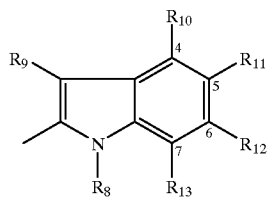

or
ii) a pyrrolopyridyl of formula:

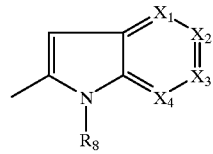

in which $X_1$, $X_2$, $X_3$ and $X_4$ are as defined above;
R₄ is hydrogen or a methoxy group;
R₅ is hydrogen, a methyl, ethyl, methoxy or ethoxy group or a halogen;
R₆ is hydrogen, a methyl, ethyl or methoxy group or a halogen;

or $R_5$ and $R_6$, considered together, are a methylene-dioxy group; on the condition that the substituents $R_4$, $R_5$ and $R_6$ are not simultaneously hydrogen;

$R_{10}$, $R_{11}$, $R_{12}$ and $R_{13}$ are, independently of each other, hydrogen, a methyl, ethyl, methoxy, ethoxy, methylthio, trifluoromethyl or amino group or a halogen;

$R_2$, $R_8$ and $R_9$ are as defined above;

as well as the salts or solvates thereof.

The subject of the present invention is, more particularly, compounds of formula (I) in which $R_2$ is a group selected from:

$(CH_2)_2$—$R_7$ and
S—$CH_2$—$R_7$;

with $R_1$, $R_3$ and $R_7$ being as defined above for (I), as well as the salts and solvates thereof.

Preferably, $R_7$ is a cyclopentyl, a cyclohexyl, a 4,4-dimethylcyclohexyl or a cycloheptyl.

According to the present invention, the preferred compounds of formula (I) are those in which $R_2$ is a cyclohexylethylene and the substituents $R_1$ and $R_3$ have the values defined above for (I), as well as the salts or solvates thereof.

The compounds of formula (I) in which $R_1$ is a 4-methyl-2,5-dimethoxyphenyl or a 4-chloro-2,5-dimethoxyphenyl and the substituents $R_2$ and $R_3$ have the values defined above for (I), as well as the salts and solvates thereof, are also preferred compounds; the value $R_1$=4-chloro-2,5-dimethoxyphenyl being particularly preferred.

One specific group of compounds consists of the compounds of formula (I) in which $R_3$ is a pyrrolopyridyl of formula:

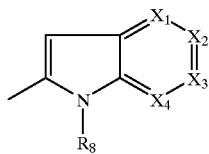

in which $X_1$, $X_2$, $X_3$, $X_4$ and $R_8$ are as defined above for (I), as well as the salts and solvates thereof.

Another specific group of compounds consists of the compounds of formula (I) in which $R_3$ is a 2-indolyl group of formula:

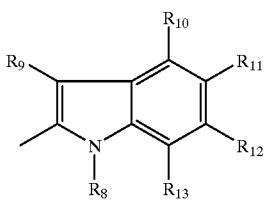

with $R_8$, $R_9$, $R_{10}$, $R_{11}$, $R_{12}$ and $R_{13}$ being as defined for (I), as well as the salts and solvates thereof.

The compounds of formula (I) which are also preferred are those in which $R_1$ and $R_2$ are as defined above for (I) and $R_3$ is a 2-indolyl group in which one of the substituents $R_{10}$, $R_{11}$, $R_{12}$ or $R_{13}$ is other than hydrogen. Particularly, when $R_3$ is a 2-indolyl group, the preferred compounds are those in which $R_8$ is a carboxy-alkylene group of formula $(CH_2)_n$—COOH, more particularly a carboxymethylene group. The compounds of formula (I) which are even more particularly preferred are those in which one or two of the substituents $R_{10}$, $R_{11}$ and $R_{13}$ are a methyl, methoxy or trifluoromethyl group, a chlorine or a fluorine, the third, as well as $R_{12}$ and $R_9$, being hydrogen, as well as the salts and solvates thereof.

Thus, the groups of compounds which are particularly preferred according to the invention are those represented by the compounds of formula:

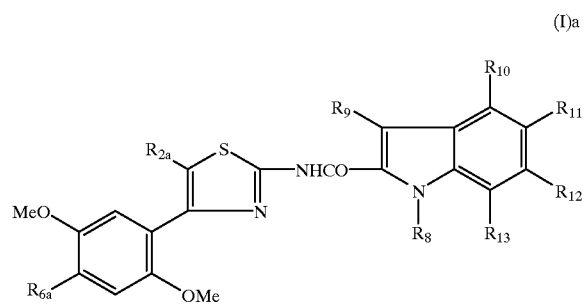

(I)a in which:

$R_{2a}$ is a group selected from:
$(CH_2)_2R_7$
S—$CH_2R_7$;

$R_{6a}$ is a chlorine or a methyl;

$R_7$, $R_8$, $R_9$, $R_{10}$, $R_{11}$, $R_{12}$ and $R_{13}$ being as defined above for (I), with the limitation that at least one of the substituents $R_{10}$, $R_{11}$, $R_{12}$ and $R_{13}$ is other than hydrogen;

as well as the salts and solvates thereof.

the compounds of formula:

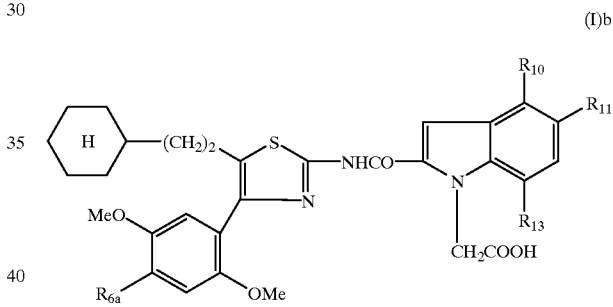

(I)b in which:

$R_{6a}$ is as defined above for (I)a;

$R_{10}$, $R_{11}$ and $R_{13}$ are as defined above for (I), with the limitation that one or two of the substituents $R_{10}$, $R_{11}$ and $R_{13}$ are other than hydrogen;

as well as the salts and solvates thereof.

the compounds of formula:

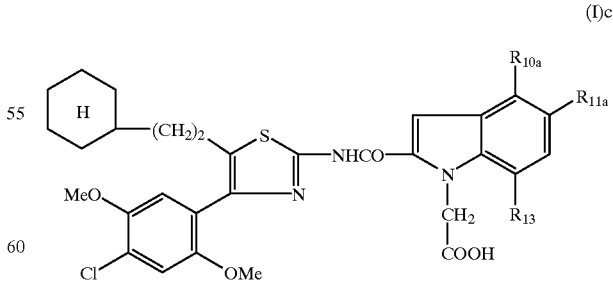

(I)c in which:

one or two of the substituents $R_{10a}$, $R_{11a}$ and $R_{13a}$ are a methyl, a methoxy, a chlorine, a fluorine or a trifluoromethyl, the other(s) being hydrogen, as well as the salts and solvates thereof.

Most particularly, the following compounds are preferred:

2-(4-(4-chloro-2,5-dimethoxyphenyl)-5-(2-cyclohexylethyl)thiazol-2-ylcarbamoyl)-5-methylindole-1-acetic acid;
2-(4-(4-chloro-2,5-dimethoxyphenyl)-5-(2-cyclohexylethyl)thiazol-2-ylcarbamoyl)-5,7-dimethylindole-1-acetic acid;
2-(4-(4-chloro-2,5-dimethoxyphenyl)-5-(2-cyclohexylethyl)thiazol-2-ylcarbamoyl)-4-methoxyindole-1-acetic acid;
2-(4-(4-chloro-2,5-dimethoxyphenyl)-5-(2-cyclohexylethyl)thiazol-2-ylcarbamoyl)-4-methylindole-1-acetic acid;
2-(4-(4-chloro-2,5-dimethoxyphenyl)-5-(2-cyclohexylethyl)thiazol-2-ylcarbamoyl)-4,5-dimethylindole-1-acetic acid;
2-(4-(4-chloro-2,5-dimethoxyphenyl)-5-(2-cyclohexylethyl)thiazol-2-ylcarbamoyl)-5-methoxyindole-1-acetic acid;
2-(4-(4-chloro-2,5-dimethoxyphenyl)-5-(2-cyclohexylethyl)thiazol-2-ylcarbamoyl)-5-chloroindole-1-acetic acid;
2-(4-(4-chloro-2,5-dimethoxyphenyl)-5-(2-cyclohexylethyl)thiazol-2-ylcarbamoyl)-4,5-dichioroindole-1-acetic acid;
2-(4-(4-chloro-2,5-dimethoxyphenyl)-5-(2-cyclohexylethyl)thiazol-2-ylcarbamoyl)-4,7-dimethylindole-1-acetic acid;
2-(4-(4-chloro-2,5-dimethoxyphenyl)-5-(2-cyclohexylethyl)thiazol-2-ylcarbamoyl)-4,5-dimethoxyindole-1-acetic acid;
2-(4-(4-chloro-2,5-dimethoxyphenyl)-5-(2-cyclohexylethyl)thiazol-2-ylcarbamoyl)-7-methoxyindole-1-acetic acid;
2-(4-(4-chloro-2,5-dimethoxyphenyl)-5-(2-cyclohexylethyl)thiazol-2-ylcarbamoyl)-7-methylindole-1-acetic acid;
2-(4-(4-chloro-2,5-dimethoxyphenyl)-5-(2-cyclohexylethyl)thiazol-2-ylcarbamoyl)-5,7-dichloroindole-1-acetic acid;
2-(4-(4-chloro-2,5-dimethoxyphenyl)-5-(2-cyclohexylethyl)thiazol-2-ylcarbamoyl)-4,7-dimethoxyindole-1-acetic acid;
2-(4-(4-chloro-2,5-dimethoxyphenyl)-5-(2-cyclohexylethyl)thiazol-2-ylcarbamoyl)-5-methoxy-7-methylindole-1-acetic acid;
2-(4-(4-chloro-2,5-dimethoxyphenyl)-5-(2-cyclohexylethyl)thiazol-2-ylcarbamoyl)-5-methyl-7-chloroindole-1-acetic acid;
2-(4-(4-chloro-2,5-dimethoxyphenyl)-5-(2-cyclohexylethyl)thiazol-2-ylcarbamoyl)-5-chloro-7-methylindole-1-acetic acid;
2-(4-(4-chloro-2,5-dimethoxyphenyl)-5-(2-cyclohexylethyl)thiazol-2-ylcarbamoyl)-5-chloro-7-fluoroindole-1-acetic acid;
2-(4-(4-chloro-2,5-dimethoxyphenyl)-5-(2-cyclohexylethyl)thiazol-2-ylcarbamoyl)-4-methyl-7-chloroindole-1-acetic acid;
2-(4-(4-chloro-2,5-dimethoxyphenyl)-5-(2-cyclohexylethyl)thiazol-2-ylcarbamoyl)-4-methyl-5-chloroindole-1-acetic acid;
2-(4-(4-chloro-2,5-dimethoxyphenyl)-5-(2-cyclohexylethyl)thiazol-2-ylcarbamoyl)-5-chloro-7-trifluoromethylindole-1-acetic acid;
2-(4-(4-chloro-2,5-dimethoxyphenyl)-5-(2-cyclohexylethyl)thiazol-2-ylcarbamoyl)-4-methoxy-7-methylindole-1-acetic acid;
as well as the salts and solvates thereof.

The following compounds are more particularly preferred:

2-(4-(4-chloro-2,5-dimethoxyphenyl)-5-(2-cyclohexylethyl)thiazol-2-ylcarbamoyl)-5-methylindole-1-acetic acid;
2-(4-(4-chloro-2,5-dimethoxyphenyl)-5-(2-cyclohexylethyl)thiazol-2-ylcarbamoyl)-5,7-dimethylindole-1-acetic acid;

as well as the salts and solvates thereof, in particular the sodium and potassium salts and the solvates thereof.

A second subject of the present invention is a process for the preparation of the compounds (I) according to the invention. This process is characterized in that it comprises the following steps:

a) coupling a substituted 2-aminothiazole of formula:

(II)

in which $R_1$ and $R_2$ are as defined above for (I), with an acid of formula $R'_3COOH$ (III) or alternatively with a functional substituted form of the said acid, in which $R'_3$ is $R_3$ or a substituted form of $R_3$ as defined above for (I), and in which the acid function of $R_3$ is protected;

b) where appropriate, converting the compound obtained, of formula (I'):

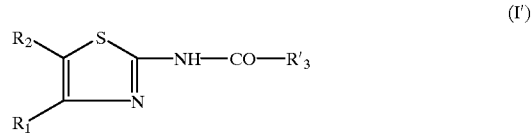

(I')

into a compound of formula (I) by deprotection of the protected acid function of the substituent of $R'_3$, and c) the compound of formula (I) thus obtained is isolated in its current form or in the form of one of the salts or solvates thereof.

Step a) of the process is generally carried out in basic medium. Functional substituted forms of the acid (III) which can be used are an activated acid, an anhydride, a mixed anhydride or an activated ester of the said carboxylic acid. An ester such as, for example, a $(C_1–C_4)$alkyl ester is used as protecting group for the acid function.

The mixed anhydrides can be prepared by reacting an alkyl chloroformate with the acid, in the presence of a base, generally a tertiary amine such as triethylamine; this reaction is usually carried out in a solvent such as dichloromethane, dichoroethane or chloroform.

The coupling of the aminothiazole (II) with the acid (III) in activated ester form, prepared for example by reacting 1-hydroxybenzotriazole with the acid in the presence of dicyclohexylcarbodiimide according to the procedure described in J. Am. Chem. Soc. 1971, 93, 6318–6319, or by reacting 1-benzotriazolyloxytris(dimethylamino) phosphonium hexafluorophosphate (BOP) according to the procedure described in Synthesis, 1976, 751–752, can be carried out in a solvent whose nature is selected depending on the solubility of the compounds and the type of activation of the acid function, preferably in the presence of a base, for example a tertiary amine such as triethylamine; the reaction is generally carried out at a temperature of between 0° C. and 3° C.

The compounds of formula (I) in which one (or more) substituents $R_{10}$, $R_{11}$, $R_{12}$ or $R_{13}$ is a hydroxyl are obtained from the compounds of formula (I) in which the substituent or (the said substituents) is an acetyloxy, the other substituents being identical, by hydrolysis in basic medium.

In the present description and in the claims, the following symbols and abbreviations are used.

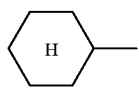

is a cyclohexyl.

DCM: dichloromethane
Et$_2$O: ether: diethyl ether
iso ether: diisopropyl ether
hydrochloric ether: ether saturated with hydrogen chloride gas
MeOH: methanol
EtOH: ethanol
iPrOH: isopropanol: 2-propanol
EtOAc: ethyl acetate
DMF: dimethylformamide
THF: tetrahydrofuran
DME: dimethoxyethane
DIPEA: diisopropylethylamine
DMAP: 4-dimethylaminopyridine
DBU: 1,8-diazabicyclo[5.4.0]undec-7-ene
PTT: phenyltrimethylammonium tribromide
TMEDA: tetramethylethylenediamine
NBS: N-bromosuccinimide
CDI: carbonyldiimidazole
Triton B: N-benzyltrimethylammonium hydroxide
AcOH: acetic acid
TFA: trifluoroacetic acid
Pd/C: palladium-on-charcoal
Ms: mesyl
Ts: tosyl
Triflic acid: trifluoromethanesulphonic acid
Boc: tert-butoxycarbonyl
Me, MeO: methyl, methoxy
Et: ethyl
Pr, iPr: propyl, isopropyl
Bu, iBu, tBu: butyl, isobutyl, tert-butyl
Bz: benzyl
NEt$_3$: triethylamine
BOP: 1-benzotriazolyloxytris(dimethylamino) phosphonium hexafluorophosphate
DCI: dicyclohexylcarbodiimide
pH2 buffer: sulphate buffer
silica H: 60 H silica gel sold by E. Merck (Darmstadt)
m.p.: melting point
RT: room temperature The aminothiazoles of formula (II) are prepared by known methods, such as those described in patent EP 518,731 and patent application EP 611,766.

In general, thiourea is reacted with a halo ketone of formula (IV) according to the following reaction scheme:

Scheme 1

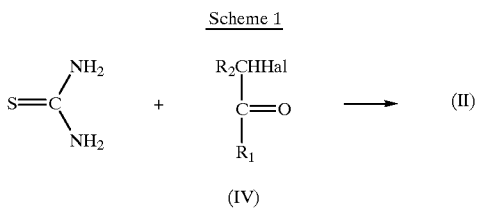

The substituents $R_1$ and $R_2$ of the compound (IV) have the same meanings as for the compound (I) and Hal is a halogen, preferably bromine or chlorine.

The halo ketones of formula (IV) can be prepared by processes whose principles are described in the literature. For example, the bromo ketones can be obtained by reacting bromine in acidic medium, cupric bromide or phenyltrimethylammonium tribromide (PTT) with a compound of formula:

$$R_2CH_2COR_1 \qquad (V)$$

in which $R_1$ and $R_2$ have the meanings given above for (I), in an organic solvent such as ethyl acetate, a chlorinated solvent or a mixture thereof.

The ketones (V) are generally prepared by Friedel-Crafts reaction in the presence of a Lewis acid such as AlCl$_3$ or TiCl$_4$, for example. Halo ketones of formula (IV) can also be prepared by Friedel-Crafts reaction with a suitable acid halide HalCOCHHalR$_2$ (VI) on a suitably substituted benzene ($R_1H=C_6H_2(OMe)R_4R_5R_6$), for example according to Chem. Pharm. Bull., 1991, 39 (9), 2400–2407.

An aminothiazole of formula (II) can also be prepared in a single step. starting with a substituted acetophenone of formula (V) by successively reacting bromine or PTT in a solvent such as dichloromethane or carbon tetrachloride, followed by thiourea, in an alcohol such as ethanol or methanol, for example.

The aminothiazoles of formula (II) can also be prepared using the Hoesch reaction (according to Dubois, Organic Reactions, 1945, 5, 387 or according to Satchell et al., The Chemistry of the Carbonyl Group, ed. S. Patai, Interscience, 1966, 1 (5), 233–302) followed by coupling with thiourea.

The acid halides of formula (VI) are prepared from the corresponding acid of formula $R_2CH_2COOH$ (VII) by standard methods, for example by reacting with thionyl chloride or oxalyl chloride.

The acids of formula (VII) are known or prepared by known methods.

In particular, triethyl phosphonocrotonate can be used and the process can be performed according to the reaction scheme below in order to prepare the compounds of formula R'$_2$—(CH$_2$)$_3$—CO$_2$H in which R'$_2$ is a (C$_5$–C$_7$)cycloalkyl:

Scheme 2

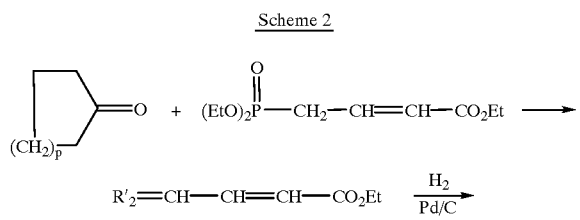

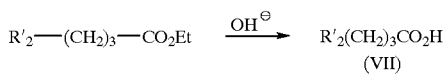

p=1, 2 or 3.

An acid of formula $R'_2$—S—$(CH_2)_2$—COOH in which $R'_2$ is a $(C_5$–$C_7)$cycloalkyl can be prepared from a compound of formula $R'_2SH$ by reaction with caesium hydroxide and then a haloalkanoic acid ester according to the reaction scheme below:

Scheme 3

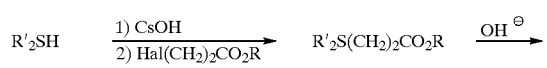

with R=$(C_1$–$C_4)$alkyl.

In certain cases, for example in order to prepare an aminothiazole of formula (II) in which $R_2$ is a group —S—$CH_2R'_2$, the method cited in S. P. Bruekelman et al., J. Chem. Soc. Perkin Trans I, 1984, 2801–2807, which is described in the scheme below, can be used:

Scheme 4

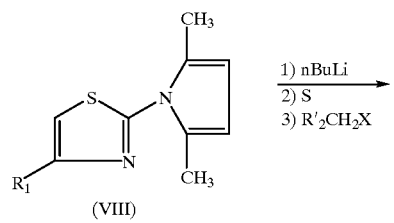

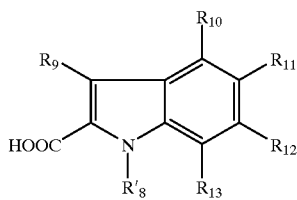

with X being a halogen, a methanesulphonate, a benzenesulphonate, a p-toluenesulphonate or a trifluoromethanesulphonate.

The compounds of formula:

(III)$_1$ in which $R_9$, $R_{10}$, $R_{11}$, $R_{12}$ and $R_{13}$ are as defined above for (I), and $R'_8$ is $R_8$ as defined for (I) or a precursor of $R_8$ in which the carboxylic acid function is esterified, are known or are prepared according to the methods described in EP 518,731 or EP 611,766 according to the scheme below:

Scheme 5

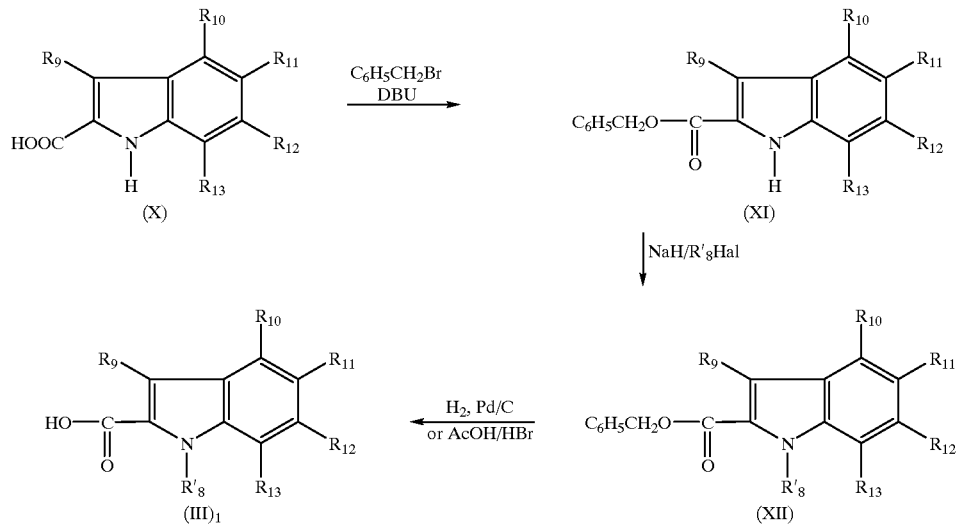

with Hal being a halogen.

In the final step, for debenzylation, either catalytic hydrogenation is used when none of the substituents $R_{10}$, $R_{11}$, $R_{12}$ or $R_{13}$ is a halogen, or a saturated solution of hydrobromic acid in acetic acid is used when $R'_8$ is protected with an alkyl other than tert-butyl.

More particularly, the compounds of formula:

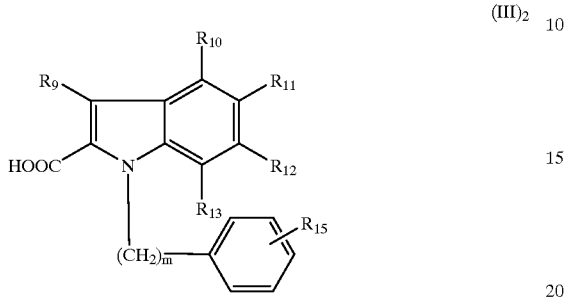

(III)$_2$ in which m, $R_9$, $R_{10}$, $R_{11}$, $R_{12}$, $R_{13}$ and $R_{15}$ are as defined above for (I), are obtained from an ester, for example the benzyl ester of 2-indolecarboxylic acid substituted according to the scheme below:

Scheme 6

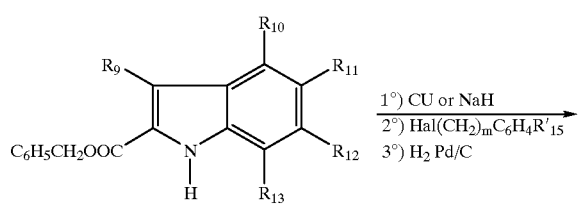

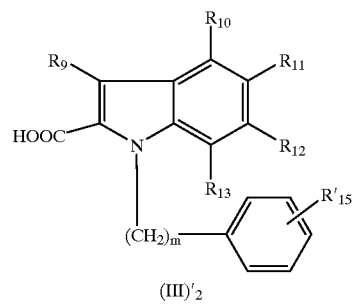

(III)'$_2$ $R'_{15}$ is $R_{15}$ or a group in which the carboxylic acid function is esterified.

Sodium hydride is reacted in order to obtain a compound of formula (III)'$_2$ in which m=1, or copper is reacted in order to obtain a compound of formula (III)'$_2$ in which m=0; next, a halobenzoic acid ester (or a halomethylbenzoic acid ester) is reacted and, lastly, catalytic hydrogenation is carried out.

The starting indoles are commercially available or are prepared according to an adaptation of the processes described in the literature, for example according to L. Henn et al., J. Chem. Soc. Perkin Trans. 1, 1984, 9189 according to Scheme 7 below:

Scheme 7

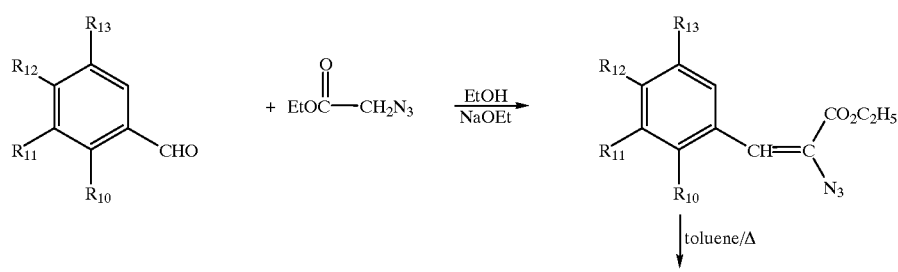

or alternatively, for example, according to the Fischer synthesis (V. Prelog et al., Helv. Chim. Acta, 1948, 31, 1178) according to Scheme 8 below:
Scheme 8
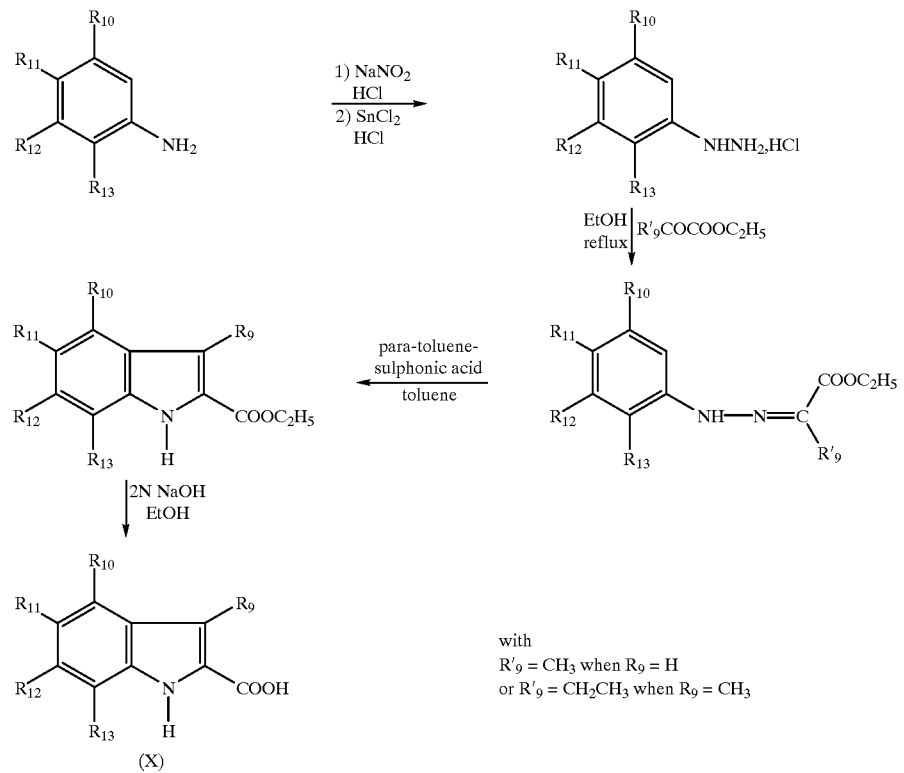
with
R′$_9$ = CH$_3$ when R$_9$ = H
or R′$_9$ = CH$_2$CH$_3$ when R$_9$ = CH$_3$
or alternatively according to the Japp-Klingemann synthesis (H. Ishii et al., J. Chem. Soc. Perkin. Trans. 1, 1989, 2407) according to Scheme 9 below:
Scheme 9
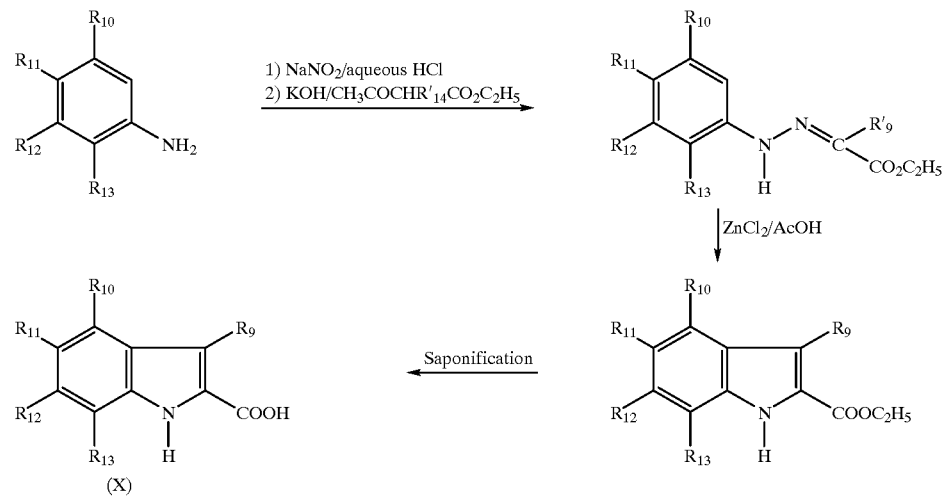

According to the present invention, a novel process has been found which is useful for the preparation of 2-indolecarboxylic acids or 1H-pyrrolopyridine-2-carboxylic acids.

Thus, a subject of the present invention is also a process for the synthesis of the compounds of formula:

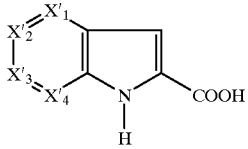

(XVIII)

in which $X'_1$, $X'_2$, $X'_3$ and $X'_4$ are a CH group optionally substituted with a methyl group or one of the groups $X'_1$, $X'_2$, $X'_3$ or $X'_4$ is N, and the others are $CR_{14}$ with $R_{14}$ being hydrogen or a methoxy, these compounds being useful as intermediates for the preparation of compounds of formula (I).

This process is characterized in that it comprises the steps consisting in:

a) protecting the amine function of a compound of formula:

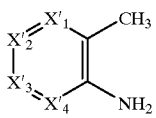

(XIX)

by treating it with di-tert-butyl dicarbonate ((Boc)$_2$O);

b) treating the compound thus obtained, of formula:

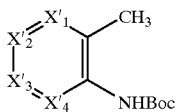

(XX)

with an alkyllithium such as n-BuLi or sec-BuLi;

c) coupling the lithiated derivative thus formed with an oxalic ester such as ethyl oxalate or benzyl oxalate;

d) cyclizing in acidic medium;

e) saponifying the ester thus obtained, of formula:

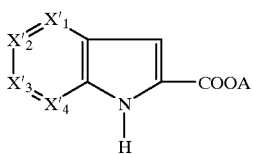

(XXI)

in which A is an ethyl, or hydrogenolysing the ester thus obtained, of formula (XXI) in which A is a benzyl.

In step b), the lithiation is carried out according to D. Hands et al., Synthesis, 1996, 877–882 or R. D. Clark et al., Synthesis, 1991, 871–878.

The variant which consists in using, in step c), benzyl oxalate instead of ethyl oxalate avoids the intermediate saponification and esterification steps.

Step d) can be carried out in the presence of trifluoroacetic acid or by heating in the presence of 6N HCl.

The process claimed can be applied effectively to the preparation of the 2-indolecarboxylic acids of formula Xb:

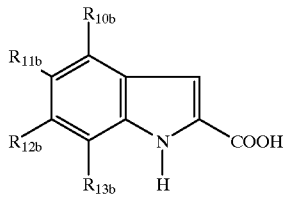

(X)$_b$ in which $R_{10b}$, $R_{11b}$, $R_{12b}$ and $R_{13b}$ are, independently of each other, hydrogen or methyl, starting with an orth-omethylaniline.

In this specific case, the process claimed comprises the steps consisting in a) protecting the amine function of an ortho-methylaniline of formula:

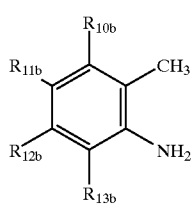

(XI)$_b$ by treating it with di-tert-butyl dicarbonate (Boc)$_2$O;

b) treating the compound thus obtained, of formula:

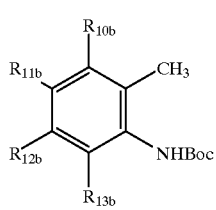

(XII)$_b$ with an alkyllithium such as n-BuLi or sec-BuLi;

c) coupling the lithiated derivative thus formed with an oxalic ester such as ethyl oxalate or benzyl oxalate;

d) cyclizing in acidic medium;

e) saponifying the ester thus obtained, of formula:

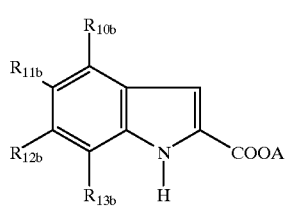

(XIII)$_b$ in which A is an ethyl, or hydrogenolysing the ester thus obtained, of formula (XIII)$_b$ in which A is a benzyl.

In the specific cases in which:

either $R_{13b}=R_{12b}=CH_3$ and $R_{10b}=R_{11b}=H$, or $R_{13b}=R_{10b}=CH_3$ and $R_{11b}=R_{12b}=H$, 2 esters of formula:

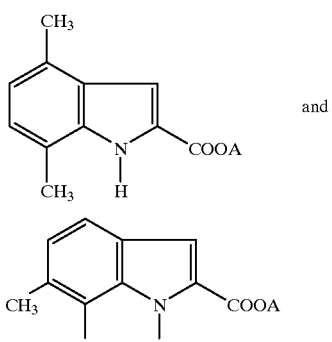

and are obtained after step e)

These compounds can be separated by known methods of organic chemistry, for example by chromatography.

The process claimed is also particularly advantageous for obtaining the compounds of formula:

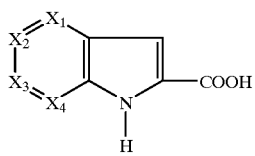

and the substituted 2-pyrrolopyridinecarboxylic acids of formula $(III)_3$ $(III)_3$

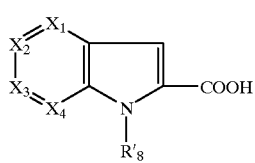

in which $X_1$, $X_2$, $X_3$ and $X_4$ have the definitions given above for (I) and $R'_8$ is $R_8$ as defined above for (I), or a precursor of $R_8$, starting with an ortho-methylaminopyridine.

For example, a substituted 1H-pyrrolo[3,2-b]pyridine-2-carboxylic acid can be prepared according to the reaction scheme below:

Scheme 10

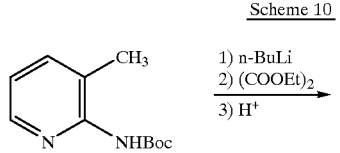

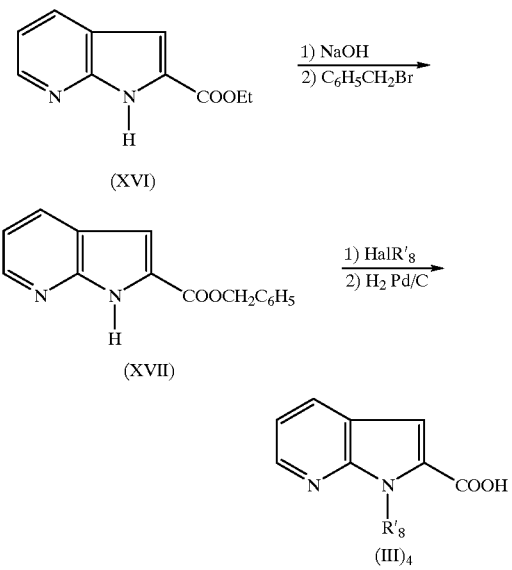

Scheme 11

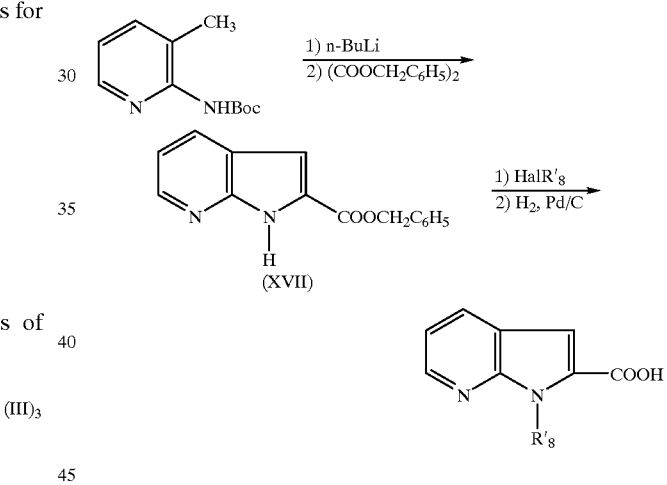

When the starting pyridines have one or more methoxy substituents, the reactions described in Schemes 10 and 11 make it possible to obtain compounds of formula $(III)_3$ substituted on the pyridine ring with one or more methoxy groups.

The substituted pyrrolopyridine carboxylic acids of formula:

$(III)_3$

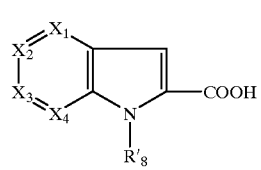

in which $X_1$, $X_2$, $X_3$ and $X_4$ have the definitions given above for (I) and $R'_8$ is $R_8$ as defined above for (I) or a precursor of $R_8$ in which the carboxylic acid function is esterified, can also be prepared by known methods.

The substituted 1H-pyrrolo[2,3-c]pyridine-2-carboxylic acids and the substituted 1H-pyrrolo[3,2-c]pyridine-2- carboxylic acids can be prepared from the corresponding methylpyridines nitrated in the position ortho to the methyl, according to a modification of the Reissert method, as described, for example, in B. Frydman et al., J. Org. Chem. 1968, 3762–3766 or M. H. Fisher et al., J. Het. Chem., 1969, 775–776.

For example, a substituted 1H-pyrrolo[3,2-b]pyridine-2-carboxylic acid can be prepared by working according to the reaction scheme below:

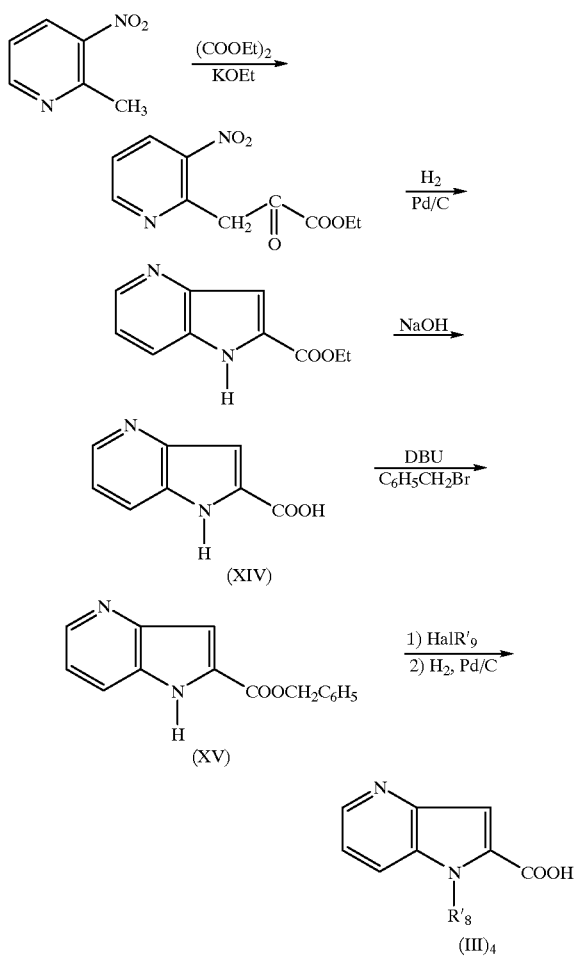

According to the invention, the compounds of formula (I) also comprise those in which one or more hydrogen, carbon or halogen, in particular chlorine or fluorine, atoms have been replaced by their radioactive isotope, for example tritium or carbon-14. Such labelled compounds are useful in research, metabolism or pharmacokinetic studies and in biochemical tests as labelled receptor ligands.

The compounds of formula (I) underwent studies of in vitro binding to the CCK-A and CCK-B receptors, using the method described in Eur. J. Pharmacol., 1993, 232, 13–19.

They have a high affinity for the CCK-A receptors (inhibitory concentration $IC_{50}$ of about $10^{-9}M$) and a markedly lower affinity for the CCK-B receptors, occasionally with a ratio at least equal to 100 between the 2 affinities. For example, the compound of Example 5 binds to the human CCK-A receptor with a high affinity ($IC_{50}$=0.56 nM), which is higher than that of CCK ($IC_{50}$=1.17 nM) and the affinity of this compound for the human CCK-B receptor is low ($IC_{50}$=162 nM).

The agonist activity of the compounds towards the CCK-A receptors was evaluated in vitro in 3T3 cells expressing the human CCK-A receptor, by measuring the mobilization of the intracellular calcium ($[Ca^{++}]_i$), according to a technique derived from that of Lignon MF et al., Eur. J. Pharmacol., 1993, 245, 241–245. The calcium concentration $[Ca^{++}]_i$ is evaluated with Fura-2 as fluorescent probe, by the double excitation wavelength method. The ratio of the fluorescence emitted at two wavelengths gives the concentration of $[Ca^{++}]_i$ after calibration (Grynkiewicz G. et al., J. Biol. Chem., 1985, 260, 3440–3450).

As with CCK, the compounds according to the invention increase the intracellular calcium concentration ($[Ca^{++}]_i$) with an $EC_{50}$ (effective concentration which induces 50% of the effect of CCK) of less than or equal to 100 nM. They thus behave as CCK-A receptor agonists. In this respect, they are of higher performance than the compounds described in EP 611,766 which show no agonist property towards $[Ca^{++}]_i$ at this concentration of 100 nM. By way of example, the compound of Example 5 stimulates the increase in intracellular calcium concentration to the same level as CCK itself, and thus behaves as a total agonist. Its effect is exerted at a very low dose ($EC_{50}$=1.27 nM), as with CCK itself ($EC_{50}$=1.28 nM).

A study of the agonist effect of the compounds on gastric drainage was carried out as follows. Female Swiss albino CD1 mice (20–25 g) are placed on a solid fast for 18 hours. On the day of the experiment, the products (as a suspension in 1% carboxymethyl cellulose solution or in 0.6% methylcellulose solution) or the corresponding vehicle are administered intraperitoneally, 30 minutes before administering a charcoal meal (0.3 ml per mouse of a suspension in water of 10% charcoal powder, 5% gum arabic and 1% carboxymethyl cellulose or 0.6% methyl cellulose). The mice are sacrificed five minutes later by cervical dislocation, and gastric drainage is defined as the presence of charcoal in the intestine beyond the pyloric sphincter (Eur. J. Pharmacol., 1993, 232, 13–19).

The compounds of formula (I) block gastric drainage, like CCK itself, and thus behave as CCK-A receptor agonists. Some of the compounds according to the invention have $ED_{50}$ (the effective dose which induces 50% of the effect of CCK) values of less than or equal to 0.1 mg/kg intraperitoneally.

Under these same conditions, the compounds described in EP 611,766 show no significant agonist property towards gastric drainage at a dose of 0.1 mg/kg and have $ED_{50}$ values of greater than 1 mg/kg intraperitoneally. By way of example, the compound of Example 5 is very active in vitro or it completely inhibits gastric drainage with an $ED_{50}$ of 1.9 μg/kg intraperitoneally.

Consequently, the compounds of formula (I) are of particularly high performance, as CCK-A receptor agonists of CCK, for the preparation of medicines intended to combat diseases whose treatment requires stimulation of the cholecystokinin CCK-A receptors.

More particularly, the compounds of formula (I) are used for the manufacture of medicines intended for the treatment of certain diseases of the gastrointestinal system (prevention of gallstones, irritable bowel syndrome, etc.), feeding behaviour, obesity or associated pathologies such as diabetes and hypertension. The compounds of formula (I) induce a state of satiety and can thus be used to reduce feeding, to treat bulimia and obesity and to bring about weight loss.

The compounds (I) are also useful for the manufacture of medicines intended for the treatment of central nervous system disorders, in particular disorders of emotional and sexual behaviour and memory disorders, psychosis, and in particular schizophrenia, Parkinson's disease, dyskinesia such as tardive dyskinesia or facial dyskinesia after prolonged treatment with neuroleptic agents. They can also be used to treat appetite disorders, i.e. to regulate the desire for consumption, in particular the consumption of sugars, fat, alcohol or drugs and more generally of appetizing ingredients.

No sign of toxicity is observed with these compounds at pharmacologically active doses, and their harmlessness is thus compatible with their use as medicines for the treatment of the disorders and diseases mentioned above.

A subject of the present invention is also pharmaceutical compositions containing an effective dose of at least one compound according to the invention or of a pharmaceutically acceptable salt or solvate thereof, where appropriate as a mixture with suitable excipients.

The said excipients are chosen according to the pharmaceutical composition and the desired mode of administration.

In the pharmaceutical compositions of the present invention for oral, sublingual, subcutaneous, intramuscular, intravenous, topical, intratracheal, intranasal, transdermal, rectal or intraocular administration, the active principles of formula (I) above, or the optional salts thereof, can be administered in unit forms of administration, mixed with standard pharmaceutical supports, to animals and to humans for the prophylaxis or treatment of the abovementioned diseases and disorders. The appropriate unit forms of administration comprise oral forms such as tablets, gelatin capsules, powders, granules and oral suspensions and solutions, sublingual, buccal, intratracheal and intranasal forms of administration, subcutaneous, intramuscular or intravenous forms of administration and rectal forms of administration. The compounds according to the invention can be used in creams, ointments, lotions or eye drops for topical administration.

In order to obtain the desired prophylactic or therapeutic effect, the dose of active principle. can range between 0.01 and 50 mg per kg of body weight and per day.

Each unit dose can contain from 0.5 to 1000 mg, preferably from 1 to 500 mg, of active ingredients in combination with a pharmaceutical support. This unit dose can be administered 1 to 5 times per day so as to administer a daily dose of from 0.5 to 5000 mg, preferably from 1 to 2500 mg.

When a solid composition in tablet form is prepared, the main active ingredient is mixed with a pharmaceutical vehicle, such as gelatin, starch, lactose, magnesium stearate, talc, gum arabic or the like. The tablets can be coated with sucrose, a cellulose derivative or other suitable materials, or alternatively they can be treated such that they have a sustained or delayed activity and so that they release a predetermined amount of active principle continually.

A preparation in gelatin capsule form is obtained by mixing the active ingredient with a diluent and by pouring the mixture obtained into soft or hard gelatin capsules.

A composition in syrup or elixir form or for administration in the form of drops can contain the active ingredient together with a sweetener, preferably a calorie-free sweetener, methylparaben and propylparaben as antiseptic, as well as an agent to impart flavour and a suitable dye.

The water-dispersible powders or granules can contain the active ingredient mixed with dispersing agents or wetting agents, or suspension agents such as polyvinylpyrrolidone, as well as with sweeteners or flavour enhancers.

For rectal administration, use is made of suppositories which are prepared with binders that melt at the rectal temperature, for example cocoa butter or polyethylene glycols.

Aqueous suspensions, isotonic saline solutions or sterile, injectable solutions which contain pharmacologically compatible dispersing agents and/or wetting agents, for example propylene glycol or butylene glycol, are used for parenteral administration.

The active principle can also be formulated in the form of microcapsules, optionally with one or more supports or additives, or alternatively with matrices such as a polymer or a cyclodextrin (patch, sustained-release forms).

The compositions according to the invention can be used in the treatment or prevention of various complaints in which CCK is of therapeutic value.

The compositions of the present invention can contain, along with the products of formula (I) above or the pharmaceutically acceptable salts thereof, other active principles which can be used in the treatment of the diseases or disorders indicated above.

Advantageously, the pharmaceutical compositions of the present invention contain, as active principle, at least one compound of formula (I) above, or one of the pharmaceutically acceptable salts, solvates or hydrates thereof.

The examples featured below are given by way of non-limiting illustration of the present invention.

A—Preparation of the 2-Aminothiazoles of Formula:

(II)

in which $R_1$ and $R_2$ are as defined above for (I).

Preparation 1.1

2-Amino-5-cyclohexylethyl-4-(2,5-dimethoxy-4-methylphenyl)thiazole

A) 4-Cyclohexylbutyryl chloride 50 g of 4-cyclohexanebutyric acid are refluxed for 4 hours in 160 ml of thionyl chloride. After evaporation of the excess thionyl chloride, the expected product is distilled off. b.p.= 70–80° C. at 400 Pa.

B) 4-Cyclohexyl-1-(2,5-dimethoxy-4-methylphenyl)butan-1-one 9.4 g of the compound obtained in the above step and 6.66 g of $AlCl_3$ in 150 ml of $CCl_4$ are mixed together and 7.6 g of 2,5-dimethoxy-4-methylbenzene are added dropwise, at 4° C., and the temperature is then maintained between 5° C. and 10° C. for 3 hours. The reaction medium is hydrolysed with dilute ice-cold HCl solution and the organic phase is then separated out by settling and dried over $MgSO_4$. The solvent is evaporated off to give the expected product: m.p.=53.5–54.5° C.

C) 2-Amino-5-cyclohexylethyl-4-(2,5-dimethoxy-4-methylphenyl)thiazole

All of the compound obtained in the above step is brominated with 2.5 ml of bromine in $CCl_4$ at RT. The mixture is washed with water, dried over $MgSO_4$, the solvent is evaporated off and the residue is then taken up in 100 ml of ethanol and 8 g of thiourea. After refluxing for 3 hours, the solvent is evaporated off and the reaction medium is then taken up in saturated $Na_2CO_3$ solution. This mixture is extracted with EtOAc, dried over $MgSO_4$, the solvent is evaporated off and the residue is then chromatographed on a column of silica, eluting with DCM/EtOAc (70/30; v/v) to give 9.3 g of the expected compound: m.p.=112° C.

Preparation 1.2

2-Amino-4-(5-chloro-2,4-dimethoxyphenyl)-5-cyclohexylethylthiazole

A) 4-Cyclohexyl-1-(5-chloro-2,4-dimethoxyphenyl)butan-1-one 10 g of 2,4-dimethoxychlorobenzene and 10.93 g of 4-cyclohexanebutyryl chloride obtained in step 1 of Preparation 1.1 in 100 ml of $CCl_4$ are mixed together at 0° C. and 6.35 ml of $TiCl_4$ are added. After stirring for 2 hours at 0° C., the mixture is poured onto ice-cold 1N HCl solution and the organic phase is then separated out by settling and washed with 0.5N NaOH. After drying over $MgSO_4$ and evaporation of the solvent, 20 g of the expected product are obtained.

B) 2-Amino-4-(5-chloro-2,4-dimethoxyphenyl)-5-cyclohexylethylthiazole 20 g of the compound obtained in the above step in 200 ml of $CCl_4$ are treated with 3.15 g of bromine in 20 ml of $CCl_4$, the mixture is washed with water and the organic phase is separated out, dried over $MgSO_4$ and then evaporated. The residue is taken up in ethanol and then refluxed for 3 hours in the presence of 7 g of thiourea. After evaporation of the solvent, the residue is taken up in EtOAc and then washed with saturated $Na_2CO_3$ solution and dried over $MgSO_4$. After evaporation of the solvent and trituration from a heptane/ether mixture (50/50; v/v), 12.55 g of the expected compound are obtained: m.p.=113° C.

Prepatation 1.3

2-Amino-5-cyclohexylethyl-4-(2,4-dimethoxyphenyl)thiazole

A) 4-Cyclohexyl-1-(2,4-dimethoxyphenyl)butan-1-one 3.53 g of $AlCl_3$ and 5 g of 4-cyclohexanebutyryl chloride in 100 ml of $CCl_4$ are mixed together and 5 g of 1,3-dimethoxybenzene are added dropwise, at 0° C. After stirring for 3 hours at 0° C., the entire mixture is poured onto dilute ice-cold HCl solution. The organic phase is separated out by settling and is then washed with 0.5N NaOH. After drying over $MgSO_4$ and evaporation of the solvent, the residue is chromatographed on a column of silica H, eluting with toluene, to give 4.5 g of the expected compound in the form of an oil.

B) 2-Amino-5-cyclohexylethyl-4-(2,4-dimethoxyphenyl)thiazole 4.44 g of the product obtained in the above step are placed in 50 ml of THF and a solution of 5.75 g of phenyltrimethylammonium tribromide (PTT) in 50 ml of THF is added dropwise. After stirring for 15 minutes at 0° C., this mixture is poured onto a mixture of water and DCM and is then extracted with the DCM. After drying over $MgSO_4$, the organic phase is evaporated and the residue is taken up in 100 ml of ethanol and then refluxed for 4 hours in the presence of 6 g of thiourea. After evaporation of the solvent, the residue is taken up in EtOAc and washed successively with $Na_2CO_3$ solution and then with water. The organic phase is dried over $MgSO_4$ and evaporated. The residue is triturated from an ether/heptane mixture (50/50; v/v) to give 4.18 g of the expected compound: m.p.=122° C.

Preparation 1.4

2-Amino-4-(4-chloro-2,5-dimethoxyphenyl)-5-cyclohexylethylthiazole

A) 4-Cyclohexyl-1-(2,5-dimethoxy-4-chlorophenyl)butan1-one 3.77 g of 4-cyclohexanebutyryl chloride dissolved in 10 ml of $CCl_4$ are added to a suspension of 2.8 g of $AlCl_3$ in 20 ml of $CCl_4$ at +4° C. under nitrogen. 5.2 g of 2,5-dimethoxychlorobenzene in 10 ml of $CCl_4$ are added dropwise and the mixture is then left stirring for 3 hours at RT. The reaction medium is hydrolysed with dilute HCl solution, the phases are then separated by settling and the organic phase is extracted with DCM. After drying over $MgSO_4$, the solution is evaporated and the residue is then purified by chromatography on silica, eluting with a heptane/DCM mixture (60/40; v/v) and then with pure DCM. 3.37 g of the expected compound are obtained: m.p.=80–81° C.

B) 2-Amino-4-(4-chloro-2,5-dimethoxyphenyl)-5-cyclohexylethylthiazole

All of the product obtained in the above step is dissolved in 50 ml of DCM. 1.66 g of bromine dissolved in 10 ml of DCM are added at RT and the organic phase is then washed with water and dried over $MgSO_4$. After evaporation, the residue is taken up in 30 ml of ethanol, 1.6 g of thiourea are added and the mixture is then refluxed overnight. The ethanol is evaporated off and the residue is then taken up in aqueous 50% $Na_2CO_3$ solution and DCM. After stirring for 1 hour, the phases are separated by settling, the aqueous phase is extracted with DCM and the combined organic phases are then dried over $Na_2SO_4$ and the solvent is evaporated off. Heptane is added and the product crystallizes on trituration. The product is filtered off and dried to give 3.42 g of the expected compound: m.p.=110–111° C.

Preparation 1.5

2-Amino-5-cyclohexylethyl-4-(5-ethoxy-2-methoxy-4-methylphenyl)thiazole

A) 4-Cyclohexyl-1-(2,5-diethoxy-4-methylphenyl)butan-1-one 4 g of 4-cyclohexylbutyryl chloride dissolved in 10 ml of $CCl_4$ are added to a suspension of 2.9 g of $AlCl_3$ in 40 ml of $CCl_4$ at +4° C. 4.2 g of 2,5-diethoxytoluene in 20 ml of $CCl_4$ are added dropwise. After 4 hours at +4° C., the reaction medium is poured into dilute ice-cold HCl solution. DCM is added, the phases are separated out by settling and the organic phase is then dried over $MgSO_4$. After evaporation of the solvent, the product is purified by chromatography on silica H, eluting with toluene. 5.33 g of the expected compound are obtained: m.p.=49–50° C.

B) 4-Cyclohexyl-1-(5-ethoxy-2-hydroxy-4-methylphenyl)butan-1-one

A solution of 5.33 g of the product of the above step in 80 ml of anhydrous DCM cooled to −5° C. is treated with 16 ml of 1M boron trichloride solution. The reaction medium is stirred for 5 minutes at −5° C. and is poured onto dilute ice-cold HCl solution. After stirring for 30 minutes, the phases are separated out by settling. The organic phase is dried over $MgSO_4$ and evaporated. The product is purified by chromatography on silica, eluting with DCM/heptane (50/50; v/v). 3.88 g of the expected compound are obtained in the form of a pale yellow solid: m.p.=48–49° C.

C) 4-Cyclohexyl-1-(5-ethoxy-2-methoxy-4-methylphenyl)butan-1-one 2 g of the product of the above step and 2 g of aqueous 50% caesium hydroxide solution are mixed together in 50 ml of MeOH. After evaporation, the residue is taken up in isopropanol and evaporated to dryness. The yellow solid obtained is dissolved in 10 ml of DMF and 5 ml of methyl iodide are added. After heating for 2 hours at 80° C., the DMF is evaporated off and the residue is taken up in water. The compound is extracted with DCM, The organic phase is dried over MgSO$_4$ and evaporated. The residue is purified by chromatography on silica, eluting with DCM; 2.12 g of the expected compound are obtained: m.p.=37–38° C.

D) 2-Amino-5-cyclohexylethyl-4-(5-ethoxy-2-methoxy-4-methylphenyl)thiazole

A solution of 2.5 g of PTT in 20 ml of THF is added dropwise to a solution, cooled to +4° C., of 2.12 g of the product of the above step in 30 ml of THF. The reaction medium is stirred for 15 minutes at +4° C. and is then poured onto ice-cold water. The aqueous phase is extracted 3 times with 100 ml of DCM. The organic phases are combined and dried over MgSO$_4$ and then evaporated. The residue is taken up in 30 ml of ethanol and 1.1 g of thiourea are added. After refluxing for 3 hours and cooling, the ethanol is evaporated off and the oil obtained is taken up in 5% Na$_2$CO$_3$ solution. This mixture is extracted twice with DCM. The DCM phases are dried over MgSO$_4$ and evaporated. The residue crystallizes by trituration from heptane. After filtration and drying, 2.19 g of the expected compound are obtained: m.p.=96–97° C.

Preparation 1.6

2-Amino-5-cyclohexylthiomethyl-4-(2,5-dimethoxy-4-methylphenyl)thiazole

A) Ethyl 3-cyclohexylthiopropionate 25 g of cyclohexyl mercaptan and 64.66 g of aqueous 50% caesium hydroxide are dissolved in 200 ml of methanol. After evaporation to dryness, 2 azeotropic distillations with iPrOH are carried out, the dry product is then taken up in 100 ml of DMF, 40 g of ethyl 3-bromo-propionate are added and the mixture is heated for 2 hours at 80° C. After cooling, the solid formed is filtered off and then washed with the minimum amount of DMF. The DMF is evaporated off and the residue is taken up in ether, washed with water, with 5% Na$_2$CO$_3$ solution and then with water. This solution is dried over Na$_2$SO$_4$ and then evaporated. The residue is chromatographed on silica, eluting with a DCM/heptane mixture (50/50; v/v) to give 38.86 g of the expected compound in liquid form.

B) 3-Cyclohexylthiopropionic acid

All of the product of the above step is placed in 200 ml of methanol and a solution of 17 g of NaOH in 50 ml of water is added. After leaving overnight at RT, the methanol is evaporated off, the residue is taken up in water and the aqueous phase is then extracted with ether. The ether phases are discarded, the aqueous phase is acidified to pH 2 by addition of concentrated HCl and is then extracted 3 times with DCM, and the extracts are dried over MgSO$_4$ and evaporated to give 31.1 g of the expected product in oily form.

C) 3-Cyclohexylthiopropionyl chloride 4 g of the compound of the above step are dissolved in 40 ml of DCM and treated with 3.5 g of oxalyl chloride; 3 drops of DMF are added and the mixture is then left stirring for 30 minutes and is evaporated to dryness. The product is used without further purification in the following step.

D) 2-Amino-5-cyclohexylthiomethyl-4-(2,5-dimethoxy-4-methylphenyl)thiazole

The process is then performed according to the procedures described above: the product is treated with 2,5-dimethoxytoluene in the presence of TiCl$_4$, then bromination of the ketone is carried out by reaction with PTT and the resulting product is reacted with thiourea to give 4.13 g of the expected product: m.p.=143–144° C.

Preparation 1.7

2-Amino-5-cyclohexylmethylthio-4-(2,5-dimethoxy-4-methylphenyl)thiazole

A) 1-(2,5-Dimethoxy-4-methylphenyl)ethan-1-one

A suspension of 17.52 g of aluminium chloride in a mixture of 100 ml of CCl$_4$ and 100 ml of DCM is cooled to +4° C. under nitrogen, and 10.4 g of acetyl chloride are added dropwise, followed by a solution of 20 g of 2,5-dimethoxytoluene in 20 ml of DCM. After stirring for 4 hours at +4° C., the reaction medium is poured onto ice to which a few ml of concentrated HCl have been added and the mixture is left stirring for 30 minutes. The phases are separated by settling, the aqueous phase is extracted with DCM and the combined organic phases are washed with aqueous 5% NaCO$_3$ solution, dried over MgSO$_4$ and evaporated. The product crystallizes, and is triturated from 150 ml of heptane, filtered off and then washed with heptane to give 21.03 g of the expected compound: m.p.=75–77° C.

B) 2-Amino-4-(2,5-dimethoxy-4-methylphenyl)thiazole

A solution of 21.03 g of the compound of the above step in 300 ml of DCM is treated dropwise with a solution of 17.35 g of bromine in 70 ml of DCM. After separation of the phases by settling, the organic phase is washed with water, dried over MgSO$_4$ and then evaporated. The residue is taken up in 200 ml of absolute ethanol, 15.2 g of thiourea are then added and the mixture is refluxed overnight. The resulting mixture is cooled on an ice bath, the crystals formed are filtered off, they are then taken up in aqueous 5% Na$_2$CO$_3$ solution which is then extracted with EtOAc. The phases are separated by settling and the organic phase is dried over Na$_2$SO$_4$ and then evaporated. The residue is triturated from heptane and is then filtered to give 17.74 g of the expected compound in crystalline form: m.p.=191–192° C.

C) 4-(2,5-Dimethoxy-4-methylphenyl)-2-(2,5-dimethylpyrrol-1-yl)thiazole 17.74 g of the compound of the above step, 20.3 g of 2,5-hexanedione and 8.51 g of acetic acid are dissolved in 300 ml of benzene. After azeotropic distillation for 24 hours, the reaction medium is poured into water and then neutralized with aqueous 5% Na$_2$CO$_3$ solution. The phases are separated by settling and the aqueous phase is then extracted with EtOAc. The combined organic phases are dried over Na$_2$SO$_4$ and then evaporated. The residue is chromatographed on silica, eluting with DCM, to give 19.46 g of the expected compound, which crystallizes from heptane: m.p.= 92–93° C.

D) 5-(Cyclohexylmethylthio)-4-(2,5-dimethoxy-4-methylphenyl)-2-(2,5-dimethylpyrrol-1-yl)thiazole A solution of 3.28 g of the compound of the above step in 80 ml of anhydrous THF is cooled to −30° C. and is then treated with 8 ml of 1.6M n-butyllithium in hexane. After 30 minutes at −30° C., 650 mg of sulphur flowers are added. The mixture is allowed to warm to RT, 3.4 g of cyclohexylmethanol tosylate dissolved in 10 ml of anhydrous THF are then added and the mixture is left stirring for 2 hours at RT. The reaction medium is poured into water and then extracted with ether, and the extracts are dried over Na$_2$SO$_4$ and evaporated. The residue is chromatographed on silica H, eluting with toluene. 1.1 g of the expected compound are obtained: m.p. 117–118° C.

E) 2-Amino-5-cyclohexylmethylthio-4-(2,5-dimethoxy-4-methylphenyl)thiazole

A mixture containing 1.1 g of the compound of the above step, 30 ml of ethanol, 4.5 ml of water and 3.7 g of hydroxylamine hydrochloride is refluxed for 36 hours. After evaporation, the medium is taken up in aqueous 5% Na$_2$CO$_3$ solution and then extracted with DCM, the extracts are dried over MgSO$_4$ and evaporated and the residue is then chromatographed on silica, eluting with DCM/EtOAc (70/30; v/v). 0.78 g of the expected compound is obtained: m.p.= 111–112° C.

Preparation 1.8

2-Amino-5-cycloheptylethyl-4-(2,5-dimethoxy-4-methylphenyl)thiazole

A) Ethyl 4-cycloheptylidene-2-butenoate 6.7 ml of ethyl 4-(diethoxyphosphoryl)-2-butenoate are dissolved in 7 ml of dimethoxyethane and the solution is then poured onto 1.3 g of 60% sodium hydride in 40 ml of dimethoxyethane. After stirring for 45 minutes, the mixture is cooled to 10° C., 3.2 ml of cycloheptanone are then added dropwise and the mixture is allowed to return to RT. After stirring for 4 hours, the mixture is poured onto cold water and then extracted with ether, and the extracts are dried and evaporated. The residue is chromatographed on silica, eluting with DCM. 1.9 g of the expected compound are obtained.

B) Ethyl 4-cycloheptylbutanoate

All of the compound of the above step is hydrogenated at room temperature and at atmospheric pressure in 20 ml of EtOH in the presence of 190 mg of 10% Pd/C 1.9 g of the expected compound are obtained.

C) 4-Cycloheptylbutanoic acid 1.9 g of the compound of the above step and 755 mg of sodium hydroxide are placed in 20 ml of MeOH and 5 ml of water, and the mixture is left stirring at RT for 24 hours. It is dried under vacuum to give 1.5 g of the expected compound.

D) 4-Cycloheptyl-(2,5-dimethoxy-4-methylphenyl)butan-1-one 1.5 g of the compound of the above step and 1 drop of DMF in 20 ml of DCM are cooled to 0° C., 0.71 ml of oxalyl chloride is added and the mixture is then allowed to return to RT. After stirring for 3 hours, 1.2 g of 2,5-dimethoxytoluene cooled to 4° C. are added, followed by portionwise addition of 1.2 g of AlCl$_3$. The mixture is left stirring for one and a half hours at +4° C. and then for 2 hours at RT. The reaction medium is poured into dilute HCl solution, the phases are then separated by settling and the aqueous phase is extracted with ether. The organic phases are combined, washed with 1N NaOH and then concentrated. The residue is purified by chromatography on silica, eluting with EtOAc/pentane (30/70; v/v) and 2.19 g of the expected compound are obtained.

E) 2-Amino-5-cycloheptylethyl-4-(2,5-dimethoxy-4-methylphenyl)thiazole 2.1 g of the compound of the above step are dissolved in 25 ml of THF and 2.47 g of PTT are added over 5 minutes. After stirring for 5 hours, the precipitate is filtered offhand washed with THF, the organic phase is then concentrated, the residue is taken up in 30 ml of EtOH, 0.5 g of thiourea is then added and this mixture is refluxed for 48 hours. The reaction medium is concentrated, the residue is taken up in 10% Na$_2$CO$_3$ solution and extracted with ether, and the organic phase is then washed, dried and concentrated. The residue is chromatographed on silica, eluting with EtOAc/pentane (70/30; v/v).

Preparation 1.9

2-Amino-5-((4,4-dimethylcyclohexyl)ethyl)-4-(2,5-dimethoxy-4-methylphenyl)thiazole A) 4,4-Dimethylcyclohexanone 6.7 g of 4,4-dimethyl-2-cyclohexen-1-one and 2 g of 10% Pd/C are added to 65 ml of EtOAc and the mixture is hydrogenated at RT under atmospheric pressure until the theoretical volume of hydrogen has been absorbed. The catalyst is filtered off and the filtrate is then concentrated to give 6.3 g of the expected product.

B) 2-Amino-5-[(4,4-dimethylcyclohexyl)ethyl]-4-(2,5-dimethoxy-4-methylphenyl)thiazole The process is then performed according to the procedure described in the above preparation, successively carrying out the steps A), B), C), D) and E) to give the expected product: m.p.=136–138° C.

Preparation 1.10

2-Amino-5-cyclopentylethyl-4-(2,5-dimethoxy-4-methylphenyl)thiazole

The process is performed according to the procedure described in the above two preparations, to give the expected compound: m.p.=80° C.

Preparation 1.11

2-Amino-5-cyclohexylethyl-4-(2,5-dimethoxy-4-ethylphenyl)thiazole

A) 1-(2,5-Dimethoxyphenyl)ethan-1-one 19.3 g of AlCl$_3$ are placed in 200 ml of CCl$_4$ at +5° C. under nitrogen and 11.36 g of acetyl chloride are added, followed by portionwise addition of 20 g of 1,4-dimethoxybenzene. After stirring for 3 hours at +5° C., the mixture is poured into dilute ice-cold HCl solution. The organic phase is separated out and dried over MgSO$_4$ and evaporated, and the residue is then chromatographed on silica, eluting with a DCM/heptane mixture (50/50; v/v) to give 24.71 g of the expected product.

B) 1,4-Dimethoxy-2-ethylbenzene

A mixture of 300 g of zinc powder and 40 g of mercuric chloride is prepared and is added to a solution of 24 g of the compound of the above step in 400 ml of benzene and 100 ml of concentrated HCl at 80° C. After stirring for 2 hours at 80° C., the mixture is filtered, the organic phase is then separated out, dried over MgSO$_4$ and evaporated and the residue is chromatographed on silica, eluting with a DCM/heptane mixture (50/50; v/v) to give 8.6 g of the expected product.

C) 2-Amino-5-cyclohexylethyl-4-(2,5-dimethoxy-4-ethylphenyl)thiazole

The process is then performed according to the procedure described in Preparation 1.3, to give the expected product: m.p.=88° C.

Preparation 1.12

2-Amino-5-cyclopentylmethylthio-4-(2,5-dimethoxy-4-methylphenyl)thiazole

A) 5-(Cyclopentylmethylthio)-2-(2,5-dimethylpyrrol-1-yl)-4-(2,5-dimethoxy-4-methylphenyl)thiazole A solution of 3.28. g of 4-(2,5-dimethoxy-4-methylphenyl)-2-(2,5-dimethylpyrrol-1-yl)thiazole as obtained in step C of Preparation 1.7, in 80 ml of THF, is prepared and this solution is cooled to –30° C. 8 ml of 1.6M n-butyllithium in hexane, in 10 ml of THF, are added dropwise and the mixture is left stirring for 30 minutes, allowing the temperature to return to 0° C. The mixture is cooled to –30° C. and 0.65 g of sulphur flowers is added. The temperature is allowed to return to 0° C. and 3.5 g of cyclopentylmethyl p-toluenesulphonate in 3 ml of THF are added. After stirring for 2 hours at RT, the mixture is poured into ice-cold water and extracted with ether, and the extracts are then dried over Na$_2$SO$_4$ and evaporated. The residue is chromatographed on silica H, eluting with toluene, to give 0.47 g of the expected product: m.p.=107.5–108.5° C.

B) 2-Amino-5-cyclopentylmethylthio-4-(2,5-dimethoxy-4-methylphenyl)thiazole 0.47 g of the compound of the above step and 2 g of hydroxylamine hydrochloride are mixed together in 20 ml of ethanol and 3 ml of water and refluxed for 48 hours. After evaporation of the solvent, the residue is taken up in 5% Na$_2$CO$_3$ solution and then extracted with DCM and the extracts are dried over MgSO$_4$ and evaporated. The residue is chromatographed on silica, eluting with DCM/EtOAc (80/20; v/v). 0.32 g of the expected compound is obtained: m.p.=88–89° C.

Preparation 1.13

2-Amino-5-cyclohexylethyl-4-(2,6-dimethoxy-4-methylphenyl)thiazole

A) 5-Cyclohexylethyl-2-(2,5-dimethylpyrrol-1-yl)-4-(2,6-dimethoxy-4-methylphenyl)thiazole 10 ml of 1.6M n-butyllithium in hexane are added, at –30° C., to 4.27 g of 2-(2,5-dimethylpyrrol-1-yl)-4-(2,6-dimethoxy-4-methylphenyl) thiazole and the mixture is left stirring for 30 minutes at –30° C. 4.2 g of cyclohexylethanol triflate are added at –45° C., the mixture is then warmed to 0° C., water is added, this mixture is extracted with Et$_2$O and the extracts are dried and evaporated. The gum formed is chromatographed on silica, eluting with cyclohexane/EtOAc (1/1; v/v). 0.52 g of the expected compound is obtained in the form of a colourless gum.

B) 2-Amino-5-cyclohexylethyl-4-(2,6-dimethoxy-4-methylphenyl)thiazole 0.4 g of the compound of the above step is refluxed overnight in 5 ml of EtOH and 2 ml of water in the presence of 0.93 g of hydroxylamine hydrochloride. The mixture is poured into saturated aqueous Na$_2$CO$_3$ solution and extracted with EtOAc, and the extracts are dried and then evaporated. The gum formed is chromatographed on silica, eluting with DCM/MeOH (100/3; v/v). 0.25 g of the expected compound is obtained in the form of a light brown oil.

Preparation 1.14

2-Amino-4-(2,5-dimethoxy-4-methylphenyl)-5-(5,5-dimethylhexyl)thiazole

A) (2,5-Dimethoxy-4-methylphenyl)-7,7-dimethyloctan-1-one 1 g of 7,7-dimethyloctanoic acid is dissolved in 20 ml of DCM cooled to 0° C., 0.57 ml of oxalyl chloride is added and the mixture is then left stirring for 1 hour at 0° C. and for 2 hours at RT. 0.93 ml of 2,5-dimethoxytoluene and one drop of DMF are added, the mixture is cooled to 0° C., 940 mg of AlCl$_3$ are then added and the mixture is left stirring for 1 hour at 0° C. and overnight at RT. It is poured into 10% HCl solution and extracted with ether, and the combined organic phases are then washed with 2N sodium hydroxide, dried and concentrated. The residue is chromatographed on silica, eluting with DCM/pentane (85/15; v/v) to give 1.05 g of the expected compound.

B) 2-Amino-4-(2,5-dimethoxy-4-methylphenyl)-5-(5,5-dimethylhexyl)thiazole 1.05 g of the compound of the above step are dissolved in 15 ml of THF, 1.29 g of PTT are then added and the mixture is left stirring for 4 hours at RT. The precipitate formed is removed and the filtrate is concentrated. The residue is taken up in 15 ml of ethanol, 260 mg of thiourea are then added and this mixture is refluxed overnight. The following day, the mixture is extracted with ether and the extracts are washed with water, with 1N NaOH solution, dried over Na$_2$SO$_4$ and concentrated. The residue is chromatographed on silica, eluting with EtOAc/pentane (75/25; v/v). 1.12 g of the expected compound are obtained.

By working according to the procedures described in Preparations 1.1 and 1.2, the compounds described in Table 1 below are prepared.

TABLE 1

(II)

[Structure: 2-amino thiazole with R2 at 5-position, R1 at 4-position]

| PREPARATIONS | R₁ | R₂ | m.p. ° C. |
|---|---|---|---|
| 1.15 | 2,5-dimethoxy-4-methylphenyl (with Me at 4, OMe at 2 and 5) | —(CH₂)₂—cyclohexyl | 120 |
| 1.16 | 4-chloro-2,5-dimethoxyphenyl | —CH₂—cyclohexyl | 136 |
| 1.17 | 2,5-dimethoxy-4-methylphenyl | n-hexyl | 115 |
| 1.18 | 4-chloro-2,5-dimethoxyphenyl | —S—CH₂—cyclohexyl | 133 |
| 1.19 | 2,4,5-trimethoxyphenyl | —(CH₂)₂—cyclohexyl | 151 |
| 1.20 | 2,4-dimethoxyphenyl | —(CH₂)₂—cyclohexyl | 127 |
| 1.21 | 4-fluoro-2,5-dimethoxyphenyl | —(CH₂)₂—cyclohexyl | 133 |

TABLE 1-continued
(II)
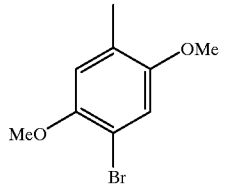
| PREPARATIONS | R₁ | R₂ | m.p. °C. |
|---|---|---|---|
| 1.22 | 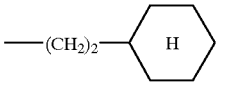 | —(CH₂)₂—C₆H₁₁ | 121 |
| 1.23 | 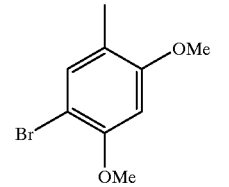 | —(CH₂)₂—C₆H₁₁ | 136 |
| 1.24 | 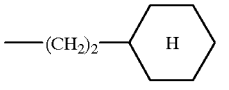 | —(CH₂)₂—C₆H₁₁ | 70 |
| 1.25 | 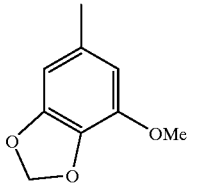 | (CH₂)₄—CH(CH₃)₂ | 140 |
| 1.26 | 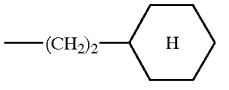 | n-heptyl | 112 |
| 1.27 | 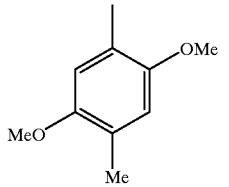 | —(CH₂)₂—C₆H₁₁ | 89 |

TABLE 1-continued

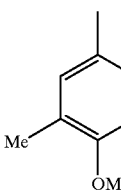

| PREPARATIONS | R₁ | R₂ | m.p. °C. |
|---|---|---|---|
| 1.28 | 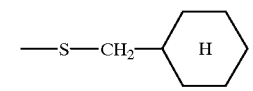 | —S—CH₂— | 93 |

Preparation 1.29

2-Amino-5-cyclohexylethyl-4-(2,6-dimethoxy-4-isopropylphenyl)thiazole

A) 1-Isopropenyl-2,4-dimethoxybenzene 10.57 g of 1-(2,4-dimethoxyphenyl)ethanone are dissolved in 100 ml of ether and 50 ml of THF under nitrogen. 55 ml of 1.6M methyllithium in ether are added at –50° C. and the mixture is left stirring for 2 hours between –60° C. and –40° C. and then for 30 minutes between –40° C. and 0° C. and for 3 hours at RT. It is cooled to 0° C. and 70 ml of 2N HCl are added. After separation of the phases by settling, the aqueous phase is extracted with ether and the organic phase is then dried over Na₂SO₄. This solution is concentrated and the residue is then taken up in 150 ml of THF and 75 ml of 2N HCl are added. After stirring for 4 hours at RT, 100 ml of water are added and this mixture is then extracted with ether. The organic phase is washed with Na₂CO₃, with water and then dried over Na₂SO₄ and concentrated. The residue is chromatographed on silica, eluting with a DCM/pentane mixture (70/30 and then 60/40). 5 g of the expected compound are obtained in the form of an oil.

B) 1-Isopropyl-2,4-dimethoxybenzene 4.96 g of the compound of the above step are dissolved in 100 ml of methanol, 0.2 g of 10% Pd/C is added and the mixture is then hydrogenated at room temperature and pressure. The catalyst is filtered off and the filtrate is then concentrated under vacuum to give 4.2 g of the expected compound in the form of an oil.

C) 2-Amino-5-cyclohexylethyl-4-(2,6-dimethoxy-4-isopropylphenyl)thiazole

The process is then performed according to the procedures described above. The 1-isopropyl-2,4-dimethoxybenzene is treated with 4-cyclohexylbutyryl chloride in the presence of AlCl₃, after which bromination of the ketone is carried out by reacting it with PTT and this product is reacted with thiourea to give the expected product: m.p.=143° C.

B—Preparation of the Substituted 2-indolecarboxylic Acids of Formula R'₃COOH:

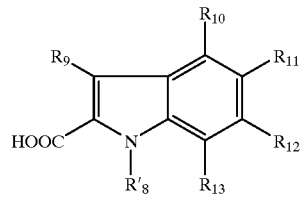

in which R'₈ is the precursor of R₈ and R₉, R₁₀, R₁₁, R₁₂ and R₁₃ are as defined above for (I).

Preparation 2.1

1-(Methoxycarbonylmethyl)-2-indolecarboxylic acid

A) Benzyl 2-indolecarboxylate 10.32 g of 2-indolecarboxylic acid in 70 ml of THF are placed in a three-necked flask at RT, 10.38 g of carbonyldiimidazole are added and, after the evolution of gas has ceased, 7.62 g of benzyl alcohol are then added. After refluxing for 5 hours, the mixture is poured into water and extracted with DCM, and the extracts are dried and evaporated. The crystals formed are washed with iPrOH to give 13.62 g of the expected compound: m.p.=136° C.

B) Benzyl 1-(methoxycarbonylmethyl)-2-indolecarboxylate 2.85 g of sodium hydride at 50% in oil and 10 ml of DMF are placed in a three-necked flask and nitrogen is bubbled through. 13.58 g of the compound of the above step dissolved in 50 ml of DMF are added and 9.09 g of methyl bromoacetate are then added slowly. After stirring overnight at RT, the mixture is poured onto ice and extracted with EtOAc, and the extracts are dried over Na₂SO₄ and evaporated; the residue is chromatographed on silica, eluting with a toluene/EtOAc mixture (95/5; v/v). 6.84 g of the expected compound are obtained, which product crystallizes from an EtOH/pentane mixture: m.p.=94° C.

C) 1-(Methoxycarbonylmethyl)-2-indolecarboxylic acid 6.84 g of the product of the above step are mixed with 80 ml of DMF, 80 ml of EtOH and 100 mg of 5% Pd/C and this mixture is hydrogenated with vigorous stirring for 8 hours.

The catalyst is filtered off, the filtrate is evaporated to dryness and the product is then crystallized from an EtOH/petroleum ether mixture. 4.30 g of the expected compound are thus obtained: m.p.=190° C.

Preparation 2.2

1-(tert-Butoxycarbonylmethyl)-2-indolecarboxylic acid

A) Benzyl 1-(tert-butoxycarbonylmethyl)-2-indolecarboxylate 50.25 g of benzyl 2-indolecarboxylate (Preparation 2.1, step A) are dissolved in 140 ml of anhydrous DMF, followed by addition over 30 minutes, under a stream of dry nitrogen, of a solution of 6.6 g of NaH at 80% in oil, in 100 ml of DMF. The reaction medium is stirred for 90 minutes at RT and is then cooled on an ice bath and 42.91 ml of tert-butyl bromoacetate are added dropwise. After stirring at RT overnight, the DMF is evaporated off and the residue is taken up in DCM and then in water. After stirring, the phases are separated by settling and the aqueous phase is then extracted twice-with DCM; the combined organic phases are washed with saturated NaCl solution and then dried over $MgSO_4$. After filtration and evaporation, the residue is taken up in a mixture of 100 ml of ethyl ether and 100 ml of heptane. After stirring for 2 hours, the crystals formed are filtered off and then washed with 50 ml of a heptane/ethyl ether mixture (70/30; v/v) and dried in an oven. 58 g of the expected product are obtained: m.p. 95–96° C.

B) 1-(tert-Butoxycarbonylmethyl)-2-indolecarboxylic acid 58 g of the benzyl ester of the above step are dissolved in 150 ml of ethanol and 150 ml of DMF; 3 g of 5% Pd/C are added under a stream of nitrogen and the reaction medium is hydrogenated at atmospheric pressure. The mixture is filtered through Celite®, the solvents are then evaporated off and the residue is taken up in water. After trituration, the solid formed is washed with water and is then dissolved in 1 litre of EtOAc. This organic phase is washed twice with water and then dried over $Na_2SO_4$. This solution is filtered and evaporated; the solid formed is triturated in the presence of 100 ml of a heptane/ethyl ether mixture (50/50; v/v). The product is again filtered off and dried in an oven to give 39.6 g of the expected compound in the form of a white solid: m.p.=156–157° C.

Preparation 2.3

5-Methyl-1-(tert-butyloxycarbonylmethyl)-2-indolecarboxylic acid

A) Benzyl 5-methyl-2-indolecarboxylate 2.43 g of 5-methyl-2-indolecarboxylic acid are dissolved in 15 ml of DMF; 2.11 g of DBU are added and the mixture is then left stirring for 1 hour at RT. 2.61 g of benzyl bromide are added dropwise and the mixture is then left stirring for 6 hours at RT. This mixture is concentrated under vacuum and the residue is taken up in EtOAc, washed with water, with saturated $Na_2CO_3$ solution, with sulphate buffer and then with saturated aqueous NaCl. It is dried over $Na_2SO_4$ and then concentrated. The residue crystallizes from pentane and 3.3 g of the expected compound are obtained: m.p.= 150–152° C.

B) Benzyl 5-methyl-1-(tert-butyloxycarbonylmethyl)-2-indolecarboxylate 3.26 g of the compound of the above step are dissolved in 30 ml of DMF and 0.65 g of NaH at 50% in oil is added portionwise, under nitrogen. After stirring for two and a half hours at RT, 2.64 g of tert-butyl bromoacetate are added dropwise, at 80° C., and the mixture is left stirring for 4 hours at RT. The mixture is concentrated under vacuum, the residue is taken up in 150 ml of sulphate buffer and is then extracted with EtOAc, and the extracts are dried over $Na_2SO_4$ and concentrated. 3.53 g of the expected compound are obtained, which product crystallizes from pentane: m.p.= 80–82° C.

C) 5-Methyl-1-(tert-butyloxycarbonylmethyl)-2-indolecarboxylic acid 3.47 g of the compound of the above step are dissolved in 30 ml of absolute ethanol and 15 ml of DMF, 0.3 g of 10% Pd/C is added, under nitrogen, and the mixture is then hydrogenated at RT under atmospheric pressure. The catalyst is filtered off and the filtrate is then concentrated under vacuum to give 2.86 g of the expected compound, which crystallizes from pentane: m.p.=174–176° C.

Preparation 2.4

4-Methoxy-1-(tert-butyloxycarbonylmethyl)-2-indolecarboxylic acid

A) Benzyl 4-methoxyindole-2-carboxylate 2.65 g of 4-methoxyindole-2-carboxylic acid are dissolved in 15 ml of DMF, 2.11 g of DBU are added and the mixture is then stirred at RT for 1 hour. 2.61 g of benzyl bromide are added dropwise at RT and this mixture is stirred for 5 hours at RT. The mixture is concentrated under vacuum and the residue is taken up in EtOAc, washed with water, with saturated $Na_2CO_3$ solution, with sulphate buffer and then with saturated aqueous NaCl. This solution is dried over $Na_2SO_4$ and concentrated. 3.57 g of the expected compound are obtained, which product crystallizes from pentane: m.p.=162–164° C.

B) Benzyl 4-methoxy-1-(tert-butyloxycarbonylmethyl)-2-indolecarboxylate 3.3 g of the compound of the above step are dissolved in 30 ml of DMF, 0.62 g of NaH at 50% in oil is added portionwise, under nitrogen, and the mixture is left stirring for two and a half hours at RT. 2.52 g of tert-butyl bromoacetate are added dropwise at RT and the mixture is stirred for 5 hours at RT. This mixture is concentrated under vacuum and the residue is taken up in 150 ml of sulphate buffer and then extracted with EtOAc and the extracts are dried over $Na_2SO_4$ and concentrated. 4.2 g of the expected compound are obtained, which product crystallizes from pentane: m.p.= 96–98° C.

C) 4-Methoxy-1-(tert-butyloxycarbonylmethyl)-2-indolecarboxylic acid 4.13 g of the compound of the above step are dissloved in 30 ml of absolute ethanol and 30 ml of DMF, 0.4 g of 10% Pd/C is added and the mixture is then hydrogenated at RT under atmospheric pressure. The catalyst is filtered off and the filtrate is concentrated to give 2.36 g of the expected compound, which crystallizes from a DCM/pentane mixture: m.p.=222–224° C.

Preparation 2.5

5-Chloro-1-(ethoxycarbonylmethyl)-2-indolecarboxylic acid

A) tert-Butyl 5-chloro-2-indolecarboxylate 5.52 g of 5-chloro-2-indolecarboxylic acid are dissolved in 40 ml of DMF, 4.57 g of carbonyldiimidazole are added at RT, under nitrogen, the mixture is then heated to 40° C and 4.3 g of DBU and 4.17 g of tertbutanol are added. Heating is continued at 40° C. for 3 hours, the precipitate formed is then filtered off and the filtrate is concentrated under vacuum. The residue is taken up in EtOAc, washed with 10% $Na_2CO_3$ solution, with saturated aqueous NaCl, with sulphate buffer and then dried over $Na_2SO_4$ and concentrated. The residue is chromatographed on silica, eluting with DCM, to give 0.45 g of the expected compound: m.p.=140–142° C.

B) tert-Butyl 5-chloro-1-(ethoxycarbonylmethyl)-2-indolecarboxylate 0.45 g of the compound of the above step is dissolved in 15 ml of DMF and 94 mg of NaH at 50% in oil are then added portionwise at RT, under nitrogen. After stirring for 4 hours at RT, 0.33 g of ethyl bromoacetate is added dropwise at RT and the mixture is left stirring for 4 hours at RT. The mixture is concentrated under vacuum and the residue is taken up in EtOAc, washed with sulphate buffer, dried over $Na_2SO_4$ and concentrated to give 0.6 g of the expected compound in the form of an oil.

C) 5-Chloro-1-(ethoxycarbonylmethyl)-2-indolecarboxylic acid 0.6 g of the compound of the above step is dissolved in 10 ml of DCM, this solution is placed on an ice bath, 10 ml of TFA are added and the mixture is then stirred for 4 hours on the ice bath. After leaving overnight at 4° C., the mixture is concentrated under vacuum. The residue crystallizes from pentane. After drying, 0.37 g of the expected compound is obtained: m.p.=198–200° C.
Preparation 2.6

1-(2-Ethoxycarbonylbenzyl)-2-indolecarboxylic acid

A) Benzyl 2-indolecarboxylate

This ester can be prepared according to an alternative process to the one described in Preparation 2.1.

100 g of 2-indolecarboxylic acid are dissolved in 500 ml of DMF and 93 ml of DBU are added dropwise, followed by 89.7 ml of benzyl bromide. After stirring overnight at RT, the DMF is evaporated off and the mixture is then poured into water. The precipitate formed is filtered off, washed with water and taken up in EtOAc. The organic phase is washed with 5% $Na_2CO_3$ solution, with sulphate buffer and then dried over $Na_2SO_4$. After filtration, the solvents are evaporated off and the product is triturated from ether, filtered off and dried. 133 g of the expected compound are obtained: m.p.=136° C.

B) Ethyl 2-bromomethylbenzoate

A mixture containing 8.2 g of ethyl 2-methylbenzoate, 10.7 g of NBS and 0.2 g of benzoyl peroxide is refluxed in 50 ml of $CCl_4$, with irradiation. After 45 minutes, the solution is cooled and the succinimide formed is filtered off. The organic phase is washed with 5% $NaHCO_3$ solution and then dried over $MgSO_4$ and evaporated. The product is used without further purification in the following step.

C) Benzyl 1-(2-ethoxycarbonylbenzyl)-2-indolecarboxylate 12.56 g of the compound prepared in step A are dissolved in 50 ml of DMF, under nitrogen. 1.81 g of NaH at 80% in oil are added portionwise while maintaining the temperature below 20° C. with an ice bath. After stirring for 1 hour at RT, the mixture is cooled to +4° C. with an ice bath, the product obtained in the above step dissolved in 20 ml of DMF is added dropwise and the mixture is then left stirring at RT overnight. The DMF is evaporated off, the residue is taken up in a water/ice mixture and extracted 3 times with ether, and the organic phases are then combined, washed with saturated NaCl solution, dried over $Na_2SO_4$ and evaporated. The product is dissolved in toluene and filtered, and the filtrate is chromatographed on silica H, eluting with toluene. 9 g of the expected compound are obtained in the form of an oil.

D) 1-(2-Ethoxycarbonylbenzyl)-2-indolecarboxylic acid

All of the product obtained in the above step is hydrogenated in the presence of Pd/C, according to the usual technique. 6.13 g of the expected compound are obtained: m.p.=191–192° C.
Preparation 2.7

1-(Methoxycarbonylethyl)-2-indolecarboxylic acid

A) Benzyl 1-(2-cyanoethyl)-2-indolecarboxylate 1.6 ml of Triton B at 40% in water and 4 ml of acrylonitrile are mixed in 40 ml of dioxane, and 9.44 g of benzyl 2-indolecarboxylate are then added with stirring. The mixture is heated at 80° C. for 24 hours and is then poured into 500 ml of ice-cold water. The precipitate formed is filtered off, taken up in EtOAc and this solution is then dried over $Na_2SO_4$ and concentrated to give 10.1 g of the expected compound, which crystallizes: m.p.=98–100° C.

B) Benzyl 1-(methoxycarbonylethyl)-2-indolecarboxylate 10.1 g of the compound of the above step are dissolved in 60 ml of DCM and 12 ml of MeOH and 120 ml of hydrochloric ether are added. After 72 hours at 0° C., the imidate formed is filtered off and the precipitate is then taken up in 30 ml of water and of acetic acid. The solution formed is stirred for 2 hours at RT, 50 ml of 1N HCl are then added, this mixture is extracted with EtOAc and the extracts are dried over $Na_2SO_4$ and concentrated to give 9 g of the expected compound in the form of an oil.

C) 1-(Methoxycarbonylethyl)-2-indolecarboxylic acid

The 9 g of the compound of the above step are hydrogenated in ethanol in the presence of Pd/C to give 3.95 g of the expected compound: m.p.=118–120° C.
Preparation 2.8

1-(tert-Butoxycarbonylmethyl)-5-ethyl-2-indolecarboxylic acid

A) 2-[(4-Ethylphenyl)hydrazono]propionic acid

This compound is prepared according to V. Prelog et al., Helv. Chem. Acta, 1948, 31, 1178.

13.2 g of 4-ethylaniline are dissolved in 150 ml of concentrated HCl. The solution is cooled to 0° C. and 10.6 g of $NaNO_2$ dissolved in 40 ml of water are then added at a temperature of less than or equal to 5° C. After 5 minutes, a solution of $SnCl_2.2H_2O$ in 75 ml of concentrated HCl is added, at 5° C., and this mixture is then left stirring for two and a half hours at 0° C. It is filtered and the precipitate formed is washed with the minimum amount of water at 5° C. and, then dissolved in 500 ml of water at 5° C. 9.5 ml of pyruvic acid in 50 ml of water are added at 10° C. After leaving overnight in a refrigerator, the precipitate formed is filtered off and then taken up in 120 ml of benzene. This solution is dried over $Na_2SO_4$ and then concentrated to give 11 g of expected compound.

B) Ethyl 2-[(4-ethylphenyl)hydrazono]propionate 11 g of the compound of the above step are refluxed for 2 hours in 100 ml of absolute ethanol and 6 ml of $H_2SO_4$. The mixture is concentrated to one-third and is then poured onto ice-cold water and extracted with ether, and the ether extracts are washed with $Na_2CO_3$, dried over $Na_2SO_4$ and concentrated. The precipitate formed is taken up in pentane and then filtered to give 7.9 g of the expected compound.

C) Ethyl 5-ethyl-2-indolecarboxylate 9.6 g of p-toluenesulphonic acid are refluxed in 100 ml of benzene, 7.9 g of the compound of the above step are then added cautiously and the resulting mixture is refluxed for one and a half hours. The insoluble material is filtered off and the benzene solution is then washed with saturated $NaHCO_3$ solution, dried and then concentrated. The residue precipitates from pentane. 5.4 g of the expected compound are obtained.

D) 5-Ethyl-2-indolecarboxylic acid 5.4 g of the compound of the above step are refluxed for 3 hours in 50 ml of ethanol and 4 ml of water containing 3.4 g of KOH. The medium is concentrated, the residue is taken up in water and washed with ether, the aqueous phase is acidified by addition of concentrated HCl and the precipitate formed is then filtered off to give 3.95 g of the expected compound.

E) Benzyl 5-ethyl-2-indolecarboxylate 4 g of the compound of the above step, 3.14 ml of DBU and 2.75 ml of benzyl bromide are mixed together in 30 ml of DMF and the mixture is left stirring for 48 hours at RT. The medium is poured into 300 ml of water at 5° C. and the precipitate formed is filtered off and then washed with water at 5° C. and then with pentane. This precipitate is taken up in 300 ml of ethyl acetate, dried over $Na_2SO_4$ and concentrated to give 4.93 g of the expected compound.

F) Benzyl 5-ethyl-1-(tert-butoxycarbonylmethyl)-2-indolecarboxylate 4.93 g of the compound of the above step are dissolved in 40 ml of DMF, 0.78 g of sodium hydride at 60% in oil is added portionwise and the mixture is then heated for 30 minutes at 60° C. It is allowed to cool and 3.1 ml of tert-butyl bromoacetate are added dropwise. After leaving overnight at RT, the DMF is evaporated off, the residue is extracted with ether, the ether extracts are washed with water and dried over $Na_2SO_4$, and the residue is then chromatographed on silica, eluting with DCM/pentane (60/40; v/v) to give 5.2 g of the expected compound.

G) 5-Ethyl-1-(tert-butoxycarbonylmethyl)-2-indolecarboxylic acid 5.2 g of the compound of the above step are hydrogenated at room temperature and pressure in 100 ml of ethanol and 120 ml of ethyl acetate in the presence of 520 mg of 10% Pd/C. The catalyst is filtered off and washed with ethyl acetate and the filtrate is then concentrated to dryness to give 4 g of the expected compound.

Preparation 2.9

1-(tert-Butoxycarbonylmethyl)-5-trifluoromethyl-2-indolecarboxylic acid

A) Ethyl 2-[(4-trifluoromethyl)phenylhydrazono]-propionate 19.3 g of 4-trifluoromethylaniline are added dropwise to a mixture of 200 ml of water and 32 ml of concentrated HCl, this mixture is cooled to −5° C. and 8.3 g of $NaNO_2$ in 20 ml of water are added. Separately, a solution of 98 g of sodium acetate hydrate ($CH_3CO_2Na.3H_2O$) and 29 ml of ethyl 2-methyl-3-oxobutyrate in 125 ml of ethanol and 90 g of crushed ice is prepared; it is cooled to −10° C., the reaction mixture prepared above is added and the temperature is maintained at −10° C. for 5 minutes and is then allowed to return to RT. The precipitate is filtered off and washed with water and then with pentane, to give 22.5 g of the expected compound.

B) 1-(tert-Butoxycarbonylmethyl)-5-trifluoromethyl-2-indolecarboxylic acid

The process is then performed according to the procedure described in steps C to G of the above preparation, to give the expected product.

Preparation 2.10

1-(tert-Butoxycarbonylmethyl)-4-trifluoromethyl-2-indolecarboxylic acid

This compound is prepared from 3-trifluoromethylaniline using the procedure described in the above preparation.

Preparation 2.11

5-Methyl-1-(ethoxycarbonylpropyl)-2-indolecarboxylic acid

A) Ethyl 5-methyl-2-indolecarboxylate 15.4 g of $NaNO_2$ in 4 ml of water are added, at 0° C., to 23.57 g of p-toluidine in 50 ml of HCl and 100 ml of water; after stiring for 20 minutes, 18.2 g of sodium acetate ate added. Separately, a mixture of 28.8 g of ethyl 2-methyl-3-oxobutyrate in 100 ml of ethanol is prepared, at 0° C, and is treated with 11.22 g of potassium hydroxide in20 ml of water and 200 g of crushed ice. The diazonium salt solution prepared above is added and the mixture is left stirring for 3 hours at 0° C. After leaving overnight in a refrigerator, it is poured onto saturated NaCl solution and is then extracted with EtOAc, dried over $MgSO_4$ and concentrated. The residue is taken up in toluene, 16 g of para-toluenesulphonic acid are added and the mixture is refluxed overnight, eliminating the water using Dean-Stark apparatus. The reaction medium is chromatographed on silica, eluting with toluene, to give 12 g of the expected product: m.p.=133° C.

B) 5-Methyl-2-indolecarboxylic acid 12 g of the ester obtained in the above step are placed in 50 ml of ethanol and a solution of 3 g of sodium hydroxide in 30 ml of water is added. After stirring for 30 minutes, the solvent is evaporated off, the residue is taken up in water, washed with EtOAc and the aqueous phases are then acidified to pH=2 by addition of concentrated HCl, this mixture is extracted with EtOAc and the extracts are dried over MgSO$_4$ and concentrated to give 8.83 g of the expected compound: m.p.=218° C.

C) Benzyl 5-methyl-2-indolecarboxylate

This ester is prepared by reaction with benzyl bromide in the presence of DBU, according to the usual methods: m.p.=141° C.

D) Benzyl 5-methyl-1-(ethoxycarbonylpropyl)-2-indolecarboxylate 0.6 g of sodium hydride at 60% in oil is placed in 5 ml of DMF under nitrogen, 3 g of the compound of the above step are added and the mixture is left stirring for 2 hours. 3.8 g of ethyl iodobutyrate in 10 ml of DMF are added to the reaction medium, at 0° C. After stirring for 30 minutes, the solvent is evaporated off and the residue is then taken up in EtOAc. It is washed with Na$_2$CO$_3$ solution and then dried over MgSO$_4$ and concentrated, to give 2.75 g of the expected compound in the form of an oil.

E) 5-Methyl-1-(ethoxycarbonylpropyl)-2-indolecarboxylic acid

All of the compound obtained in the above step is hydrogenated for 2 hours at room temperature and pressure in the presence of 1 g of 10% Pd/C in 80 ml of MeOH and 20 ml of DMF. The catalyst is filtered off on Celite. After evaporation of the solvents, the product obtained is triturated from heptane to give 1.54 g of the expected compound: m.p.=142° C.

Preparation 2.12

1-(Ethoxycarbonylpentyl)-2-indolecarboxylic acid

A) Benzyl 1-(ethoxycarbonylpentyl)-2-indolecarboxylate

A mixture containing 3 g of benzyl 2-indolecarboxylate in 30 ml of anhydrous DMF and 500 mg of sodium hydride at 60% in oil is left stirring under a nitrogen atmosphere for 1 hour. 3 g of ethyl 6-bromohexanoate in 10 ml of DMF are added, at 0° C., and the mixture is left stirring overnight at RT. The solvents are evaporated off and the residue is taken up in EtOAc, washed with water, dried over MgSO$_4$ and concentrated. The residue is chromatographed on a column of silica H, eluting with a heptane/toluene mixture (50/50; v/v) to give 4.17 g of the expected compound.

B) 1-(Ethoxycarbonylpentyl)-2-indolecarboxylic acid

All of the compound of the above step is hydrogenated for 2 hours at room temperature and pressure in they presence of 1 g of 5% Pd/C. The catalyst is filtered off on Celite® and the filtrate is then chromatographed on silica H, eluting with a DCM/MeOH mixture (100/3; v/v). 2.14 g of the expected compound are obtained: m.p.=62° C.

Preparation 2.13

5,7-Dimethyl-1-(tert-butoxycarbonylmethyl)-2-indolecarboxylic acid

A) Ethyl 5,7-dimethyl-2-indolecarboxylate

This ester can be prepared via 3 different routes.
Route 1 a) Ethyl 2-[(2,4-dimethylpheny)hydrazono]propionate 17.11 g of 2,4-dimethylaniline are dissolved in 36 ml of concentrated HCl diluted with 280 ml of water. A solution of 10.13 g of sodium nitrite in 30 ml of water is added, at 0° C. This mixture is stirred for 15 minutes at 0° C. and the solution obtained is then poured, at 0° C., onto a solution of 20.5 g of ethyl 2-methyl-3-oxobutyrate in 150 ml of ethanol. At the same time, 31.7 g of potassium hydroxide dissolved in 32 ml of water are added and the mixture is then stirred for 15 minutes at 0° C. The medium is neutralized with 70.6 ml of 2N HCl. The precipitate formed is filtered off, washed with water and then dissolved in EtOAc. This solution is dried over Na$_2$SO$_4$ and concentrated. The crystalline residue is taken up in isopropyl ether and then filtered to give 25.49 g of the expected compound: m.p.=146° C.

b) Ethyl 5,7-dimethyl-2-indolecarboxylate 19 g of the product of the above step are heated at 75° C. for 3 hours in 190 ml of formic acid. The reaction medium is poured into 2.5 litres of cold water and the precipitate formed is filtered off and washed with water. The precipitate is dissolved in EtOAc and this solution is dried over Na$_2$SO$_4$ and concentrated. The crystalline residue is washed with heptane and the product obtained is then recrystallized from isopropyl ether to give 8.9 g of the expected compound: m.p.=141–143° C.

Route 2 a) Ethyl 3-(3,5-dimethylphenyl)-2-azido-2-propenoate

A mixture of 5 g of 3,5-dimethylbenzaldehyde and 19.3 g of ethyl azidoacetate is added, at −10° C. under dry nitrogen, to a mixture of 25 ml of ethanol and 50 ml of a 21% solution of sodium ethoxide in ethanol. The mixture is left stirring for 1 hour at −10° C. and for fourteen and a half hours at +5° C. It is poured into 100 ml of water and the precipitate formed is filtered off and washed with water. The precipitate is dissolved in ether and this solution is dried over MgSO$_4$ and then evaporated to give the product, which is used without further purification in the subsequent step.

b) Ethyl 5,7-dimethyl-2-indolecarboxylate

A solution of the product of the above step in 100 ml of xylene is added dropwise to 100 ml of refluxing xylene. After two hours, the reaction medium is evaporated and the crystalline residue is washed with pentane to give 4.2 g of the expected compound: m.p.=146° C.

Route 3 a) N-(Boc)-2,4,6-trimethylaniline

A solution of 36 g of Boc$_2$O in 60 ml of heptane is refluxed. 20.28 g of 2,4,6-trimethylaniline are added dropwise and the mixture is refluxed for 3 hours. It is cooled and filtered through silica, eluting with DCM. This solution is evaporated to give 33.5 g of the expected compound in the form of a white crystalline product: m.p.=73–73.5° C.

b) Ethyl 5,7-dimethyl-2-indolecarboxylate

A solution of 4.7 g of the product of the above step in 70 ml of anhydrous THF is cooled to −40° C. under dry nitrogen. 34 ml of a 1.3M solution of sec-BuLi in cyclohexane are added dropwise. The mixture is allowed to return to −20° C. over 30 minutes. It is cooled to −40° C. and this yellow solution is added rapidly to a solution of 5.9 g of ethyl oxalate in 70 ml of anhydrous THF and is then allowed to return to RT under nitrogen. Two hours later, it is cooled to +4° C. and 200 ml of pH 2 buffer are added slowly. This mixture is extracted twice with ether and the extracts are dried over MgSO$_4$ and evaporated. The oily residue is taken up in 100 ml of THF and 160 ml of 6N HCl. This mixture is heated at 60° C. for one and a half hours and then cooled. It is extracted with ether and the extracts are dried over MgSO$_4$ and evaporated. The product is filtered through silica, eluting with toluene, to give 1.6 g of the expected compound: m.p.=140–141° C.

B) 5,7-Dimethyl-2-indolecarboxylic acid 8.7 g of the product of the above step in 100 ml of absolute ethanol are stirred with 100 ml of 2N sodium hydroxide for 6 days and the mixture is then refluxed for 1 hour. It is cooled to RT and 20 ml of concentrated HCl are added. The precipitate formed is filtered off and washed with water. The precipitate is dissolved in EtOAc and this solution is dried over Na$_2$SO$_4$ and concentrated to give 7.15 g of the expected compound: m.p.=254–256° C.

C) Benzyl 5,7-dimethyl-2-indolecarboxylate

This ester can be prepared via two different routes.
Route 1

8.3 g of the product of the above step are dissolved in 60 ml of DMF. 6.68 g of DBU are added and the mixture is stirred for 15 minutes at RT, after which 8.25 g of benzyl bromide are added and the mixture is stirred for 48 hours at RT. It is concentrated under vacuum and the residue is then taken up in 500 ml of water. The precipitate formed is filtered off and dissolved in EtOAc, and the organic solution is then washed with saturated aqueous Na$_2$CO$_3$, with sulphate buffer and with saturated aqueous NaCl. The resulting solution is dried over Na$_2$SO$_4$ and concentrated and the residue is then washed with and crystallized from heptane. 11.15 g of the expected compound are obtained: m.p.=130–131° C.
Route 2

A solution of 4.7 g of N-Boc-2,4,6-trimethylaniline obtained in step a) of route 3 above in 70 ml of THF is cooled to −40° C. under dry nitrogen. 34 ml of a 1.3M solution of sec-BuLi in cyclohexane are added dropwise and the mixture is allowed to return to −20° C. over 30 minutes. It is cooled to −40° C. and this yellow solution is added rapidly to a solution of 9.53 g of benzyl oxalate in 70 ml of anhydrous THF. The mixture is allowed to return to RT under nitrogen. Two hours later, it is cooled to +4° C. and 200 ml of pH 2 buffer are added. This mixture is extracted twice with ether and the extracts are dried over MgSO$_4$ and evaporated. The residue is cooled to +4° C. and a mixture of 5 ml of anisole, 20 ml of DCM and 20 ml of TFA is added. This mixture is allowed to return to RT. After 3 hours, it is evaporated and the residue is taken up in water. It is extracted with EtOAc, the phases are separated out by settling and the organic phase is washed with 5% Na$_2$CO$_3$ solution. The resulting solution is dried over MgSO$_4$ and evaporated and the residue is then filtered on silica, eluting with toluene. 1.24 g of the expected compound are obtained: m.p.=132.5–133.5° C.

D) Benzyl 5,7-dimethyl-1-(tert-butoxycarbonylmethyl)-2-indolecarboxylate 167 mg of NaH at 60% in oil, are placed in 10 ml of DMF under nitrogen and 1 g of the compound-from the above step is added portionwise. After stirring for 3 hours at RT, 0.7 ml of tert-butyl bromoacetate dissolved in 1 ml of DMF is added and the mixture is left stirring for 12 hours. The excess sodium hydride is hydrolysed and the reaction medium is then concentrated and taken up in EtOAc, and this solution is washed with water and then with Na$_2$CO$_3$ solution. The resulting solution is dried over Na$_2$SO$_4$ and then evaporated and the residue is chromatographed on silica, eluting with pentane/DCM (60/40; v/v). 940 mg of the expected compound are obtained: m.p.=115° C.

E) 5,7-Dimethyl-1-(tert-butoxycarbonylmethyl)-2-indolecarboxylic acid

All of the compound from the above step is hydrogenated at room temperature and pressure in the presence of 100 mg of 5% Pd/C, in 5 ml of ethanol and 20 ml of EtOAc. The catalyst is filtered through Celite® and the filtrate is then evaporated to give 596 mg of the expected compound: m.p.=210° C.

Preparation 2.13a

5,7-Dimethyl-1-(methoxycarbonylmethyl)-2-indolecarboxylic acid

A) Benzyl 5,7-dimethyl-1-(methoxycarbonylmethyl)-2-indolecarboxylate 11.03 g of the product from step C of Preparation 2.13 are dissolved in 50 ml of CH$_3$CN. 1.35 g of benzyltriethylammonium chloride, 12.39 g of potassium carbonate and 7.55 g of methyl bromoacetate are added. The mixture is refluxed for 3 hours and 1.64 g of potassium carbonate and 1.81 g of methyl bromoacetate are then added. The mixture is refluxed for a further 3 hours and the inorganic materials are then filtered off. The filtrate is concentrated and the residue is then chromatographed on silica H, eluting with toluene. 9.7 g of the expected compound are obtained: m.p.=91–93° C.

B) 5,7-Dimethyl-1-(methoxycarbonylmethyl)-2-indolecarboxylic acid 9.6 g of the product from the above step are dissolved in 100 ml of DMF and 100 ml of absolute ethanol. 900 mg of 10% Pd/C and hydrogen are added at room temperature and atmospheric pressure. The mixture is filtered through Hyflo, the filtrate is concentrated under vacuum and the residue is then taken up in 300 ml of water. The precipitate is filtered off and is then dissolved in EtOAc. This solution is dried over Na$_2$SO$_4$ and concentrated, and the residue is then washed with and crystallized from isopropyl ether. 6.11 g of the expected compound are obtained: m.p.=221–223° C.

Preparation 2.14

5,6-Dimethyl-1-(tert-butoxycarbonylmethyl)-2-indolecarboxylic acid

A) 2,4,5-Trimethylaniline 19.70 g of 2,4,5-trimethylnitrobenzene are dissolved in 500 ml of ethanol and the solution is then hydrogenated at room temperature and pressure in the presence of 1 g of 5% Pd/C. The catalyst is filtered off on Celite® and the medium is then evaporated to give 15.67 g of the expected compound.

B) (N-Boc)-2,4,5-trimethylaniline.

41 g of (Boc)$_2$O dissolved in 60 ml of heptane is refluxed, 15.67 g of the compound obtained in the above step in 20 ml of EtOAc are then added dropwise and refluxing is continued for 3 hours. After cooling, the product crystallizes and the crystals formed are filtered off to give 13.68 g of the expected compound. The filtrate is evaporated off and the residue is taken up in heptane and stirred; a further 8.35 g of crystals of the expected product are filtered off. 22.03 g of product are thus obtained: m.p.=109–110° C.

C) Ethyl 5,6-dimethyl-2-indolecarboxylate 4.70 g of the compound from the above step dissolved in 70 ml of THF are cooled to −40° C. under nitrogen and 34 ml of 1.3M sec-butyllithium in cyclohexane are then added dropwise, after which the mixture is left stirring for 30 minutes at −40° C. The reaction medium is poured into a stirred solution, at −40° C., of 5.9 g of ethyl oxalate in 70 ml of THF and the mixture is allowed to return to RT. It is cooled to 0° C. and 100 ml of water are then added. This mixture is extracted with $Et_2O$ (3 times), the extracts are dried over $Na_2SO_4$ and evaporated and the residue is then chromatographed on silica, eluting with DCM. The solid obtained is taken up in a mixture of 60 ml of water, 60 ml of 12N HCl and 60 ml of THF and is then heated for 3 hours at 60° C. After cooling, it is extracted with $Et_2O$ (3 times), the extracts are dried over $Na_2SO_4$ and evaporated and the residue is then chromatographed on silica H, eluting with toluene. 1.37 g of the expected compound are obtained: m.p.=163.5–164.5° C.

D) 5,6-Dimethyl-2-indolecarboxylic acid

The ester obtained in the above step is hydrolysed by reacting it with sodium hydroxide in methanol, followed by acidification with concentrated HCl: m.p.=266–266.5° C.

E) Benzyl 5,6-dimethyl-2-indolecarboxylate

This ester is prepared by reaction with benzyl bromide in the presence of DBU according to the usual methods: m.p.=172.5–173.5° C.

F) Benzyl 5,6-dimethyl-1-(tert-butoxycarbonylmethyl)-2-indolecarboxylate 1.67 g of the compound from the above step are cooled to +4° C. under nitrogen and 150 mg of NaH at 60% in oil are added portionwise. After stirring for 30 minutes at +4° C., 0.7 g of tert-butyl bromoacetate dissolved in 5 ml of DMF is added dropwise. The mixture is allowed to return to RT and, after leaving overnight, the DMF is evaporated off, the residue is taken up in water and the solid is filtered off, washed with water and then taken up in EtOAc. The organic phase is washed with $H_2O$ (twice), dried over $Na_2SO_4$ and evaporated and then triturated from 70 ml of heptane/ether (50/20; v/v) and the product is filtered off and dried to give 2 g of the expected compound in the form of a white solid: m.p.=133–134° C.

G) 5,6-Dimethyl-1-(tert-butoxycarbonylmethyl)-2-indolecarboxylic acid

The expected product is obtained by catalytic hydrogenation in the presence of 5% Pd/C: m.p.=240–241° C.

Preparation 2.15

4,5-Dimethoxy-1-(tert-butoxycarbonylmethyl)-2-indolecarboxylic acid

A) Ethyl 2-azido-3-(2,3-dimethoxyphenyl)acrylate

A sodium ethoxide solution, prepared using 80 ml of absolute ethanol and 2.76 g of sodium, is cooled to −30° C., under nitrogen. 4.99 g of 2,3-dimethoxybenzaldehyde and 15.5 g of ethyl azidoacetate are added and the mixture is then left stirring between −20° C. and −10° C. for 2 hours. The reaction medium is poured into 250 ml of water containing 25 ml of concentrated HCl. The precipitate formed is filtered off, washed with water and then dissolved in ether. This solution is dried over $Na_2SO_4$ and concentrated to give 5.86 g of the expected compound: m.p.<50° C.

B) Ethyl 4,5-dimethoxy-2-indolecarboxylate 5.85 g of the compound obtained in the above step are dissolved in 200 ml of toluene and the solution is refluxed for 7 hours. It is left for 2 days at RT and is then concentrated under vacuum. The residue is chromatographed on silica H, eluting with DCM/MeOH (100/0.6; v/v). After crystallization from pentane, 2.32 g of the expected compound are obtained: m.p.=129–131° C.

The process is then performed according to the usual steps in order to prepare the following compounds:

C) 4,5-Dimethoxy-2-indolecarboxylic acid: m.p.=258–260° C.

D) Benzyl 4,5-dimethoxy-2-indolecarboxylate: m.p.=109–111° C.

E) Benzyl 4,5-dimethoxy-1-(tert-butoxycarbonylmethyl)-2-indolecarboxylate: m.p.=70–72° C.

F) 4,5-Dimethoxy-1-(tert-butoxycarbonylmethyl)-2-indolecarboxylic acid: m.p.=206–208° C.

Preparation 2.16

4,5-Dichloro-1-(ethoxycarbonylmethyl)-2-indoleacetic acid

This compound is prepared from 2,3-dichlorobenzaldehyde, working according to the preparation described above: m.p.=205–207° C.

Preparation 2.17

3,5-Dimethyl-1-(methoxycarbonylethyl)-2-indolecarboxylic acid

A) Ethyl 3,5-dimethyl-2-indolecarboxylate 23.57 g of p-toluidine are placed in a mixture of 120 ml of water and 50 ml of concentrated HCl, followed by dropwise addition, at 0° C., of 15.4 g of $NaNO_2$ in 40 ml of water and the mixture is left stirring for 20 minutes at 0° C. A solution of 32 g of ethyl 2-ethyl-3-oxobutyrate in 150 ml of EtOH and 150 ml of 20% NaOH solution are added, at −10° C., to the p-toluenediazonium chloride solution thus formed. After stirring for 30 minutes at −5° C., the mixture is acidified to pH=4 by addition of dilute HCl and one litre of water. On trituration, a red solid forms, which is filtered off and then dried in an oven at 40° C. This solid is taken up in 200 ml of absolute EtOH and 20 ml of concentrated $H_2SO_4$ and the mixture is then refluxed for 45 minutes. The reaction medium is poured into an ice/water mixture and filtered, the precipitate is then taken up in EtOAc and this solution is washed with water and dried over $MgSO_4$. The residue is chromatographed on silica, eluting with a DCM/heptane mixture: m.p.=118° C.

B) 3,5-Dimethyl-2-indolecarboxylic acid

This compound is obtained by hydrolysis of the above ester: m.p.=177° C.

C) Benzyl 3,5-dimethyl-2-indolecarboxylate

This compound is obtained from the above acid by reaction with benzyl bromide in the presence of DBU: m.p.=91° C.

D) Benzyl 3,5-dimethyl-1-(2-cyanoethyl)-2-indolecarboxylate

The reaction is carried out according to a procedure analogous to the one described in J. Chem. Soc. (C), 1967, 2599–2601 for the N-cyanoethylation of indoles.

0.5 ml of Triton B as an aqueous 40% solution and 2.2 ml of acrylonitrile are placed in 20 ml of dioxane, followed by addition with a spatula of 3 g of the compound from the above step and, after total dissolution, the solution is heated at 80° C. for 24 hours. The reaction medium is evaporated, the residue is taken up in EtOAc and this solution is then washed with $Na_2CO_3$ solution and dried over $MgSO_4$. The residue is chromatographed on silica, eluting with heptane/toluene (50/50; v/v). 3.2 g of the expected compound are obtained: m.p.=71° C.

E) Benzyl 3,5-dimethyl-1-(methoxycarbonylethyl)-2-indolecarboxylate 3.2 g of the compound from the above step are placed in 30 ml of DCM and 3.8 ml of MeOH, and 45 ml of hydrochloric ether are added. After 2 days at +4° C., the white solid formed is filtered off, washed with an $Et_2O$/heptane mixture (50/50; v/v) and then taken up in 15 ml of water and 15 ml of acetic acid and heated at 100° C. for 30 minutes. 50 ml of water are added, the mixture is extracted with DCM and the extracts are then dried over $MgSO_4$ to give 1.72 g of the expected compound in the form of an oil.

F) 3,5-Dimethyl-1-(methoxycarbonylethyl)-2-indolecarboxylic acid

All of the compound obtained in the above step is hydrogenated at room temperature and atmospheric pressure in 200 ml of 90% EtOH in the presence of 300 mg of 5% Pd/C. The catalyst is filtered off on Celite® and the filtrate is then triturated from heptane containing a small amount of $Et_2O$. 0.8 g of the expected compound is obtained: m.p.=169° C.

Preparation 2.18
5-(N-tert-Butoxycarbonylamino)-1-(tert-butoxycarbonylmethyl)-2-indolecarboxylic acid

A) 5-Nitro-2-indolecarboxylic acid 13 g of ethyl 5-nitro-2-indolecarboxylate are placed in 200 ml of EtOH and the solution is treated for 12 hours with 15 g of 30% NaOH solution. After evaporation of the solvent, the residue is acidified with concentrated HCl and then filtered to give 10.8 g of the expected compound.

B) Benzyl 5-nitro-2-indolecarboxylate

This compound is prepared by reaction with benzyl bromide in the presence of DBU: m.p.=192° C.

C) Benzyl 5-nitro-1-(tert-butoxycarbonylmethyl)-2-indolecarboxylate

This compound is obtained by reaction with NaH, followed by tert-butyl bromoacetate: m.p.=112° C.

D) 5-Amino-1-(tert-butoxycarbonylmethyl)-2-indolecarboxylic acid 16 g of the compound obtained in the above step are hydrogenated in 200 ml of DMF, at ambient pressure and temperature in the presence of 200 mg of 5% Pd/C. The catalyst is filtered off on Celite®, the solvent is evaporated off and the residue is then triturated from the minimum amount of DCM, to give 10.1 g of the expected compound: m.p.=128° C.

E) 5-(N-tert-Butoxycarbonylamino)-1-(tert-butoxycarbonylmethyl)-2-indolecarboxylic acid 2 g of the compound obtained in the above step are placed in a solution containing 30 ml of dioxane, 30 ml of water and 1 ml of $Et_3N$, and 2 g of $Boc_2O$ in 10 ml of dioxane are added dropwise at 80° C. After the evolution of carbon dioxide has ceased, the solvent is evaporated off and the residue is then taken up in EtOAc. This solution is washed with a buffer solution at pH 2 and is then dried over $MgSO_4$ to give 2.44 g of the expected compound: m.p.>300° C.

Working according to the procedures described above, the substituted 2-indolecarboxylic acids described in the table below are prepared.

TABLE 2

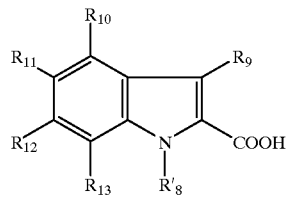

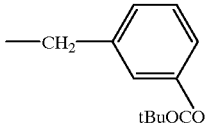

| PREPARATIONS | $R_{10}$ | $R_{11}$ | $R_{12}$ | $R_{13}$ | $R_9$ | $R'_8$ | m.p. ° C. |
|---|---|---|---|---|---|---|---|
| 2.19 | H | H | —OMe | H | H | —$CH_2$COOtBu | 203 |
| 2.20 | H | H | H | H | H | —$CH_2$—C$_6$H$_4$—OCOtBu | 172 |
| 2.21 | H | H | H | H | H | —$(CH_2)_3$COOEt | 152 |

TABLE 2-continued

| PREPARATIONS | R₁₀ | R₁₁ | R₁₂ | R₁₃ | R₉ | R'₈ | m.p. °C |
|---|---|---|---|---|---|---|---|
| 2.22 | H | H | H | H | H | 2-(OCOMe)phenyl | 162 |
| 2.23 | H | H | H | H | H | 3-(EtOCO)phenyl | 206 |
| 2.24 | H | Cl | H | H | H | —CH₂-(2-CO₂Et)phenyl | 199–200 |
| 2.25 | H | Me | H | H | H | —CH₂-(2-CO₂tBu)phenyl | 203–204 |
| 2.26 | —OMe | H | —OMe | H | H | —CH₂CO₂tBu | 210 |
| 2.27 | Me | H | H | H | H | —(CH₂)₄CO₂Et | 108 |
| 2.28 | Me | H | H | H | H | —CH₂CO₂tBu | 175–180 |
| 2.29 | H | OMe | OMe | H | H | —CH₂CO₂tBu | 209–211 |
| 2.30 | H | H | H | H | H | —(CH₂)₄CO₂Et | 79 |
| 2.31 | Me | H | H | H | H | —(CH₂)₅CO₂Et | 85 |
| 2.32 | Me | Me | H | H | H | —CH₂CO₂tBu | 198 |
| 2.33 | H | Cl | H | H | H | —(CH₂)₂CO₂Me | 171 |
| 2.34 | H | Cl | H | H | H | —(CH₂)₃CO₂Et | 152 |
| 2.35 | H | Cl | H | H | H | —(CH₂)₄CO₂Et | 99 |
| 2.36 | H | Me | H | H | H | —(CH₂)₂CO₂Me | 166 |
| 2.37 | OMe | Me | OMe | H | H | —CH₂CO₂tBu | 228 |
| 2.38 | H | OMe | H | H | H | —CH₂CO₂tBu | 170 |
| 2.39 | H | OMe | H | H | H | —(CH₂)₂CO₂Me | 157 |
| 2.40 | Me | H | H | H | H | —(CH₂)₂CO₂Me | 131 |
| 2.41 | Me | H | H | H | H | —(CH₂)₃CO₂Et | 132 |
| 2.42 | H | Me | H | H | H | —(CH₂)₄CO₂Et | 96 |
| 2.43 | Me | H | Me | H | H | —CH₂CO₂tBu | 189 |
| 2.44 | H | Br | H | H | H | —CH₂CO₂Et | 190 |
| 2.45 | H | OMe | OMe | OMe | H | —CH₂CO₂tBu | 170 |
| 2.46 | Me | H | H | Me | H | —CH₂CO₂tBu | 191 |
| 2.47 | Cl | H | H | H | H | —CH₂CO₂tBu | 165 |
| 2.48 | H | Me | H | H | H | —(CH₂)₅CO₂Et | 88 |
| 2.49 | OMe | H | H | H | H | (CH₂)₂CO₂Me | 172 |
| 2.50 | H | F | H | Me | H | —CH₂CO₂tBu | 251 |
| 2.51 | H | H | H | F | H | —CH₂CO₂tBu | 186 |
| 2.52 | H | Cl | H | Me | H | —CH₂CO₂Et | 215 |
| 2.53 | H | Me | H | Cl | H | —CH₂CO₂Et | 191 |
| 2.54 | H | OMe | H | Me | H | —CH₂CO₂tBu | 192 |
| 2.55 | OMe | H | H | OMe | H | —CH₂CO₂tBu | 207 |
| 2.56 | H | H | H | Me | H | —CH₂CO₂tBu | 176 |
| 2.57 | F | H | H | H | H | —CH₂CO₂tBu | 172 |
| 2.58 | H | Me | H | H | Me | —CH₂CO₂tBu | 190 |
| 2.59 | H | Me | H | H | Me | (CH₂)₃CO₂Et | 159 |
| 2.60 | H | H | —SMe | H | H | —CH₂CO₂Et | gum |
| 2.61 | H | Cl | H | Cl | H | —CH₂CO₂Et | 181 |

TABLE 2-continued

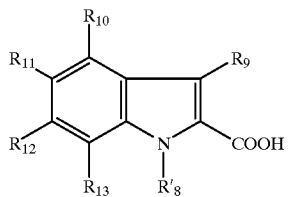

| PREPARATIONS | $R_{10}$ | $R_{11}$ | $R_{12}$ | $R_{13}$ | $R_9$ | $R'_8$ | m.p. °C. |
|---|---|---|---|---|---|---|---|
| 2.62 | H | Cl | H | H | Me | —$CH_2CO_2Me$ | 216 |
| 2.63 | Me | H | Me | H | H | —$(CH_2)_3CO_2Et$ | gum |
| 2.64 | H | H | H | OMe | H | —$(CH_2)_3CO_2Et$ | 115 |
| 2.65 | H | H | H | OMe | H | —$CH_2CO_2tBu$ | 192 |
| 2.66 | H | H | H | H | Me | —$CH_2CO_2tBu$ | 175 |
| 2.67 | H | F | H | H | H | —$CH_2CO_2tBu$ | 173 |
| 2.68 | H | Me | H | H | H | —$CH_2CO_2Et$ | 197 |
| 2.69 | H | OCOMe | H | H | H | —$CH_2CO_2tBu$ | 185 |
| 2.70 | Me | Cl | H | H | H | —$CH_2CO_2Et$ | 174 |
| 2.71 | Me | H | H | Cl | H | —$CH_2CO_2Et$ | 150 |
| 2.72 | H | Cl | H | F | H | —$CH_2CO_2Et$ | 187 |
| 2.73 | Me | H | H | Me | H | —$CH_2CO_2Et$ | 220 |
| 2.74 | H | Me | H | F | H | —$CH_2CO_2Me$ | 167 |
| 2.75 | H | Cl | H | Cl | H | —$CH_2CO_2Et$ | 165 |
| 2.76 | OCOMe | H | H | H | H | —$CH_2CO_2tBu$ | 179 |

C—Preparation of Substituted Pyrrolotyridinecarboxylic Acids of Formula R'$_3$COOH:

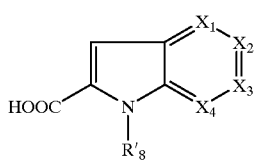

(III)

in which R'$_8$ is the precursor of R$_8$ and the groups X$_1$, X$_2$, X$_3$ and X$_4$ are as defined above for (I).

Preparation 3.1

1-tert-Butoxycarbonylmethyl-1H-pyrrolo[3,2-c]-pyridine-2-carboxylic acid

A) Benzyl 1H-pyrrolo[3,2-c]pyridine-2-carboxylate 40 ml of 1.7M tert-butyllithium in pentane are added, at −40° C. under nitrogen, to 5 g of 4-(N-Bocamino)-3-methylpyridine. After stirring for 1 hour at −40° C., the lithiated derivative thus formed is added to 12.9 g of benzyl oxalate in 100 ml of THF at −40° C. The mixture is allowed to return to 0° C., it is left stirring for 2 hours, 25 ml of 6N HCl are then added and this mixture is heated at 50° C. for one and a half hours. The pH is brought to 9 by addition of 1N NaOH, the mixture is then extracted with EtOAc and the extracts are dried and evaporated. The residue is chromatographed on silica, eluting with DCM/MeOR (100/3; v/v) to give 2.7 g of the expected compound.

B) Benzyl 1-tert-butoxycarbonylmethyl-1H-pyrrolo-[3,2-c]pyridine-2-carboxylate 0.29 g of sodium hydride at 60% in oil is added to 20 ml of DMF under nitrogen, followed by addition, at 10° C., of 1.7 g of the compound obtained in the above step. After stirring for 45 minutes, 1.43 g of tert-butyl bromoacetate are added. The mixture is allowed to return to RT and is stirred for 5 hours, the reaction medium is then poured into water and extracted with ether, and the extracts are dried and then evaporated. The yellow oil obtained is chromatographed on silica, eluting with DCM/MeOH (100/3; v/v) and the fractions containing the product are then combined and chromatographed again on silica, eluting with cyclohexane/EtOAc (1/1; v/v). 1 g of yellow crystals is obtained: m.p.= 94° C.

C) 1-tert-Butoxycarbonylmethyl-1H-pyrrolo-[3,2-c]pyridine-2-carboxylic acid

A catalytic hydrogenation is carried out in the presence of 170 mg of 10% Pd/C at room temperature and pressure for 4 hours, on 1 g of the compound obtained in the above step. The precipitate formed is dissolved in DMF, the Pd/C is then filtered off on Celite®, the filtrate is evaporated to dryness and the crystals are then washed with Et$_2$O to give 0.39 g of the expected compound: m.p.=265° C.

Preparation 3.2

1-tert-Butoxycarbonylmethyl-5-methoxy-1H-pyrrolo [2,3-c]pyridine-2-carboxylic acid A) 5-(N-Boc-amino)-2-methoxy-4-methylpyridine 41.7 ml of 1.6M n-butyllithium in hexane and 7.7 g of TMEDA are added, under nitrogen, to 5 g of 5-(N-Boc-amino)-2-methoxypyridine, at −60° C. The medium turns yellow. The mixture is left stirring for 4 hours, allowing the temperature to return to −10° C., and a pale yellow. precipitate forms. The mixture is recooled to −40° C. and 4.7 g of methyl iodide are then added. The medium is allowed to return to RT and is then poured into water and extracted with EtOAc, and the extracts are dried and evaporated. The residue is chromatographed on silica, eluting with cyclohexane/EtOAc (85/15; v/v).

B) Benzyl 5-methoxy-1H-pyrrolo[2,3-c]pyridine-2-carboxylate 13.8 ml of 1.6M n-butyllithium in hexane are added, at −60° C. under nitrogen, to 2.4 g of the compound from the above step. The mixture is allowed to warm to −20° C. and is stirred for 30 minutes. The lithiated derivative thus formed is added to 5.4 g of benzyl oxalate and this mixture is left stirring for 2 hours at RT. It is poured into water and extracted with EtOAc, and the extracts are dried and then evaporated. The residue is taken up in 100 ml of THF, 30 ml of 6N HCl are then added and the mixture is heated at 50° C. for one and a half hours. The pH is brought to 6 by addition of 1N HCl, this mixture is extracted with DCM and the extracts are dried and then evaporated. The residue is chromatographed on silica, eluting with DCM/MeOH (100/2.5; v/v). 0.9 g of the expected compound is obtained: m.p.=182° C.

C) Benzyl 1-tert-butoxycarbonylmethyl-5-methoxy-1H-pyrrolo[2,3-c]pyridine-2-carboxylate 0.9 g of the compound from the above step is added, at 5° C., to 0.14 g of NaH at 60% in oil in 10 ml of DMF, the mixture is left stirring for 15 minutes and 0.68 g of tert-butyl bromoacetate is then added at RT. After stirring for 5 hours at RT, the mixture is poured into water and extracted with $Et_2O$, and the extracts are dried and then evaporated. The residue is chromatographed on silica, eluting with DCM/EtOAc (100/1; v/v). 1.2 g of the expected compound are obtained: m.p.=110° C.

D) 1-tert-Butoxycarbonylmethyl-5-methoxy-1H-pyrrolo[2,3-c]pyridine-2-carboxylic acid 1.2 g of the compound from the above step, dissolved in an EtOH/DMF mixture, is hydrogenated for 3 hours, at room temperature and pressure, in the presence of 120 mg of 10% Pd/C. The Pd/C is filtered off on Celite®, the filtrate is evaporated to dryness and the residue is then chromatographed on silica, eluting with DCM/MeOH (100/3; v/v). 0.41 g of the expected compound is obtained in the form of a white foam.

Preparation 3.3

1-tert-Butoxycarbonylmethyl-1H-pyrrolo[2,3-b]-pyridine-2-carboxylic acid

A) Ethyl 1-H-pyrrolo[2,3-b]pyridine-2-carboxylate 30 ml of n-butyllithium are added, under nitrogen, at a temperature of less than 5° C., to 5 g of 2-(N-Boc)amino-3-methylpyridine in 100 ml of THF. After stirring for 1 hour at 0° C., the lithiated derivative thus formed is added to a solution of 7 g of ethyl oxalate in 50 ml of THF at −3° C. The reaction medium is allowed to return to RT and is then poured slowly into 25 ml of 6N HCl at 0° C., while maintaining the temperature below 100° C. This mixture is heated at 50° C. for 2 hours and the pH is then brought to 3 by addition of 1N NaOH. This mixture is extracted with $Et_2O$ and the organic phase is taken up in $K_2CO_3$ solution and then dried and evaporated to give 1.8 g of the expected compound in the form of white crystals: m.p.=162° C.

B) 1H-Pyrrolo[2,3-b]pyridine-2-carboxylic acid

A mixture containing 2.4 g of the compound obtained in the above step and 2.5 g of sodium hydroxide is left stirring for 3 hours in an ethanol/water mixture (20/20; v/v). The precipitate formed is filtered off and then dissolved in water. By acidifying to pH=4 with AcOH, a white precipitate forms, which is washed with water and then dried to give 1.3 g of the expected compound: m.p.>260° C.

C) Benzyl 1H-pyrrolo[2,3-b]pyridine-2-carboxylate

A mixture containing 1.3 g of the compound obtained in the above step, 1.22 g of DBU and 1.37 g of benzyl bromide in 30 ml of DMF is left stirring at RT for 2 hours. After evaporation of the solvent, the residue is taken up in DCM and water and then extracted with a buffer solution at pH=2. The resulting solution is dried and then evaporated and the crystals formed are washed with heptane to give 1.5 g of the expected compound: m.p.=176° C.

D) Benzyl 1-tert-butoxycarbonylmethyl-1H-pyrrolo[2,3-b]pyridine-2-carboxylate

This compound is obtained by working as in step C of the above preparation.

E) 1-tert-Butoxycarbonylmethyl-1H-pyrrolo-[2,3-b]pyridine-2-carboxylic acid

This compound is obtained by hydrogenation in the presence of Pd/C: m.p.=104° C.

EXAMPLE 1

2-(5-Cyclohexylethyl-4-(2,5-dimethoxy-4-methylphenyl)-2-thiazolylcarbamoyl)-5-methyl-1-indoleacetic acid trifluoroacetic acid

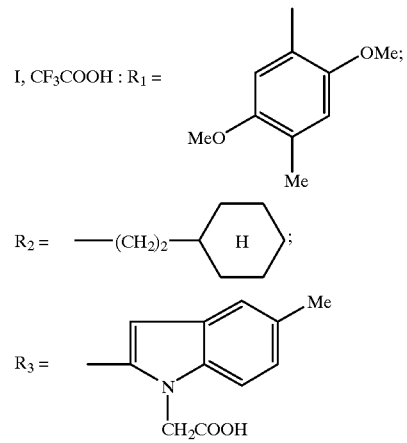

A) tert-Butyl 2-(5-cyclohexylethyl-4-(2,5-dimethoxy-4-methylphenyl)-2-thiazolylcarbamoyl)-5-methyl-1-indoleacetate 0.505 g of the compound of Preparation 1.1, 0.45 g of the compound of Preparation 2.3, 0.75 g of BOP and 0.17 g of triethylamine are mixed together in 2 ml of DMF. After stirring for 11 days at RT, the mixture is poured onto 150 ml of sulphate buffer. The precipitate formed is filtered off and then washed with water, after which it is dissolved in DCM and the solution is dried over $Na_2SO_4$ and concentrated. The residue is chromatographed on silica H, eluting with a DCM/EtOAc mixture (100/1; v/v) to give 0.41 g of the expected compound.

B) 2-(5-Cyclohexylethyl-4-(2,5-dimethoxy-4-methylphenyl)-2-thiazolylcarbamoyl)-5-methyl-1-indoleacetic acid trifluoroacetic acid 0.41 g of the compound from the above step is dissolved in 15 ml of TFA. After stirring for 4 hours at 10° C., the mixture is concentrated under vacuum. The residue is taken up in 250 ml of water and is then left stirring for 1 hour at RT. The white precipitate formed is filtered off and then dried to give 0.37 g of the expected product: m.p.=140° C.

EXAMPLE 1a

Sodium 2-(5-cyclohexylethyl-4-(2,5-dimethoxy-4-methylphenyl)-2-thiazolylcarbamoyl)-5-methyl-1-indoleacetate. sodium trifluoroacetate A suspension of 0.47 g of the compound obtained in Example 1 in 200 ml of absolute EtOH is heated to reflux, 0.68 ml of 2N NaOH solution is added and the mixture is left stirring for 10 minutes at reflux. It is concentrated under vacuum, the residue is taken up in ether and the crystalline product formed is filtered off and washed with ether. 0.36 g of the expected product is obtained: m.p.=170° C.

EXAMPLE 2

2-(5-cyclohexylethyl-4-(2,5-dimethoxy-4-methylphenyl)-2-thiazolylcarbamoyl)-4-methoxy-1-indoleacetic acid. hydrochloric acid

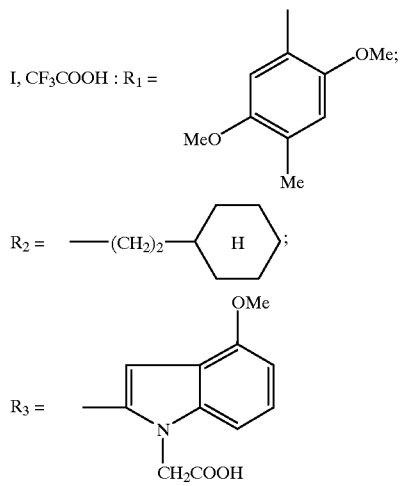

A) tert-Butyl 2-(5-cyclohexylethyl-4-(2,5-dimethoxy-4-methylphenyl)-2-thiazolylcarbamoyl)-4-methoxy-1-indoleacetate 0.505 g of the compound of Preparation 1.1, 0.47 g of the compound of Preparation 2.4, 0.75 g of BOP and 0.17 g of triethylamine are mixed together in 2 ml of DMF. After stirring for 5 days at RT, 50 ml of sulphate buffer are added. The precipitate formed is dissolved in DCM and is then dried over $Na_2SO_4$ and concentrated. The residue is chromatographed on silica, eluting with DCM/EtOAc (100/2; v/v) to give 0.9 g of the expected product in the form of an oil.

B) 2-(5-Cyclohexylethyl-4-(2,5-dimethoxy-4-methylphenyl)-2-thiazolylcarbamoyl)-4-methoxy-1-indoleacetic acid. hydrochloric acid 0.9 g of the compound from the above step is dissolved in 10 ml of DCM, followed by addition of 10 ml of TFA at 10° C., and the mixture is left stirring for 4 hours at 10° C. This mixture is concentrated under vacuum, the residue is taken up in 100 ml of ether and the resulting solution is then extracted twice with 25 ml of 2N NaOH. The aqueous phase is acidified with 55 ml of 2N HCl and the precipitate formed is then filtered off. It is washed with water and then dried to give 0.68 g of the expected compound: m.p.=150° C.

EXAMPLE 3

Sodium 2-((5-cyclohexylethyl)-4-(2,5-dimethoxy-4-methylphenyl)-2-thiazolylcarbamoyl)-1-indoleacetate

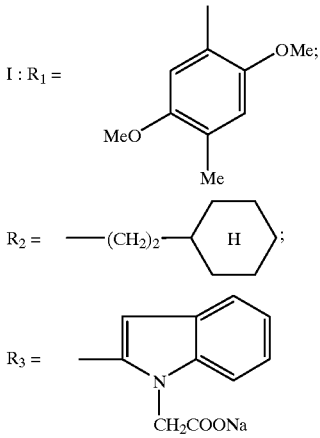

A) Methyl 2-((5-cyclohexylethyl)-4-(2,5-dimethoxy-4-methylphenyl)-2-thiazolylcarbamoyl)-1-indoleacetate 0.976 g of the compound of Preparation 1.1, 0.7 g of 1-methoxycarbonylmethylindole-2-carboxylic acid (Preparation 2.1), 1.44 g of BOP and 0.33 g of triethylamine are mixed together in 30 ml of DCM. After stirring for 3 days at RT, 30 ml of sulphate buffer are added, the phases are separated by settling, and the organic phase is dried over $Na_2SO_4$ and then concentrated. The residue is chromatographed on silica, eluting with DCM/MeOH (100/0.2; v/v). 1.52 g of the expected compound are obtained: m.p.= 144–146° C.

B) Sodium 2-((5-cyclohexylethyl)-4-(2,5-dimethoxy-4-methylphenyl)-2-thiazolylcarbamoyl)-1-indoleacetate 0.5 g of the compound from the above step is dissolved in 30 ml of dioxane, and 10 ml of 2-propanol and 0.9 g of 30% sodium hydroxide are added. After stirring for 15 hours at RT, the solvent is evaporated off. The residue is taken up in iPrOH; the crystals formed are filtered off, washed with iPrOH, with ethyl ether and then dried in an oven. 0.46 g of the expected compound is obtained: m.p.>350° C. The sodium salt crystallizes with one molecule of NaOH.

EXAMPLE 4

2-((5-Cyclohexylethyl)-4-(2,5-dimethoxy-4-methylphenyl)-2-thiazolylcarbamoyl)-1-indoleacetic acid

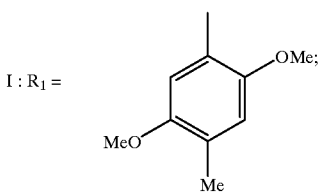

-continued

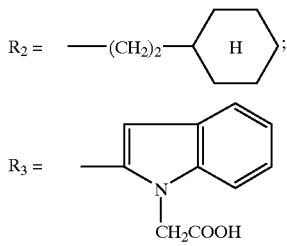

0.7 g of the compound from Preparation 1.1, 0.53 g of 1-tert-butoxycarbonylmethyl-2-indolecarboxylic acid (Preparation 2.2), 0.85 g of BOP and 0.25 ml of triethylamine are mixed together in 3 ml of DMF. After stirring overnight at RT, sulphate buffer is added. The crystals formed are filtered off and taken up in DCM. The organic phase is washed with sulphate buffer and then with $Na_2CO_3$ solution and dried over $MgSO_4$. The residue is chromatographed on silica, eluting with a DCM/EtOAc mixture (100/1; v/v). The pure product obtained is taken up in 10 ml of TFA and stirred for 3 hours. After evaporation, the residue is taken up in water and $Na_2CO_3$ solution, and then concentrated hydrochloric acid is added to pH=5. This mixture is extracted with DCM and then dried over $MgSO_4$ to give 0.42 g of the expected compound: m.p.=198° C.

EXAMPLE 5

2-(4-(4-Chloro-2,5-dimethoxyphenyl)-5-(2-cyclohexylethyl)-2-thiazolylcarbamoyl)-5,7-dimethyl-1-indoleacetic acid trifluoroacetic acid.

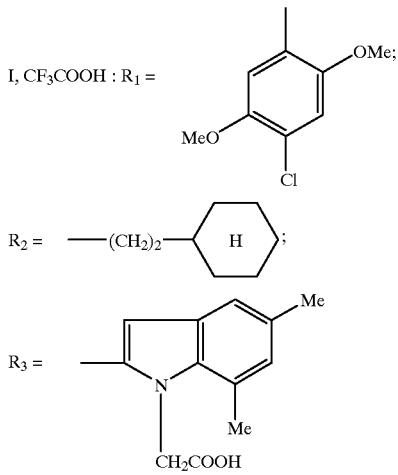

A) tert-Butyl 2-(4-(4-chloro-2,5-dimethoxyphenyl)-5-cyclohexylethyl)-2-thiazolylcarbamoyl)-5,7-dimethyl-1-indoleacetate 250 mg of the compound from Preparation 2.13, 314 mg of the compound from Preparation 1.4, 0.34 mg of triethylamine and 365 mg of BOP are mixed together in 10 ml of DCM and the mixture is left stirring for 3 days at RT. It is extracted with ether, the extracts are washed with water and with saturated $KHSO_4$ solution, then the solvents are evaporated off and dried over $Na_2SO_4$. The residue is chromatographed on silica, eluting with DCM/EtOAc (30/20; v/v). 218 mg of the expected compound are obtained.

B) 2-(4-(4-Chloro-2,5-dimethoxyphenyl)-5-cyclohexylethyl-2-thiazolylcarbamoyl)-5,7-dimethyl-1-indoleacetic acid. trifluoroacetic acid 218 mg of the compound from the above step are mixed with 2.5 ml of TFA in 6 ml of DCM and the mixture is left stirring for 3 hours at RT. The reaction medium is concentrated, the residue is taken up in ether and the precipitate obtained is filtered off to give 160 mg of the expected compound: m.p.=173° C.

EXAMPLE 5a

Potassium 2-(4-(4-chloro-2,5-dimethoxyphenyl)-5-cyclohexylethyl-2-thiazolylcarbamoyl)-5,7-dimethyl-1-indoleacetate trihydrate

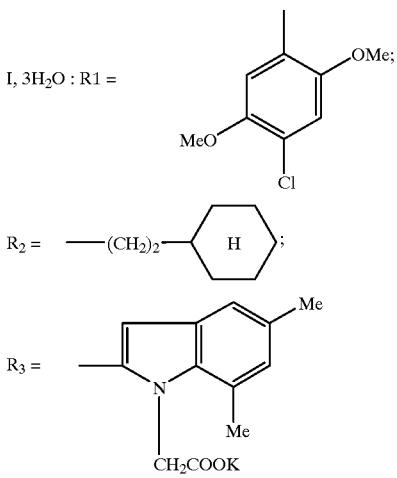

A) Methyl 2-(4- (4-chloro-2,5-dimethoxyphenyl)-5-cyclohexylethyl-2-thiazolylcarbamoyl)-5,7-dimethyl-1-indoleacetate 5.9 g of the compound from Preparation 2.13a, 7.82 g of the compound from Preparation 1.4, 2.5 g of triethylamine and 10.9 g of BOP are mixed together in 35 ml of DMF and the mixture is left stirring for 48 hours at RT. It is poured into 2 litres of sulphate buffer and the precipitate formed is filtered off and washed with water. The precipitate is dissolved in 400 ml of EtOAc, washed successively twice with 250 ml of saturated $Na_2CO_3$ solution, 150 ml of sulphate buffer solution and 150 ml of saturated NaCl solution. The organic phase is dried over $Na_2SO_4$ and evaporated. The residue is chromatographed on silica, eluting with a methylene chloride/ethyl acetate mixture (98/2; v/v). The crystals obtained are washed with isopropyl ether. 11.6 g of the expected product is obtained: m.p.=202° C.

B) Potassium 2-(4-(4-chloro-2,5-dimethoxyphenyl)-5-cyclohexylethyl-2-thiazolylcarbamoyl)-5,7-dimethyl-1-indoleacetate trihydrate A mixture of 2 g of the product obtained in step A, 1.33 g of $K_2CO_3$ in 4.6 ml of water and 8 ml of n-butanol is heated at 90° C. for 9 hours. After cooling to RT, water is added and the precipitate formed is filtered off, washed with water (3×50 ml) and then with ethyl ether (3×200 ml) and dried under vacuum. 1.2 g of the expected product is obtained: m.p.=250° C.

EXAMPLE 5b 2-(4-(4-Chloro-2,5-dimethoxyphenyl)-5-cyclohexylethyl-2-thiazolylcarbamoyl)-5,7-dimethyl-1-indoleacetic acid I: R$_1$ = 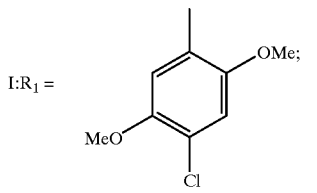

R$_2$ = 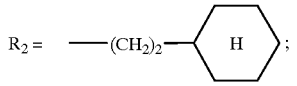

R$_3$ = 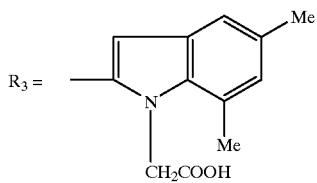

A mixture of 4 g of the compound obtained in step A of Example 5a, 2.65 g of K$_2$CO$_3$ in 9.2 ml of water and 16 ml of n-butanol is heated at 90° C. for 12 hours. After cooling to RT, 19.2 ml of 2N HCl are added. The white precipitate formed is washed with 3 times 200 ml of water and then 3 times 200 ml of ethyl ether. 3.1 g of the expected product are obtained: m.p.=241° C.

EXAMPLE 5c

Sodium 2-(4-(4-chloro-2,5-dimethoxyphenyl)-5-cyclohexylethyl-2-thiazolylcarbamoyl)-5,7-dimethyl-1-indoleacetate sesquihydrate: m.p.=200° C.

EXAMPLES 6 and 7

Sodium 2-(4-(4-chloro-2,5-dimethoxyphenyl)-5-cyclohexylethyl-2-thiazolylcarbamoyl)-1-indoleacetate and 2-(4-(4-chloro-2,5-dimethoxyphenyl)-5-cyclohexylethyl-2-thiazolylcarbamoyl)-1-indoleacetic acid I: R$_1$ = 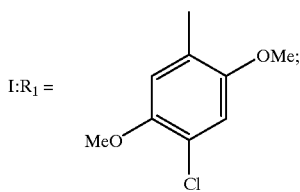

R$_2$ = 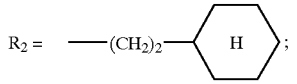

R$_3$ = 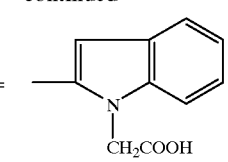

The process is performed according to the procedure described in Example 3, step A, starting with the compounds of Preparations 1.4 and 2.1 to prepare methyl 2-(4-(4-chloro-2,5-dimethoxyphenyl)-5-(cyclohexylethyl)-2-thiazolylcarbamoyl)-1-indoleacetate: m.p.=145° C. (step A). Working as in step B. the sodium salt of the expected compound is prepared (Example 6), which crystallizes with one molecule of NAOH: m.p.=252° C.

2 ml of 2N NaOH are added to a suspension of 0.7 g of the ester obtained in step A in 30 ml of methanol. The solution formed is left to stand for 18 hours and the methanol is then evaporated off. The residue is taken up in water and then acidified by addition of concentrated HCl to pH=2. After stirring for 1 hour, the precipitate formed is filtered off, washed with water and dried in an oven. 0.63 g of the expected acid is obtained (Example 7): m.p.=213° C.

EXAMPLE 8

2-(5-Cyclohexylethyl-4-(2,5-dimethoxy-4-chlorophenyl)-2-thiazolylcarbamoyl)-1-indolehexanoic acid I: R$_1$ = 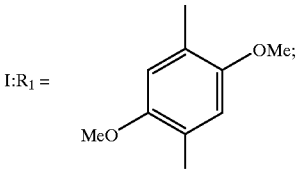

R$_2$ = 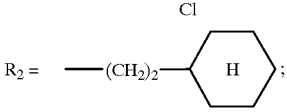

R$_3$ = 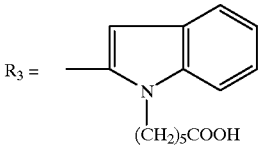

0.88 g of the compound from Preparation 1.4, 0.7 g of the compound from Preparation 2.12, 1.2 g of BOP and 0.32 ml of triethylamine are placed in 3 ml of DMF and stirred overnight. Sulphate buffer is added; the precipitate formed is filtered off and taken up in EtOAc. This solution is washed with sulphate buffer, with Na$_2$CO$_3$ solution and then dried over MgSO$_4$. The residue is chromatographed on silica H, eluting with a DCM/EtOAc mixture (100/2; v/v). The product obtained is saponified in 10 ml of ethanol and 2 ml of 4N NaOH. The solvent is evaporated off and the residue is taken up in water and then acidified to pH=2 by addition of concentrated HCl. The precipitate formed is filtered off to give 1.21 g of the expected compound: m.p.=121° C.

EXAMPLE 9

2-(5-Cyclohexylethyl-4-(2,5-dimethoxy-4-methylphenyl)-2-thiazolylcarbamoyl)-1-indolebutyric acid

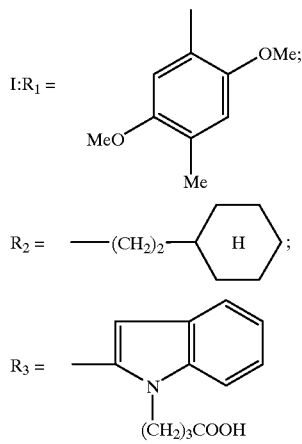

A mixture of 0.6 g of the compound from Preparation 2.21, 0.75 g of the compound from Preparation 1.1, 1 g of BOP and 0.3 ml of triethylamine is left stirring for 4 hours in 3 ml of DMF. Sulphate buffer is added and the precipitate formed is filtered off. This precipitate is taken up in EtOAc and the solution is washed with sulphate buffer, with $Na_2CO_3$ solution and then dried over $MgSO_4$ and concentrated under vacuum. The residue is chromatographed on silica H, eluting with a DCM/EtOAc mixture (100/1; v/v). The product obtained is saponified in 10 ml of ethanol and 2 ml of 4N NaOH. The solvent is evaporated off and the residue is then triturated from water and a few drops of concentrated HCl, and the precipitate obtained is filtered off and dried. 0.82 g of the expected compound is obtained: m.p.=223° C.

Working according to the procedures described in the above examples, the compounds according to the invention collated in Table 3 are prepared, from the compounds obtained in the preparations.

TABLE 3

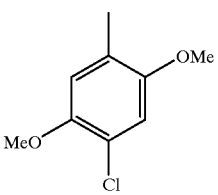

| Examples | $R_1$ | $R_2$ | $R_8$ | $R_9$, $R_{10}$, $R_{11}$, $R_{12}$, $R_{13}$ | m.p. °C. Salt or solvate |
|---|---|---|---|---|---|
| 10 | 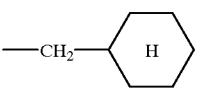 | 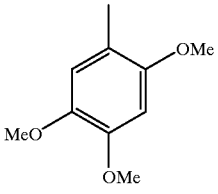 | $CH_2CO_2H$ | H | 223 |
| 11 | 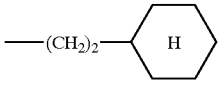 | 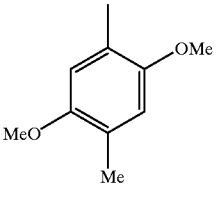 | —$CH_2CO_2H$ | H | 210 |
| 12 | 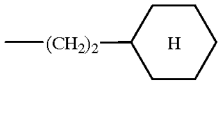 | 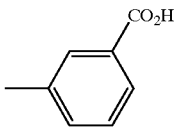 | [3-carboxyphenyl] | H | 190 |

TABLE 3-continued
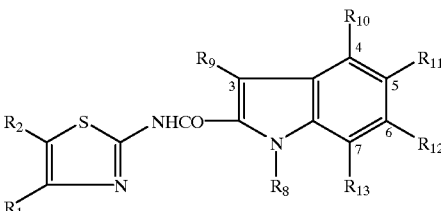
| Examples | R₁ | R₂ | R₈ | R₉, R₁₀, R₁₁, R₁₂, R₁₃ | m.p. °C. Salt or solvate |
|---|---|---|---|---|---|
| 13 | 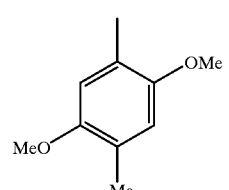 | —(CH₂)₂—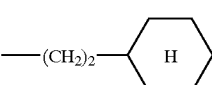 | —(CH₂)₂CO₂H | H | 150 |
| 14 | 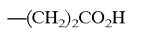 | —(CH₂)₂—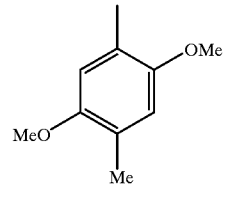 | 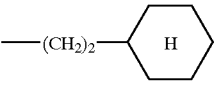 | H | 170 |
| 15 | 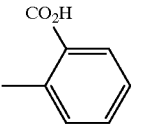 | —(CH₂)₂—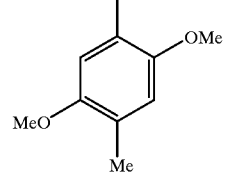 | 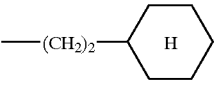 | H | 180 |
| 16 | 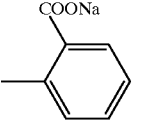 | —(CH₂)₂—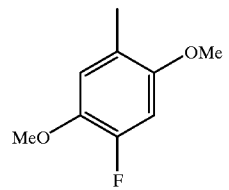 | —CH₂CO₂H | H | 184 |
| 17 | 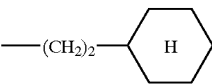 | —(CH₂)₂— | CH₂CO₂H | H | 170 |
| 18 | 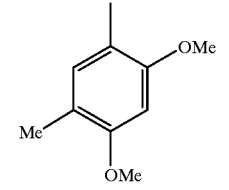 | —(CH₂)₂—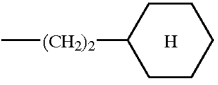 | —CH₂CO₂H | H | 215 |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 19 | 2,5-dimethoxy-4-methylphenyl (Me, OMe, MeO, Me) | —(CH₂)₅CH₃ | CH₂CO₂H | H | 242 |
| 20 | 2,5-dimethoxy-4-methylphenyl | —(CH₂)₂-cyclopentyl | —CH₂CO₂H | H | 250 |
| 21 | methylenedioxy-methoxy-methylphenyl | —(CH₂)₂-cyclohexyl | —CH₂CO₂H | H | 180 |
| 22 | 2,5-dimethoxy-4-methylphenyl | —(CH₂)₂-cycloheptyl | —CH₂CO₂Na | H | 242 |
| 23 | 2,5-dimethoxy-4-methylphenyl | —(CH₂)₂-cycloheptyl | —CH₂CO₂H | H | 236 |
| 24 | 2-methoxy-4-methoxy-5-ethyl-phenyl | —(CH₂)₂-cyclohexyl | —CH₂CO₂H | H | 234 |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 25 | 2-OMe, 5-OEt, 4-Me, phenyl (Me at position shown) | —(CH₂)₂-cyclohexyl | —CH₂CO₂H | H | 197 |
| 26 | 2-OMe, 5-OMe, 4-Cl, phenyl-Me | —(CH₂)₂-cyclohexyl | —(CH₂)₂CO₂H | H | 283 |
| 27 | 2-OMe, 5-OMe, 4-Cl, phenyl-Me | —(CH₂)₂-cyclohexyl | —(CH₂)₃CO₂H | H | 160 |
| 28 | 2,6-di-OMe, 4-Me phenyl-Me | —(CH₂)₂-cyclohexyl | —CH₂CO₂H | H | 228 |
| 29 | 2-OMe, 5-OMe, 4-Me phenyl-Me | —(CH₂)₂-cyclohexyl | CH₂CO₂H | 6-OMe | 140 |
| 30 | 2-OMe, 5-OMe, 4-Me phenyl-Me | —S—CH₂-cyclopentyl | —CH₂CO₂H | H | 216 |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 31 | 2-Me,4-OMe,5-OMe,Me-phenyl | —(CH₂)₄CH(CH₃)₂ | —CH₂CO₂Na | H | 210 |
| 32 | 2-Me,4-OMe,5-OMe,Me-phenyl | —(CH₂)₂-(4,4-diMe-cyclohexyl) | —CH₂CO₂H | H | 160 |
| 33 | 2-Me,4-OMe,5-OMe,Me-phenyl | —(CH₂)₆CH₃ | —CH₂CO₂H | H | 206 HCl |
| 34 | 2-Me,4-OMe,5-OMe,Me-phenyl | —CH₂—S-cyclohexyl | —CH₂CO₂H | H | 213 |
| 35 | 2-Me,4-OMe,5-OMe,Cl-phenyl | —(CH₂)₂-cyclohexyl | —(CH₂)₄CO₂H | H | 232 |
| 36 | 2-Me,4-OMe,5-OMe,Me-phenyl | —(CH₂)₂-cyclohexyl | —CH₂CO₂H | 4-CH₃ | 140 CF₃CO₂H |

TABLE 3-continued

[Structure: R2-thiazole(R1)-NHCO-indole with R8 on N, R9 at 3, R10 at 4, R11 at 5, R12 at 6, R13 at 7]

| Examples | R₁ | R₂ | R₈ | R₉, R₁₀, R₁₁, R₁₂, R₁₃ | m.p. °C. Salt or solvate |
|---|---|---|---|---|---|
| 37 | 2,5-diOMe-4-Me-phenyl (Me top) | —(CH₂)₂-cyclohexyl | H | —CH₂CO₂Na | 4-CH₃ | 240 |
| 38 | 2,5-diOMe-4-Me-phenyl | —(CH₂)₂-cyclohexyl | H | —(CH₂)₅CO₂H | H | 118 |
| 39 | 2-OMe-4-Cl-5-OMe-phenyl (Me top) | —(CH₂)₂-cyclohexyl | H | —CH₂CO₂H | 4-CF₃ | 200 |
| 40 | 2,5-diOMe-4-Me-phenyl | —(CH₂)₂-cyclohexyl | H | —CH₂CO₂H | 4,6-diOMe | 210 |
| 41 | 2-OMe-4-Cl-5-OMe-phenyl (Me top) | —(CH₂)₂-cyclohexyl | H | —CH₂CO₂H | 5-Et | 220 CF₃CO₂H |
| 42 | 2,5-diOMe-4-Me-phenyl | —(CH₂)₂-cyclohexyl | H | —CH₂CO₂H | 5,6-diOMe | 180 CF₃CO₂H |

TABLE 3-continued
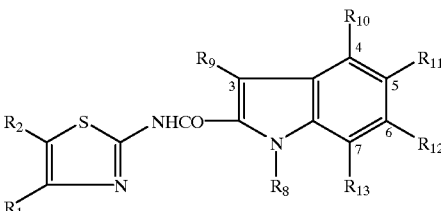
| Examples | R₁ | R₂ | R₈ | R₉, R₁₀, R₁₁, R₁₂, R₁₃ | m.p. °C. Salt or solvate |
|---|---|---|---|---|---|
| 43 | 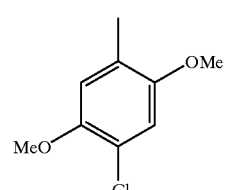 | —(CH₂)₂— 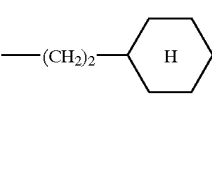 | —CH₂CO₂Na | 5-Me | 220 CF₃CO₂Na |
| 44 | 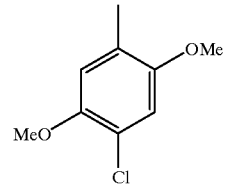 | —(CH₂)₂— 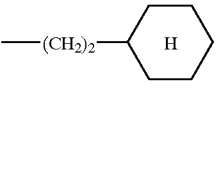 | —CH₂CO₂Na | 4-OMe | 160 CF₃CO₂Na |
| 45 | 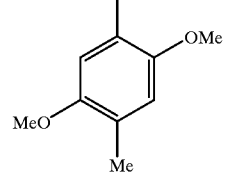 | —(CH₂)₂— 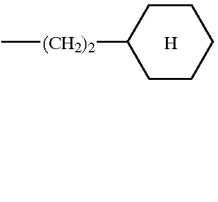 | —CH₂CO₂H | 4-CF₃ | 210 0.75 CF₃CO₂H |
| 46 | 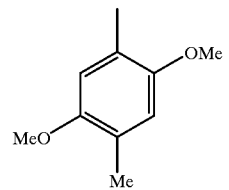 | —(CH₂)₂— 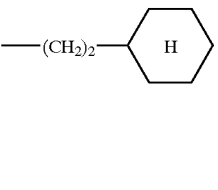 | —CH₂CO₂H | 5-CF₃ | 150 3CF₃CO₂H |
| 47 | 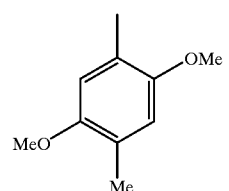 | —(CH₂)₂— 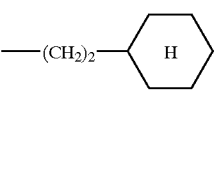 | —CH₂CO₂H | 5-Et | 200 CF₃CO₂H |
| 48 | 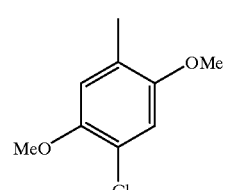 | —(CH₂)₂— 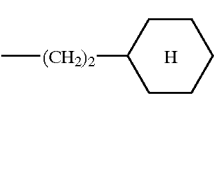 | —CH₂CO₂H | 5,6-diOMe | 180 CF₃CO₂H |

TABLE 3-continued
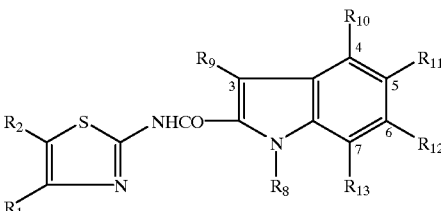
| Examples | R₁ | R₂ | R₈ | R₉, R₁₀, R₁₁, R₁₂, R₁₃ | m.p. °C. Salt or solvate |
|---|---|---|---|---|---|
| 49 | 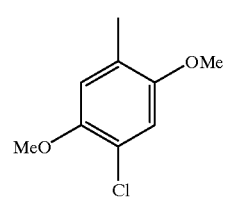 | —(CH₂)₂—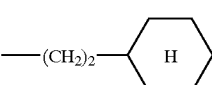H | —(CH₂)₃CO₂H | 5-Me | 207 |
| 50 | 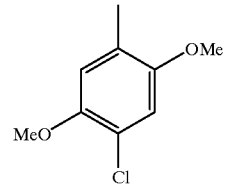 | —(CH₂)₂—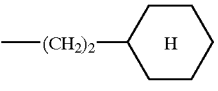H | —CH₂CO₂H | 4-Me | 185 CF₃CO₂H |
| 51 | 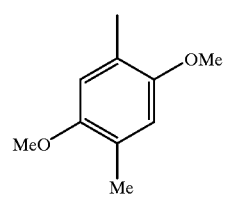 | —(CH₂)₂—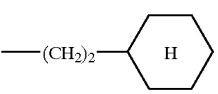H | —(CH₂)₄CO₂H | H | 226 HCl |
| 52 | 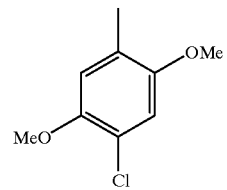 | —(CH₂)₂—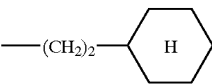H | CH₂CO₂H | 5-CF₃ | 190 2CF₃CO₂H |
| 53 | 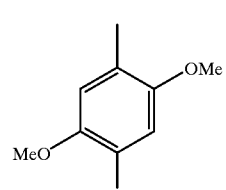 | —SCH₂—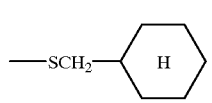H | —CH₂CO₂H | H | 213 |
| 54 | 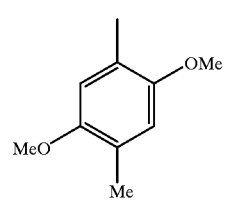 | —(CH₂)₂—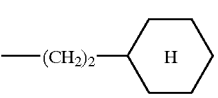H | —CH₂CO₂H | 5-Cl | 170 |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 55 | 2,5-diMeO-4-Me-phenyl | —(CH₂)₂-cyclohexyl | H | —CH₂CO₂H | 4,6-diOMe, 5-Me | 160 CF₃CO₂H |
| 56 | 2,5-diMeO-4-Me-phenyl | —(CH₂)₂-cyclohexyl | H | —(CH₂)₃CO₂H | 5-Cl | 193 HCl |
| 57 | 4-Cl-2-MeO-5-MeO-phenyl | —(CH₂)₂-cyclohexyl | H | —(CH₂)₃CO₂H | 5-Cl | 188 HCl |
| 58 | 4-Cl-2-MeO-5-MeO-phenyl | —(CH₂)₂-cyclohexyl | H | —(CH₂)₃CO₂H | 4-Me | 163 |
| 59 | 2,5-diMeO-4-Me-phenyl | —(CH₂)₂-cyclohexyl | H | —(CH₂)₂CO₂H | 5-Cl | 275 |
| 60 | 4-Cl-2-MeO-5-MeO-phenyl | —(CH₂)₂-cyclohexyl | H | —(CH₂)₂CO₂H | 4-Me | 298 |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 61 | 2,5-di(OMe)-4-Me-phenyl (with Me at other position) | —(CH₂)₂—cyclohexyl | —CH₂CO₂H | 4,5-diMe | 185 CF₃CO₂H |
| 62 | 4-Cl-2,5-di(OMe)-phenyl (Me) | —(CH₂)₂—cyclohexyl | —CH₂CO₂H | 4,5-diMe | 195 CF₃CO₂H |
| 63 | 4-Cl-2,5-di(OMe)-phenyl (Me) | —(CH₂)₂—cyclohexyl | —CH₂CO₂H | 5-OMe | 160 CF₃CO₂H |
| 64 | 2,5-di(OMe)-4-Me-phenyl (Me) | —(CH₂)₂—cyclohexyl | —CH₂CO₂H | 5,7-diMe | 160 CF₃CO₂H |
| 65 | 4-Cl-2,5-di(OMe)-phenyl (Me) | —SCH₂—cyclohexyl | —(CH₂)₃CO₂H | 4-Me | 140 HCl |
| 66 | 2,5-di(OMe)-4-Me-phenyl (Me) | —(CH₂)₂—cyclohexyl | —(CH₂)₂CO₂H | 3,5-diMe | 223 HCl |

TABLE 3-continued

Structure: thiazole (with R1 at 4-position, R2 at 5-position) — NHCO — indole (positions 3=R9, 4=R10, 5=R11, 6=R12, 7=R13, N=R8, with linkage at 2-position)

| Examples | R₁ | R₂ | R₈ | R₉, R₁₀, R₁₁, R₁₂, R₁₃ | m.p. °C. Salt or solvate |
|---|---|---|---|---|---|
| 67 | 2-OMe-4-Me-5-Cl-phenyl (MeO and Cl para; Me and OMe) | —(CH₂)₂—cyclohexyl | —CH₂CO₂Na | 5-Cl | 250, 2 NaOH |
| 68 | 2-OMe-4-Me-5-Cl-phenyl | —(CH₂)₂—cyclohexyl | —CH₂CO₂H | 4,6-diMe | 200 |
| 69 | 2-OMe-4-Me-5-OMe-...-Me-phenyl | —(CH₂)₂—cyclohexyl | —CH₂CO₂Na | 4,5-diCl | 185, NaOH |
| 70 | 2-OMe-4-Me-5-Cl-phenyl | —(CH₂)₂—cyclohexyl | —CH₂CO₂Na | 4,5-diCl | 190, NaOH |
| 71 | 2-OMe-4-Me-5-Cl-phenyl | —(CH₂)₂—cyclohexyl | —CH₂CO₂H | 4,7-diMe | 190, CF₃CO₂H |
| 72 | 2-OMe-4-Me-5-OMe-Me-phenyl | —(CH₂)₂—cyclohexyl | —CH₂CO₂H | 4,7-diMe | 184, CF₃CO₂H |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 73 | 2,5-diMeO-4-Me-phenyl | —(CH₂)₂-cyclohexyl | —CH₂CO₂H | 5,6-diMe | 201 HCl |
| 74 | 2,5-diMeO-4-Me-phenyl | —(CH₂)₂-cyclohexyl | (CH₂)₃CO₂H | H | 168 |
| 75 | 4-Cl-2,5-diMeO-phenyl | —(CH₂)₂-cyclohexyl | —CH₂CO₂H | 4,5-diOMe | 145 CF₃CO₂H |
| 76 | 2,5-diMeO-4-Me-phenyl | —(CH₂)₄tBu | —CH₂CO₂Na | H | 228 |
| 77 | 4-Cl-2,5-diMeO-phenyl | —(CH₂)₂-cyclohexyl | —CH₂CO₂H | 4,6-diOMe | 175 CF₃CO₂H |
| 78 | 2,5-diMeO-4-Me-phenyl | —(CH₂)₂-cyclohexyl | —CH₂CO₂H | 4-Cl | 178 CF₃CO₂H |

TABLE 3-continued
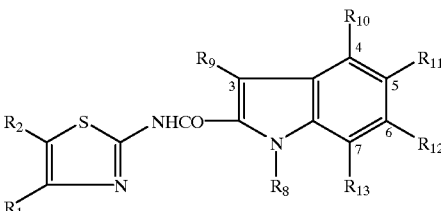
| Examples | R₁ | R₂ | R₈ | R₉, R₁₀, R₁₁, R₁₂, R₁₃ | m.p. °C. Salt or solvate |
|---|---|---|---|---|---|
| 79 | 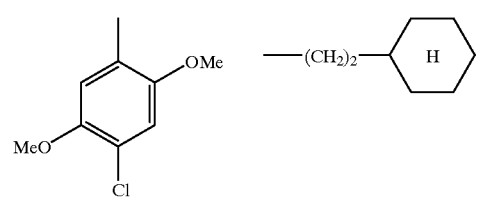 | —(CH₂)₂—⬡H | —CH₂CO₂H | 4-Cl | 180 CF₃CO₂H |
| 80 | 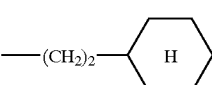 | —(CH₂)₂—⬡H | —CH₂CO₂H | 4,6-diOMe, 5-Me | 165 CF₃CO₂H |
| 81 | 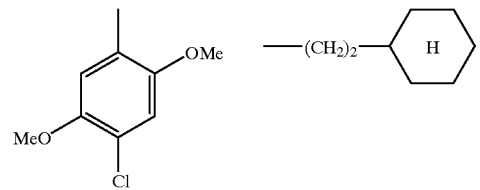 | —(CH₂)₂—⬡H | —CH₂CO₂H | 3-Me | 164 CF₃CO₂H HCl |
| 82 | 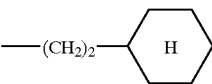 | —(CH₂)₂—⬡H | —(CH₂)₄CO₂H | 5-Me | 248 HCl |
| 83 | 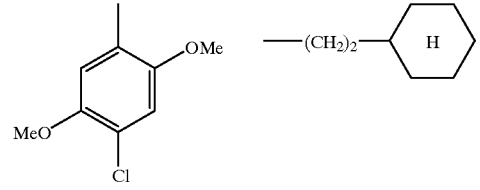 | —(CH₂)₂—⬡H | —(CH₂)₄CO₂H | 5-Me | 245 |
| 84 | 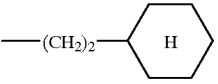 | —(CH₂)₂—⬡H | —(CH₂)₅CO₂H | 5-Me | 139 HCl |

TABLE 3-continued
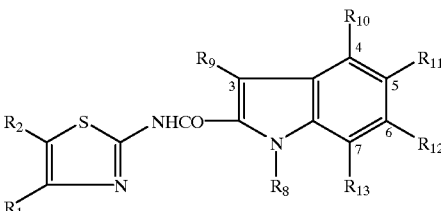
| Examples | R₁ | R₂ | R₈ | R₉, R₁₀, R₁₁, R₁₂, R₁₃ | m.p. °C. Salt or solvate |
|---|---|---|---|---|---|
| 85 | 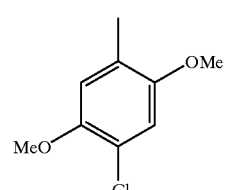 | —(CH₂)₂—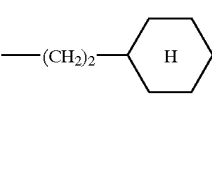 | —(CH₂)₅CO₂H | 5-Me | 135 |
| 86 | 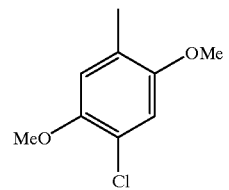 | —(CH₂)₂—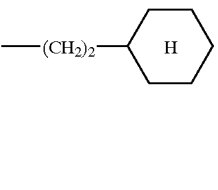 | —CH₂CO₂H | 6-OMe | 170 CF₃CO₂H |
| 87 | 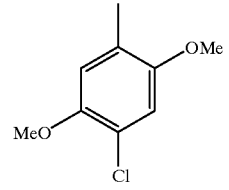 | —(CH₂)₂—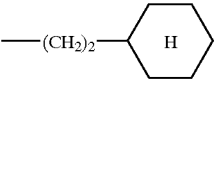 | —(CH₂)₄CO₂H | 5-Cl | 213 HCl |
| 88 | 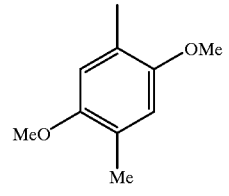 | —(CH₂)₂—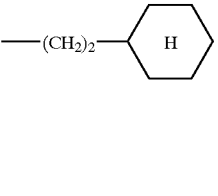 | —(CH₂)₄CO₂H | 5-Cl | 215 HCl |
| 89 | 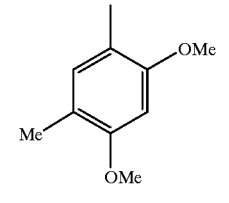 | —(CH₂)₂—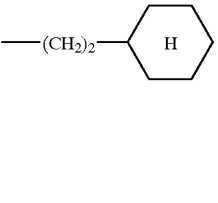 | —(CH₂)₃CO₂H | H | 130 |
| 90 | 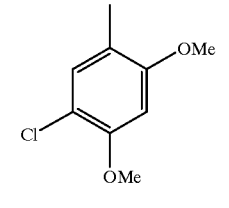 | —(CH₂)₂—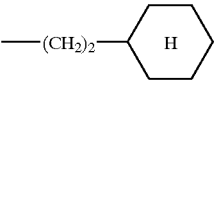 | —(CH₂)₃CO₂H | H | 131 HCl |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 91 | 2,5-dimethoxy-4-methylphenyl (Me top, OMe; MeO, Me bottom) | —(CH₂)₂—cyclohexyl | —(CH₂)₃CO₂H | 4-Me | 270 |
| 92 | 4-chloro-2,5-dimethoxyphenyl (Me, OMe; MeO, Cl) | —(CH₂)₂—cyclohexyl | —(CH₂)₅CO₂H | 4-Me | 120 |
| 93 | 2,5-dimethoxy-4-methylphenyl (Me, OMe; Me, OMe) | —(CH₂)₂—cyclohexyl | —(CH₂)₂CO₂H | H | 155 |
| 94 | 4-chloro-2,5-dimethoxyphenyl (Me, OMe; MeO, Cl) | —(CH₂)₂—cyclohexyl | —(CH₂)₂CO₂H | 5-Cl | 278 |
| 95 | 2,5-dimethoxy-4-methylphenyl (Me, OMe; MeO, Me) | —(CH₂)₂—cyclohexyl | —(CH₂)₂CO₂H | 5-Me | 270 |
| 96 | 4-chloro-2,5-dimethoxyphenyl (Me, OMe; MeO, Cl) | —(CH₂)₂—cyclohexyl | —(CH₂)₂CO₂H | 5-Me | 273 |

TABLE 3-continued
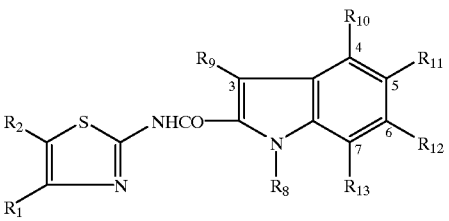
| Examples | R₁ | R₂ | R₈ | R₉, R₁₀, R₁₁, R₁₂, R₁₃ | m.p. °C. Salt or solvate |
|---|---|---|---|---|---|
| 97 | 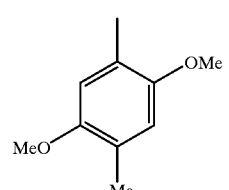 | —(CH₂)₂—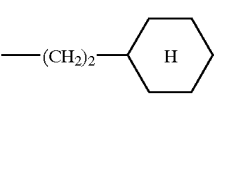H | —(CH₂)₄CO₂H | 4-Me | 265 |
| 98 | 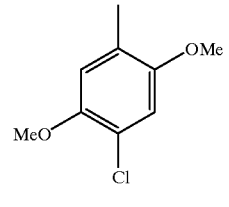 | —(CH₂)₂—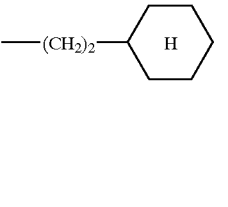H | —(CH₂)₄CO₂H | 4-Me | 260 |
| 99 | 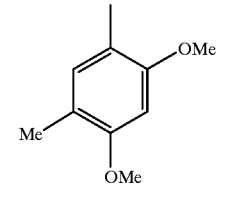 | —(CH₂)₂—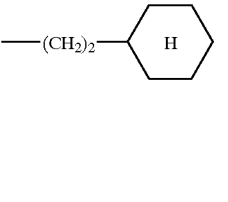H | —(CH₂)₄CO₂H | H | 140 |
| 100 | 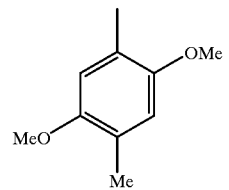 | —(CH₂)₂—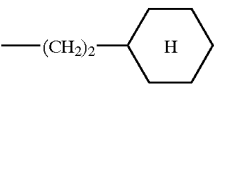H | —(CH₂)₂CO₂H | 4-Me | 285 |
| 101 | 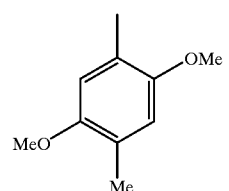 | —(CH₂)₂—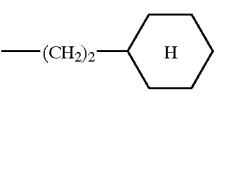H | —CH₂CO₂H | 5-F | 178 CF₃CO₂H |
| 102 | 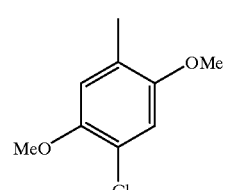 | —(CH₂)₂—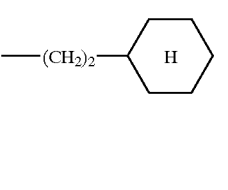H | —CH₂CO₂H | 5-F | 189 CF₃CO₂H |

TABLE 3-continued

| Examples | R₁ | R₂ | R₈ | R₉, R₁₀, R₁₁, R₁₂, R₁₃ | m.p. ° C. Salt or solvate |
|---|---|---|---|---|---|
| 103 | 2-OMe, 4-OMe, 5-Cl, methyl (trimethyl-methoxy-chloro phenyl) | —(CH₂)₂—cyclohexyl | —(CH₂)₂CO₂H | 5-OMe | 270 |
| 104 | 2-OMe, 4-OMe, 5-Cl, methyl phenyl | —(CH₂)₂—cyclohexyl | —(CH₂)₂CO₂H | 4-OMe | 298 |
| 105 | 2-OMe, 4-OMe, 5-Cl, methyl phenyl | —(CH₂)₂—cyclohexyl | —CH₂CO₂H | 5,6,7-triOMe | 165 |
| 106 | 2-OMe, 4-OMe, 5-Me, methyl phenyl | —(CH₂)₂—cyclohexyl | —CH₂CO₂H | 7-OMe | 176 CF₃CO₂H H₂O |
| 107 | 2-OMe, 4-OMe, 5-Cl, methyl phenyl | —(CH₂)₂—cyclohexyl | —CH₂CO₂H | 7-OMe | 182 CF₃CO₂H |
| 108 | 2-OMe, 4-OMe, 5-Me, methyl phenyl | —(CH₂)₂—cyclohexyl | —CH₂CO₂H | 6-SMe | 181 |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 109 | 2-OMe, 4-Cl, 5-OMe-phenyl (with Me) | —(CH₂)₂-cyclohexyl | H | —CH₂CO₂H | 6-SMe | 190 |
| 110 | 2-OMe, 4-Cl, 5-OMe-phenyl (with Me) | —(CH₂)₂-cyclohexyl | H | —CH₂CO₂H | 5-Br | 220 |
| 111 | 2-OMe, 5-OMe, 4-Me-phenyl (with Me) | —(CH₂)₂-cyclohexyl | H | —CH₂CO₂H | 5-Br | 215 |
| 112 | 2-OMe, 5-OMe, 4-Me-phenyl (with Me) | —(CH₂)₂-cyclohexyl | H | —CH₂CO₂H | 7-Me | 150 HCl |
| 113 | 2-OMe, 4-Cl, 5-OMe-phenyl (with Me) | —(CH₂)₂-cyclohexyl | H | —CH₂CO₂H | 7-Me | 147 HCl |
| 114 | 2-OMe, 5-OMe, 4-Me-phenyl (with Me) | —(CH₂)₂-cyclohexyl | H | —CH₂CO₂H | 4-F | 197 HCl |

TABLE 3-continued

Structure: thiazole(R1 at 4, R2 at 5)-NHCO-indole(2-position linked; R9 at 3, R10 at 4, R11 at 5, R12 at 6, R13 at 7, R8 on N)

| Examples | R₁ | R₂ | R₈ | R₉, R₁₀, R₁₁, R₁₂, R₁₃ | m.p. °C. Salt or solvate |
|---|---|---|---|---|---|
| 115 | 5-Cl-2,4-di(OMe)-phenyl (with Me) | —(CH₂)₂—cyclohexyl | H | —CH₂CO₂H | 4-F | 194 |
| 116 | 5-Cl-2,4-di(OMe)-phenyl (with Me) | —(CH₂)₂—cyclohexyl | H | —(CH₂)₃CO₂H | 7-OMe | 172 |
| 117 | 2,4-di(OMe)-5-Me-phenyl (with Me) | —(CH₂)₂—cyclohexyl | H | —(CH₂)₃CO₂H | 7-OMe | 175 |
| 118 | 2,4-di(OMe)-5-Me-phenyl (with Me) | —(CH₂)₂—cyclohexyl | H | —CH₂CO₂H | 3,5-diMe | 122 CF₃CO₂H |
| 119 | 5-Cl-2,4-di(OMe)-phenyl (with Me) | —(CH₂)₂—cyclohexyl | H | —CH₂CO₂H | 3,5-diMe | 128 CF₃CO₂H |
| 120 | 2,4-di(OMe)-5-Me-phenyl (with Me) | —(CH₂)₂—cyclohexyl | H | —(CH₂)₃CO₂H | 3,5-diMe | 138 HCl |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 121 | 2,5-diOMe-4-Me-phenyl (with extra Me) | —(CH₂)₂-cyclohexyl | —CH₂-(2-CO₂H-phenyl) | 5-Me | 200 CF₃CO₂H |
| 122 | 2-OMe-4-Cl-5-OMe-phenyl | —(CH₂)₂-cyclohexyl | —CH₂-(2-CO₂H-phenyl) | 5-Me | 217 CF₃CO₂H |
| 123 | 2,5-diOMe-4-Me-phenyl | —(CH₂)₂-cyclohexyl | —CH₂-(2-CO₂H-phenyl) | 5-Cl | 187 HCl |
| 124 | 2-OMe-4-Cl-5-OMe-phenyl | —(CH₂)₂-cyclohexyl | —CH₂-(2-CO₂H-phenyl) | 5-Cl | 197 HCl |
| 125 | 2-OMe-4-Cl-5-OMe-phenyl | —(CH₂)₂-cyclohexyl | —(CH₂)₂CO₂H | 3,5-diMe | 142 HCl |
| 126 | 2-OMe-4-Cl-5-OMe-phenyl | —(CH₂)₂-cyclohexyl | —(CH₂)₃CO₂H | 3,5-diMe | 134 HCl |

TABLE 3-continued

| Examples | R₁ | R₂ | R₈ | $R_9, R_{10}, R_{11}, R_{12}, R_{13}$ | m.p. °C. Salt or solvate |
|---|---|---|---|---|---|
| 127 | 2,5-diMeO-4-Me-phenyl | —(CH₂)₂-cyclohexyl | H | —CH₂CO₂H | 4,6-diMe | 160 |
| 128 | 5-Cl-2-MeO-4-MeO-phenyl | —(CH₂)₂-cyclohexyl | H | —(CH₂)₃CO₂H | 4,6-diMe | 170 |
| 129 | 2,5-diMeO-4-Me-phenyl | —(CH₂)₂-cyclohexyl | H | —(CH₂)₃CO₂H | 4,6-diMe | 160 |
| 130 | 2,5-diMeO-4-Me-phenyl | —(CH₂)₂-cyclohexyl | H | —CH₂CO₂H | 3-Me, 5-Cl | 157 HCl |
| 131 | 5-Cl-2-MeO-4-MeO-phenyl | —(CH₂)₂-cyclohexyl | H | —CH₂CO₂H | 3-Me, 5-Cl | 172 HCl |
| 132 | 5-Cl-2-MeO-4-MeO-phenyl | —(CH₂)₂-cyclohexyl | H | —CH₂CO₂H | 5-NH₂ | 177 CF₃CO₂H |

TABLE 3-continued

| Examples | R₁ | R₂ | R₈ | $R_9, R_{10}, R_{11}, R_{12}, R_{13}$ | m.p. °C. Salt or solvate |
|---|---|---|---|---|---|
| 133 | 2-OMe, 4-Cl, 5-OMe-phenyl with Me | —(CH₂)₂-cyclohexyl | H | —CH₂CO₂H | 5,6-diMe | 212 |
| 134 | 2-OMe, 4-Me, 5-OMe-phenyl with Me | —(CH₂)₂-cyclohexyl | H | —CH₂CO₂H | 5,7-diCl | 204 |
| 135 | 2-OMe, 4-Cl, 5-OMe-phenyl with Me | —(CH₂)₂-cyclohexyl | H | —CH₂CO₂H | 5,7-diCl | 174 HCl |
| 136 | 2-OMe, 4-Cl, 5-OMe-phenyl with Me | —(CH₂)₂-cyclohexyl | H | —CH₂CO₂H | 4,7-diOMe | 205 gum CF₃CO₂H |
| 137 | 2-OMe, 4-Cl, 5-OMe-phenyl with Me | —(CH₂)₂-cyclohexyl | H | —CH₂CO₂H | 5-F, 7-Me | 181 CF₃CO₂H |
| 138 | 2-OMe, 4-Cl, 5-OMe-phenyl with Me | —(CH₂)₂-cyclohexyl | H | —CH₂CO₂H | 5-OMe, 7-Me | 194 CF₃CO₂H |

TABLE 3-continued
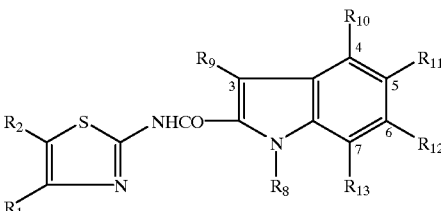
| Examples | R₁ | R₂ | R₈ | R₉, R₁₀, R₁₁, R₁₂, R₁₃ | m.p. °C. Salt or solvate |
|---|---|---|---|---|---|
| 139 | 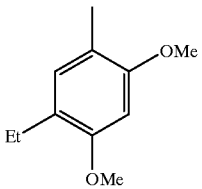 | —(CH₂)₂— 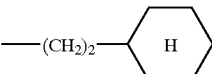 | —CH₂CO₂H | H | 164 CF₃CO₂H |
| 140 | 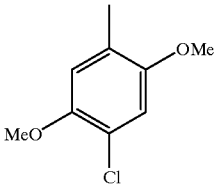 | —(CH₂)₂— 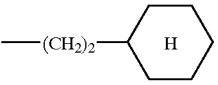 | —CH₂CO₂H | 5-Me, 7-Cl | 170–172 |
| 141 | 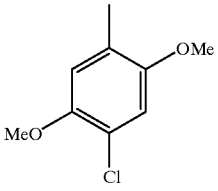 | —(CH₂)₂— 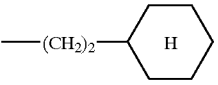 | —CH₂CO₂H | 5-Cl 7-Me | 222 |
| 142 | 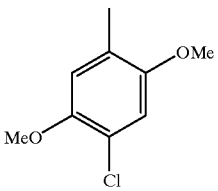 | —(CH₂)₂— 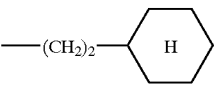 | —CH₂CO₂H | 7-F | 163 CF₃CO₂H |
| 143 | 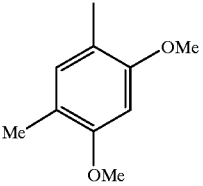 | —(CH₂)₂— 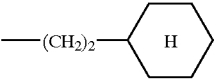 | —CH₂CO₂H | 4,7-diMe | 206 CF₃CO₂H |
| 144 | 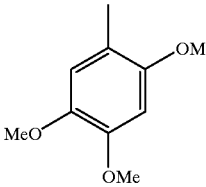 | —(CH₂)₂— 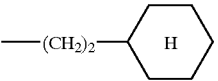 | —CH₂CO₂H | 5-Me | 204 HCl |

TABLE 3-continued
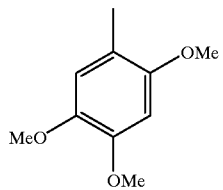
| Examples | R₁ | R₂ | R₈ | R₉, R₁₀, R₁₁, R₁₂, R₁₃ | m.p. °C. Salt or solvate |
|---|---|---|---|---|---|
| 145 | 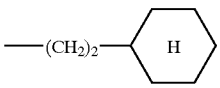 | —(CH₂)₂—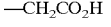 | —CH₂CO₂H | 5-Cl | 201 HCl |
| 146 | 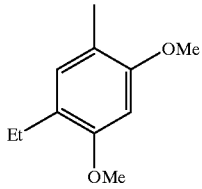 | —(CH₂)₂—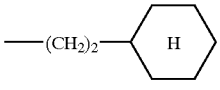 | —CH₂CO₂H | 4,7-diMe | 162 CF₃CO₂H |
| 147 | 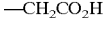 | —(CH₂)₂—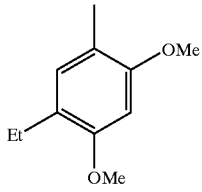 | —CH₂CO₂H | 5-Me | 167 HCl |
| 148 | 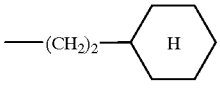 | —(CH₂)₂— | —CH₂CO₂H | 5-Cl | 188 HCl |
| 149 | 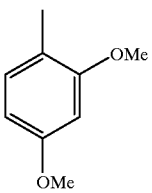 | —(CH₂)₂—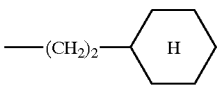 | —CH₂CO₂H | 5-Me | 216 |
| 150 |  | —(CH₂)₂—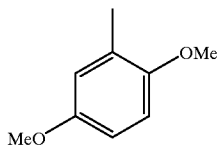 | —CH₂CO₂H | 5-Me | 252 |

TABLE 3-continued
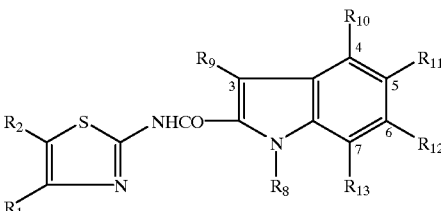
| Examples | R₁ | R₂ | R₈ | R₉, R₁₀, R₁₁, R₁₂, R₁₃ | m.p. °C. Salt or solvate |
|---|---|---|---|---|---|
| 151 | 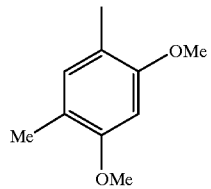 | —(CH₂)₂—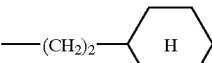 | —CH₂CO₂H | 5-Me | 185 |
| 152 | 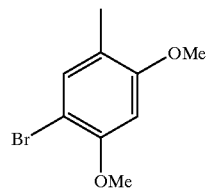 | —(CH₂)₂—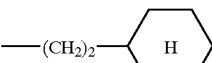 | —CH₂CO₂H | H | 181 |
| 153 | 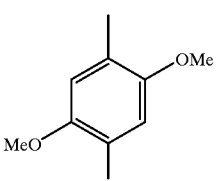 | —(CH₂)₂—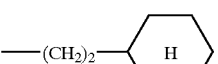 | 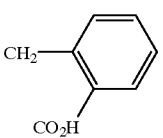 | H | 175 |
| 154 | 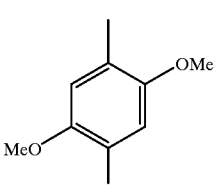 | —(CH₂)₂—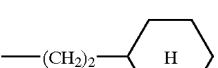 | 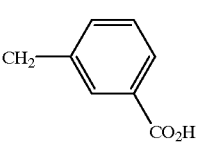 | H | 174 |
| 155 | 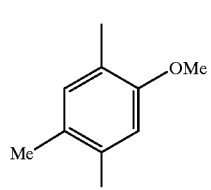 | —(CH₂)₂—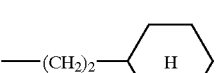 | —CH₂CO₂H | 5-Cl | 180 |
| 156 | 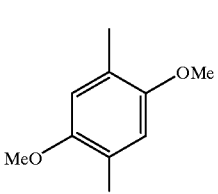 | —(CH₂)₂— | —CH₂CO₂H | 5-Cl 7-CF₃ | 161 ½ HCl |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 157 | 2-OMe, 4-Cl, 5-OMe-phenyl (Me top) | —(CH₂)₂—cyclohexyl | H | —CH₂CO₂H | 5-OCOCH₃ | 211 CF₃CO₂H |
| 158 | 2-OMe, 4-Cl, 5-OMe-phenyl (Me top) | —(CH₂)₂—cyclohexyl | H | —CH₂CO₂H | 5-OH | 186 |
| 159 | 2-OMe, 4-Cl, 5-OMe-phenyl (Me top) | —(CH₂)₂—cyclohexyl | H | —CH₂CO₂H | 4-Me 5-Cl | 175 ⅓ HCl |
| 160 | 2-OMe, 4-Cl, 5-OMe-phenyl (Me top) | —(CH₂)₂—cyclohexyl | H | —CH₂CO₂H | 4-Me 7-Cl | 165 |
| 161 | 2-OMe, 4-Cl, 5-OMe-phenyl (Me top) | —(CH₂)₂—cyclohexyl | H | —CH₂CO₂H | 4-OH | 181 |
| 162 | 2-OMe, 4-Cl, 5-OMe-phenyl (Me top) | —(CH₂)₂—cyclohexyl | H | —CH₂CO₂H | 5-Cl 7-F | 203 |

TABLE 3-continued
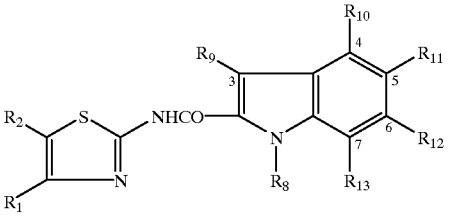
| Examples | R₁ | R₂ | R₈ | R₉, R₁₀, R₁₁, R₁₂, R₁₃ | m.p. °C. Salt or solvate |
|---|---|---|---|---|---|
| 163 | 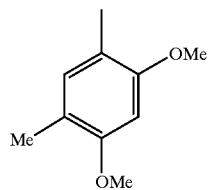 | 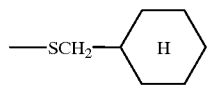 | —CH₂CO₂H | 5,7-diMe | 130 |
| 164 | 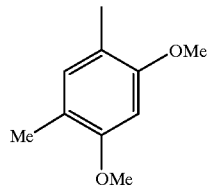 | 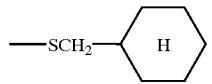 | —CH₂CO₂H | 5-Me | 227 |
| 165 | 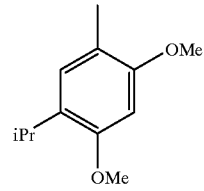 | 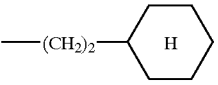 | —CH₂CO₂H | H | 250 Na 2NaOH |
| 166 | 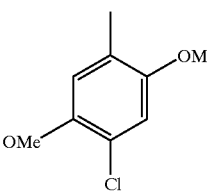 | 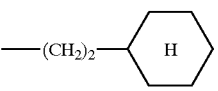 | —CH₂CO₂H | 4-OMe 7-Me | 150 ½ CF₃CO₂H |
| 167 | 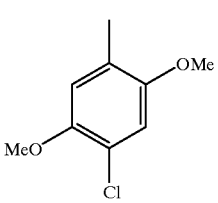 | 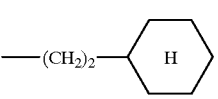 | —CH₂CO₂H | 5-Me 7-F | 173 |

TABLE 3-continued

| Examples | R₁ | R₂ | R₈ | R₉, R₁₀, R₁₁, R₁₂, R₁₃ | m.p. °C. Salt or solvate |
|---|---|---|---|---|---|
| 168 | 4-methyl-2,5-dimethoxy-5-chlorophenyl | —SCH₂—cyclohexyl | —CH₂CO₂H | 5-Me | 155 ¼ HCl |
| 169 | 4-methyl-2,5-dimethoxy-5-chlorophenyl | —SCH₂—cyclohexyl | —CH₂CO₂H | 5,7-diMe | 140 ⅓ HCl |
| 170 | 4-methyl-2,5-dimethoxy-5-chlorophenyl | —(CH₂)₂—cyclohexyl | —CH₂CO₂H | —OCOCH₃ | 196 CF₃CO₂H |

EXAMPLE 171

5-Amino-2-(5-cyclohexylethyl-4-(2,5-dimethoxy-4-methylphenyl)-2-thiazolylcarbamoyl)-1-indolecarboxylic acid. trifluoroacetic acid

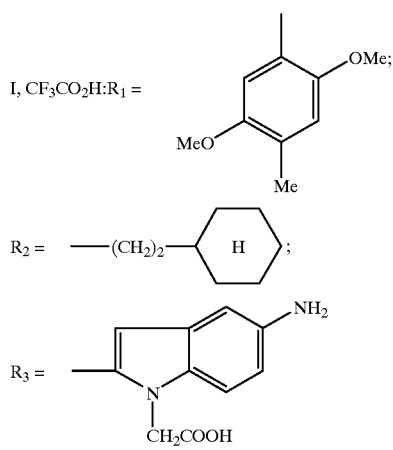

0.6 g of the compound from Preparation 2.18 is mixed with 0.6 g of the compound from Preparation 1.1, 0.7 g of BOP and 0.21 ml of Et₃N in 2 ml of DMF and the mixture is left stirring overnight. 5 ml of pH 2 buffer solution are added and the precipitate is filtered off and then taken up in EtOAc. This solution is washed with pH 2 buffer solution and with Na₂CO₃ solution and then dried over MgSO₄. The residue is chromatographed on silica, eluting with DCM/EtOAc (100/3; v/v). The fractions containing the product are combined and then taken up in 10 ml of TFA and left stirring for 2 hours. The solvents are evaporated off and the residue is then triturated from water at pH 4 to give 740 mg of the expected compound: m.p.=183° C.

Working according to the usual methods, starting with the compounds from Preparations 3.1, 3.2 and 3.3 and the compound of Preparation 1.4, the compounds according to the invention described in the table below are prepared.

TABLE 4

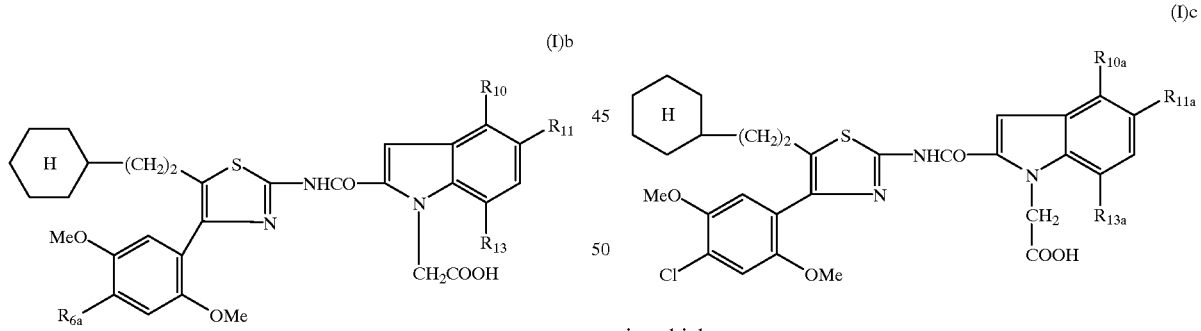

What is claimed is:

1. Compound of formula:

(I)b in which:

$R_{6a}$ a chlorine or a methyl;

$R_{10}$, $R_{11}$ and $R_{13}$ are independently of each other, hydrogen, a methyl, ethyl, hydroxyl, acetyloxy, methoxy, ethoxy, methylthio, trifluoromethyl or amino group or a halogen;

with the limitation that one or two of the substituents $R_{10}$, $R_{11}$ and $R_{13}$ are other than hydrogen;

as well as the salts and solvates thereof.

2. Compound according to claim 1, of formula:

(I)c in which:

one or two of the substituents $R_{10a}$, $R_{11a}$ and $R_{13a}$ are a methyl, a methoxy, a chlorine, a fluorine or a trifluoromethyl, the other(s) being hydrogen, as well as the salts and solvates thereof.

3. Compound according to claim 2, chosen from:

2-(4-(4-chloro-2,5-dimethoxyphenyl)-5-(2-cyclohexylethyl)thiazol-2-ylcarbamoyl)-5-methylindole-1-acetic acid;

2-(4-(4-chloro-2,5-dimethoxyphenyl)-5-(2-cyclohexylethyl)thiazol-2-ylcarbamoyl)-5,7-dimethylindole-1-acetic acid;

2-(4-(4-chloro-2,5-dimethoxyphenyl)-5-(2-cyclohexylethyl)thiazol-2-ylcarbamoyl)-4-methoxyindole-1-acetic acid;

2-(4-(4-chloro-2,5-dimethoxyphenyl)-5-(2-cyclohexylethyl)thiazol-2-ylcarbamoyl)-4-methylindole-1-acetic acid;
2-(4-(4-chloro-2,5-dimethoxyphenyl)-5-(2-cyclohexylethyl)thiazol-2-ylcarbamoyl)-4,5-dimethylindole-1-acetic acid;
2-(4-(4-chloro-2,5-dimethoxyphenyl)-5-(2-cyclohexylethyl)thiazol-2-ylcarbamoyl)-5-methoxyindole-1-acetic acid;
2-(4-(4-chloro-2,5-dimethoxyphenyl)-5-(2-cyclohexylethyl)thiazol-2-ylcarbamoyl)-5-chloroindole-1-acetic acid;
2-(4-(4-chloro-2,5-dimethoxyphenyl)-5-(2-cyclohexylethyl)thiazol-2-ylcarbamoyl)-4,5-dichloroindole-1-acetic acid;
2-(4-(4-chloro-2,5-dimethoxyphenyl)-5-(2-cyclohexylethyl)thiazol-2-ylcarbamoyl)-4,7-dimethylindole-1-acetic acid;
2-(4-(4-chloro-2,5-dimethoxyphenyl)-5-(2-cyclohexylethyl)thiazol-2-ylcarbamoyl)-4,5-dimethoxyindole-1-acetic acid;
2-(4-(4-chloro-2,5-dimethoxyphenyl)-5-(2-cyclohexylethyl)thiazol-2-ylcarbamoyl)-7-methoxyindole-1-acetic acid;
2-(4-(4-chloro-2,5-dimethoxyphenyl)-5-(2-cyclohexylethyl)thiazol-2-ylcarbamoyl)-7-methylindole-1-acetic acid;
2-(4-(4-chloro-2,5-dimethoxyphenyl)-5-(2-cyclohexylethyl)thiazol-2-ylcarbamoyl)-5,7-dichloroindole-1-acetic acid;
2-(4-(4-chloro-2,5-dimethoxyphenyl)-5-(2-cyclohexylethyl)thiazol-2-ylcarbamoyl)-4,7-dimethoxyindole-1-acetic acid;
2-(4-(4-chloro-2,5-dimethoxyphenyl)-5-(2-cyclohexylethyl)thiazol-2-ylcarbamoyl)-5-methoxy-7-methylindole-1-acetic acid;
2-(4-(4-chloro-2,5-dimethoxyphenyl)-5-(2-cyclohexylethyl)thiazol-2-ylcarbamoyl)-5-methyl-7-chloroindole-1-acetic acid;
2-(4-(4-chloro-2,5-dimethoxyphenyl)-5-(2-cyclohexylethyl)thiazol-2-ylcarbamoyl)-5-chloro-7-methylindole-1-acetic acid;
2-(4-(4-chloro-2,5-dimethoxyphenyl)-5-(2-cyclohexylethyl)thiazol-2-ylcarbamoyl)-5-chloro-7-fluoroindole-1-acetic acid;
2-(4-(4-chloro-2,5-dimethoxyphenyl)-5-(2-cyclohexylethyl)thiazol-2-ylcarbamoyl)-4-methyl-7-chloroindole-1-acetic acid;
2-(4-(4-chloro-2,5-dimethoxyphenyl)-5-(2-cyclohexylethyl)thiazol-2-ylcarbamoyl)-4-methyl-5-chloroindole-1-acetic acid;
2-(4-(4-chloro-2,5-dimethoxyphenyl)-5-(2-cyclohexylethyl)thiazol-2-ylcarbamoyl)-5-chloro-7-trifluoromethylindole-1-acetic acid;
2-(4-(4-chloro-2,5-dimethoxyphenyl)-5-(2-cyclohexylethyl)thiazol-2-ylcarbamoyl)-4-methoxy-7-methylindole-1-acetic acid;

as well as the salts and solvates thereof.

4. Compound according to claim 3, wherein the compound is 2-(4-(4-chloro-2,5-dimethoxyphenyl)-5-(2-cyclohexylethyl)thiazol-2-ylcarbamoyl)-5-methylindole-1-acetic acid, as well as the salts and solvates thereof.

5. Compound according to claim 3, wherein the compound is 2-(4-(4-chloro-2,5-dimethoxyphenyl)-5-(2-cyclohexylethyl)thiazol-2-ylcarbamoyl)-5,7-dimethylindole-1-acetic acid, as well as the salts and solvates thereof.

6. A pharmaceutical composition containing an effective dose of at least one compound of formula I according to claim 1, or one of the pharmaceutically acceptable salts, solvates or hydrates thereof.

7. A method of combating diseases whose treatment requires stimulation of the cholecystokinin CCK-A receptors which comprises administering to a patient in need of such treatment an effective amount of a compound according to claim 1.

8. A method according to claim 1 for the treatment of disorders of the gastrointestinal system.

9. A method according to claim 1 for the treatment of disorders of the central nervous system.

10. A method for the treatment of obesity which comprises administering to a patient in need of such treatment an effective amount of a compound according to claim 1.

11. A method for the treatment of irritable bowel syndrome which comprises administering to a patient in need of such treatment an effective amount of a compound according to claim 1.

12. A method for the treatment of dyskinesia which comprises administering to a patient in need of such treatment an effective amount of a compound according to claim 1.

13. A process for the preparation of a compound of formula (I)b according to claim 1, and salts and solvates thereof, which comprises the following steps:

a) coupling a 2-aminothiazole of formula:

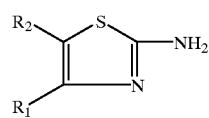

(II)

in which:
$R_1$ is a substituted phenyl group of formula:

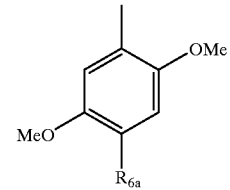

with $R_{6a}$ being a chlorine or a methyl and
$R_2$ is

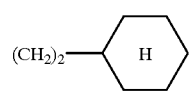

with an acid of formula:

R'$_3$COOH (III)

in which R'₃ is a functional derivative of

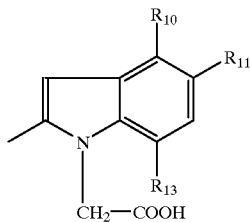

with a protected form of the said acid function, and R₁₀, R₁₁ and R₁₃ being as defined in claim 1;
b) converting the compound thus obtained

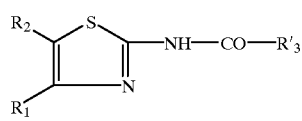

(I')

into a compound of formula (I)b by deprotection of the protected acid function; and
c) isolating the compound of formula (I)b thus obtained, in its current form or in the form of one of the salts or solvates thereof.

14. A pharmaceutical composition containing an effective dose of at least one compound of formula I according to claim 2, or one of the pharmaceutically acceptable salts, solvates or hydrates thereof.

15. A pharmaceutical composition containing an effective dose of at least one compound of formula I according to claim 4, or one of the pharmaceutically acceptable salts, solvates or hydrates thereof.

16. A pharmaceutical composition containing an effective dose of at least one compound of formula I according to claim 6, or one of the pharmaceutically acceptable salts, solvates or hydrates thereof.

17. A pharmaceutical composition containing an effective dose of at least one compound of formula I according to claim 5, or one of the pharmaceutically acceptable salts, solvates or hydrates thereof.

18. A method of combating diseases whose treatment requires stimulation of the cholecystokinin CCK-A receptors which comprises administering to a patient in need of such treatment an effective amount of a compound according to claim 2.

19. A method of combating diseases whose treatment requires stimulation of the cholecystokinin CCK-A receptors which comprises administering to a patient in need of such treatment an effective amount of a compound according to claim 3.

20. A method of combating diseases whose treatment requires stimulation of the cholecystokinin CCK-A receptors which comprises administering to a patient in need of such treatment an effective amount of a compound according to claim 4.

21. A method of combating diseases whose treatment requires stimulation of the cholecystokinin CCK-A receptors which comprises administering to a patient in need of such treatment an effective amount of a compound according to claim 5.

22. A method for the treatment of obesity which comprises administering to a patient in need of such treatment an effective amount of a compound according to claim 2.

23. A method for the treatment of obesity which comprises administering to a patient in need of such treatment an effective amount of a compound according to claim 3.

24. A method for the treatment of obesity which comprises administering to a patient in need of such treatment an effective amount of a compound according to claim 4.

25. A method for the treatment of obesity which comprises administering to a patient in need of such treatment an effective amount of a compound according to claim 5.

26. A method for the treatment of irritable bowel syndrome which comprises administering to a patient in need of such treatment an effective amount of a compound according to claim 2.

27. A method for the treatment of irritable bowel syndrome which comprises administering to a patient in need of such treatment an effective amount of a compound according to claim 3.

28. A method for the treatment of irritable bowel syndrome which comprises administering to a patient in need of such treatment an effective amount of a compound according to claim 4.

29. A method for the treatment of irritable bowel syndrome which comprises administering to a patient in need of such treatment an effective amount of a compound according to claim 5.

30. A method for the treatment of dyskinesia which comprises administering to a patient in need of such treatment an effective amount of a compound according to claim 2.

31. A method for the treatment of dyskinesia which comprises administering to a patient in need of such treatment an effective amount of a compound according to claim 3.

32. A method for the treatment of dyskinesia which comprises administering to a patient in need of such treatment an effective amount of a compound according to claim 4.

33. A method for the treatment of dyskinesia which comprises administering to a patient in need of such treatment an effective amount of a compound according to claim 5.

* * * * *